(12) United States Patent
Surbeck et al.

(10) Patent No.: US 6,684,108 B2
(45) Date of Patent: Jan. 27, 2004

(54) THERAPEUTIC AND DIAGNOSTIC APPARATUS AND METHOD

(75) Inventors: Margaret P. Surbeck, deceased, late of San Francisco, CA (US), by Philip F. Spalding, executor; Homer L. Surbeck, deceased, late of San Francisco, CA (US), by Philip F. Spalding, executor; Robert L. DeVries, Palo Alto, CA (US)

(73) Assignee: INDNJC, Inc., Los Angeles, CA (US)

( * ) Notice: Subject to any disclaimer, the term of this patent is extended or adjusted under 35 U.S.C. 154(b) by 208 days.

(21) Appl. No.: 09/988,483

(22) Filed: Nov. 16, 2001

(65) Prior Publication Data

US 2002/0103518 A1 Aug. 1, 2002

Related U.S. Application Data

(63) Continuation-in-part of application No. 09/804,949, filed on Mar. 31, 2001, now abandoned, which is a division of application No. 09/141,691, filed on Aug. 28, 1998, now Pat. No. 6,321,120, which is a continuation of application No. PCT/US97/23845, filed on Dec. 29, 1997.
(60) Provisional application No. 60/034,561, filed on Dec. 30, 1996, and provisional application No. 60/043,764, filed on Apr. 11, 1997.

(51) Int. Cl.[7] .................................................. A61F 2/00
(52) U.S. Cl. ....................................... 607/101; 128/898

(58) Field of Search .............................. 607/96, 98, 99, 607/101, 154, 155, 156; 606/41, 45, 48, 49, 70, 113; 128/898

(56) References Cited

U.S. PATENT DOCUMENTS

| 3,299,892 A | * | 1/1967 | Kendall et al. | ................ 607/71 |
| 3,513,851 A | * | 5/1970 | Smith et al. | ................... 607/71 |
| 3,516,413 A | * | 6/1970 | McDonald et al. | ............ 607/70 |

* cited by examiner

*Primary Examiner*—Rosiland K. Rollins
(74) *Attorney, Agent, or Firm*—Hughes Hubbard & Reed LLP; Ronald Abramson; Sheryl L. Sandridge

(57) ABSTRACT

An apparatus and method for diagnosing, treating, monitoring and modifying the treatment of cancer and other illnesses in humans and animals is described. A radioscope is used to test a biological sample from a subject, and the results of that test are compared to a tabulation of prior test results in order to diagnose the illness of the subject. The illness is then treated using a therapeutic apparatus involving the low-power, pulsed application of radio frequency tuned with precision of at least one half part per million. A radioscope is then used to monitor the results of the treatment, and the results of the later tests are again compared to a tabulation of prior test results in order to adjust the treatment if necessary.

1 Claim, 79 Drawing Sheets

VARIABLE MODULATION WAVEFORM WITH DC OFFSET 0.0 VDC

**PULSE OUTPUT to MODULATION INPUT on *8662A***

**OUTPUT POWER WAVEFORM FROM hp *8662A***

OUJ-456
TREATED MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

OUJ-471 TREATED MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

OUJ-473
TREATED MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

OUJ-496
TREATED MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

OUJ-506
TREATED MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

OUJ-526
TREATED MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

OUJ-650
TREATED MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

A-486
CONTROL MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

A-488
CONTROL MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

A-490
CONTROL MOUSE

T1 Right Side 2201
T3 Left Side 2203
T2 Left Side 2202
T4 Right thigh 2204

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

A-500
CONTROL MOUSE

T1 Right side 2401
T2 Left leg 2402
T3 Right bottom 2403

TOP GRAPH SHOWS TUMOR VOLUME IN cu inches vs TIME in DAYS

LOWER GRAPH SHOWS WEIGHT IN GRAMS & HEMATOCRIT % vs DAYS

TOP GRAPH SHOWS TUMOR VOLUME IN cu inches vs TIME in DAYS

LOWER GRAPH SHOWS WEIGHT IN GRAMS & HEMATOCRIT % vs DAYS

A-540
CONTROL MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

A-542
CONTROL MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

A-592
CONTROL MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

A-594
CONTROL MOUSE

TOP GRAPH SHOWS TUMOR VOLUME IN cu inches vs TIME in DAYS

LOWER GRAPH SHOWS WEIGHT IN GRAMS & HEMATOCRIT % vs DAYS

TREATED MICE: SHOWING INDIVIDUAL WEIGHT CHANGES IN GRAMS

CONTROL MICE: SHOWING INDIVIDUAL WEIGHT CHANGES IN GRAMS

OUJ-738
TREATED MOUSE

3701
T1 left arm

TOP GRAPH SHOWS TUMOR VOLUME in cu inches vs TIME in days

LOWER GRAPH SHOWS WEIGHT in grams & HEMATOCRIT % vs DAYS

Formula for Tumor Volume in cubic inches = 1/2 length X 1/2 width X height X 2.094
For more detailed information see OUJ-738-Data

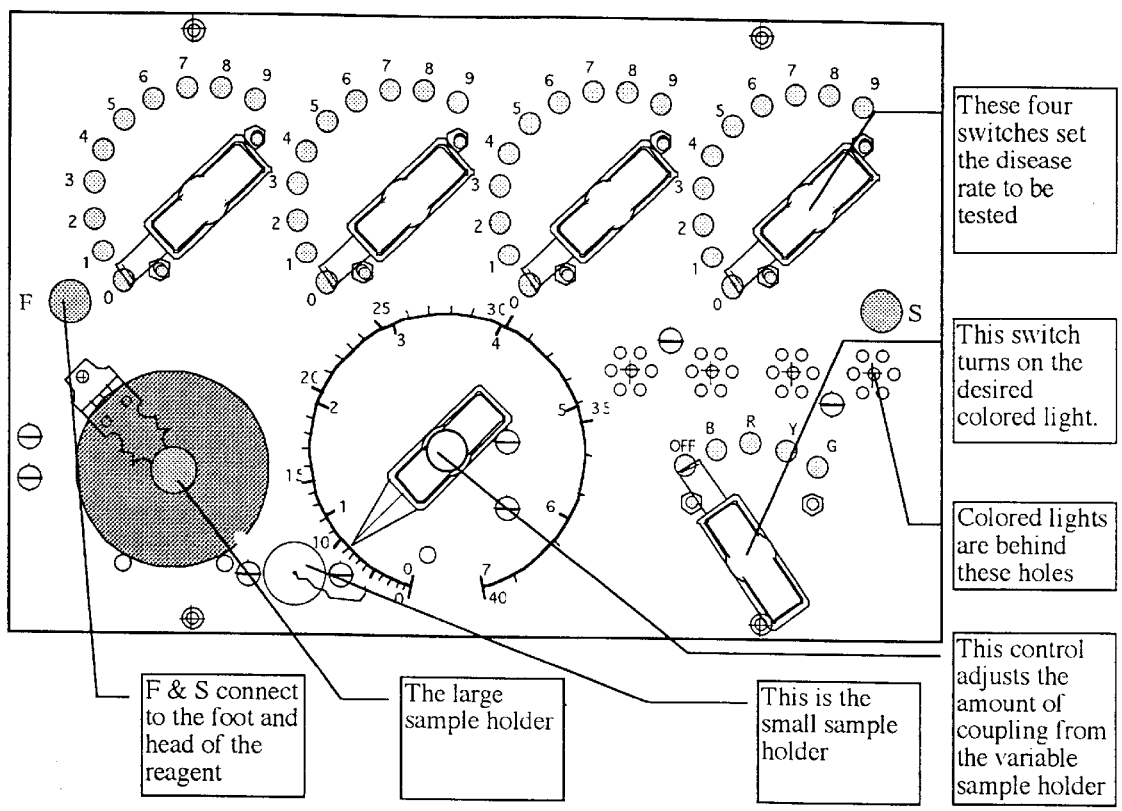
Fig.38— Radioscope Front Panel and Controls

The Radioscope Schematic Diagram

The Radioscope Reagent Connections

Sub-Assembly Overview

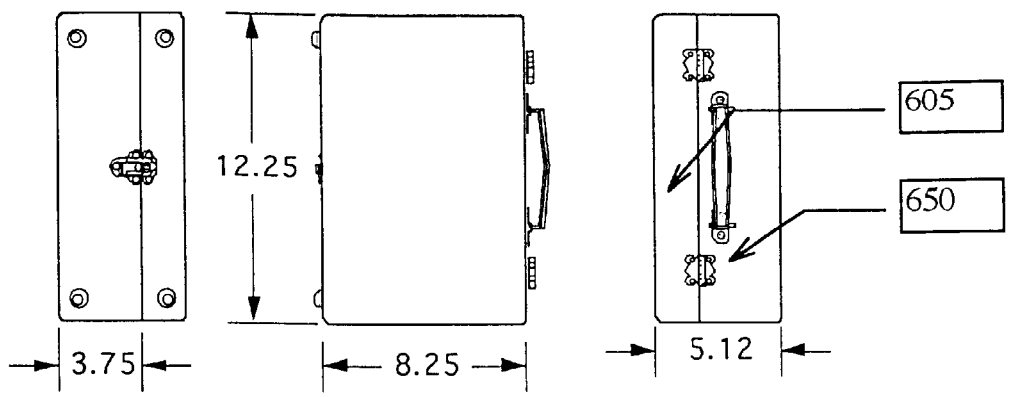
Fig. 42 COMPLETE CASE ASSEMBLY ( #600)
Next Assembly    #100
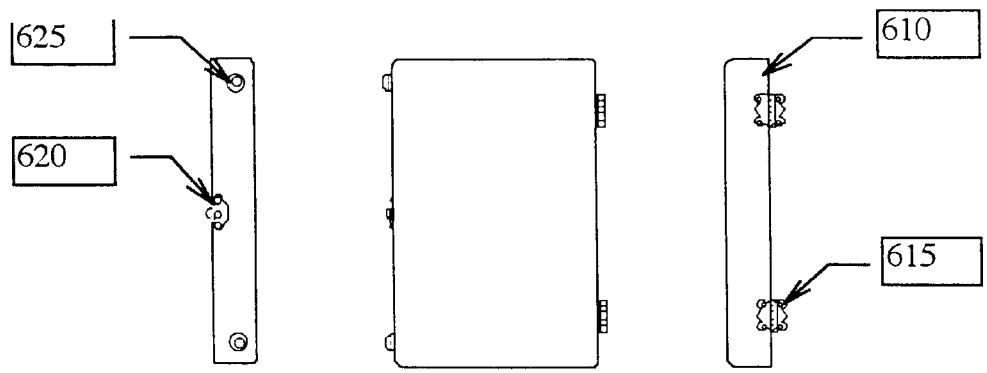
Fig. 43 TOP COVER ASSEMBLY ( #605)
Next Assembly    #600
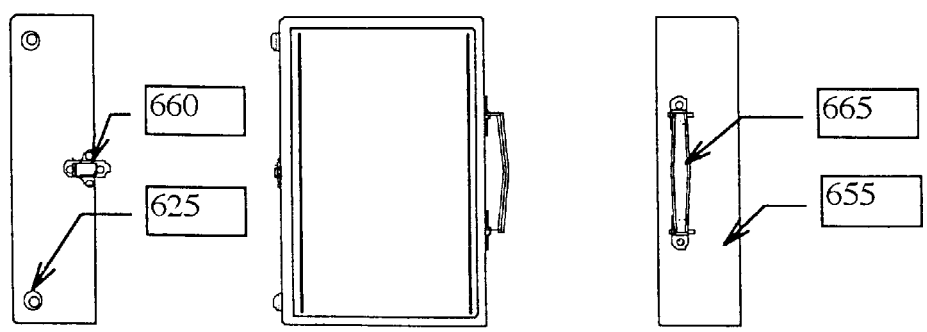
Fig. 44 BOTTOM COVER ASSEMBLY ( #650)
Next Assembly    #600

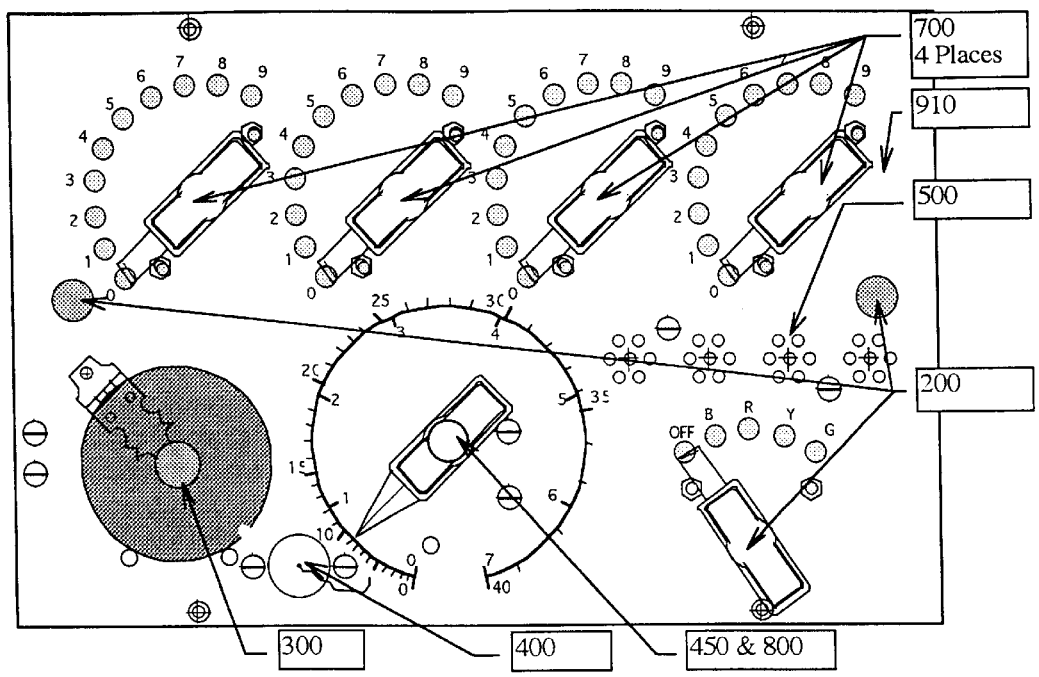
Fig. 45 FRONT PANEL ASSEMBLY ( #900)
Next Assembly #100

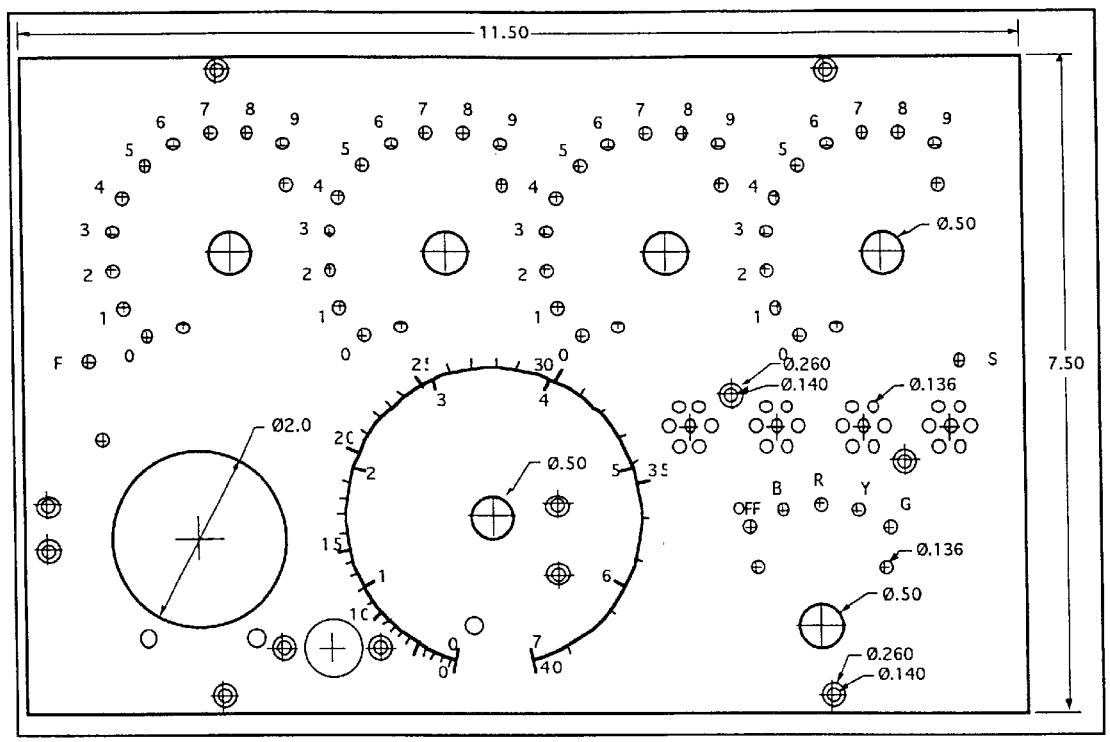
Fig. 46 FRONT PANEL HOLES AND MARKING ( #910)
Next Assembly #900

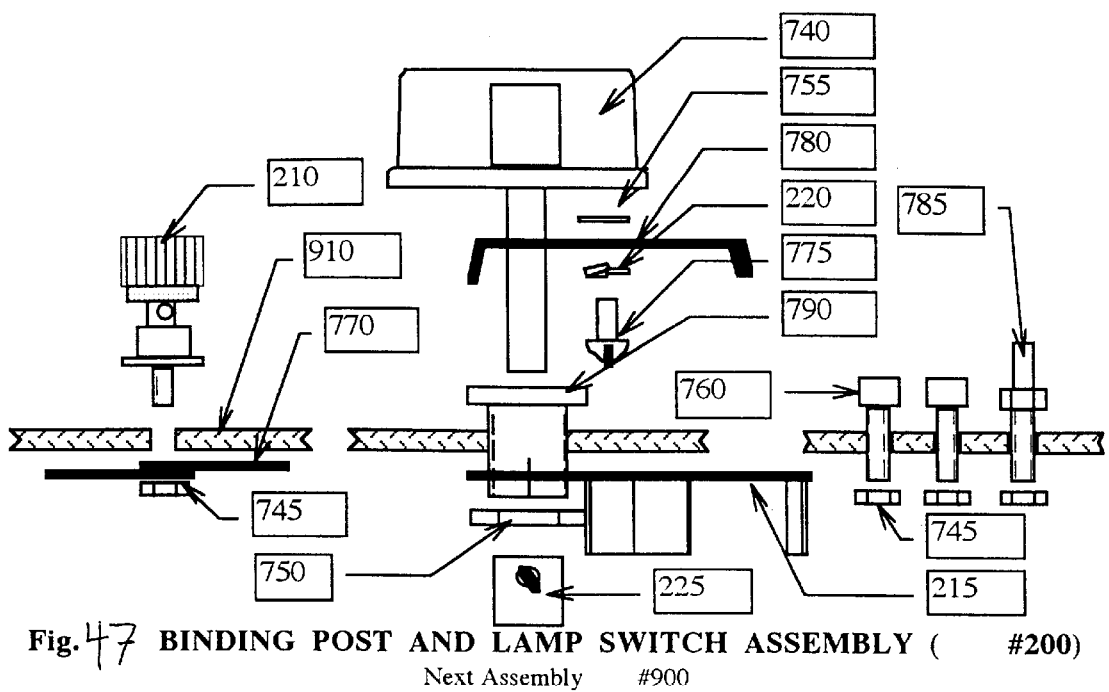
Fig. 47 BINDING POST AND LAMP SWITCH ASSEMBLY ( #200)
Next Assembly    #900

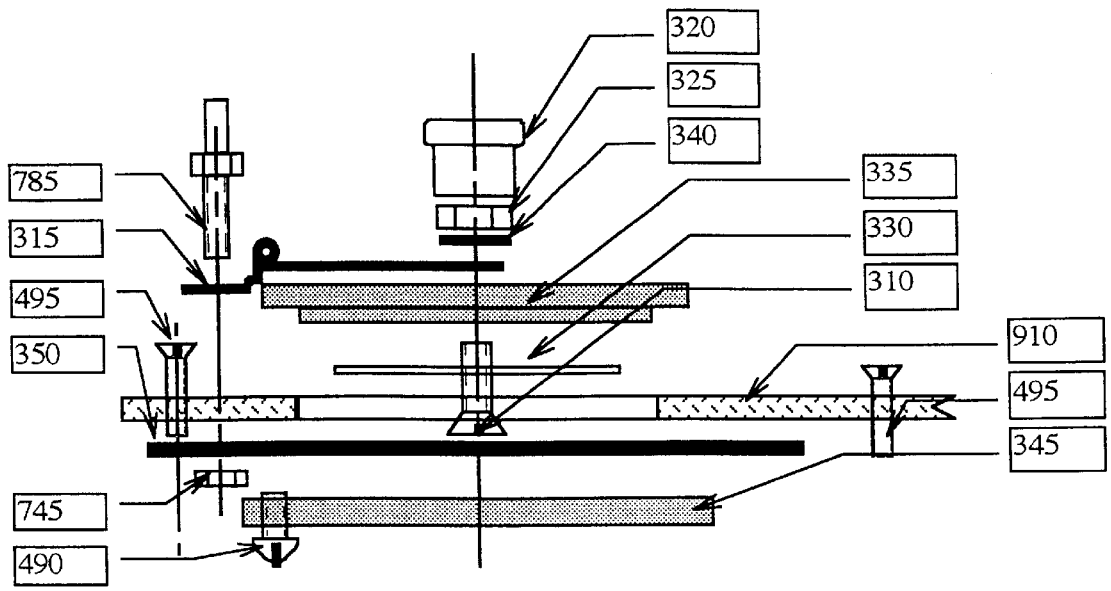
Fig. 48 LARGE SAMPLE ASSEMBLY (    #300)
Next Assembly    #900
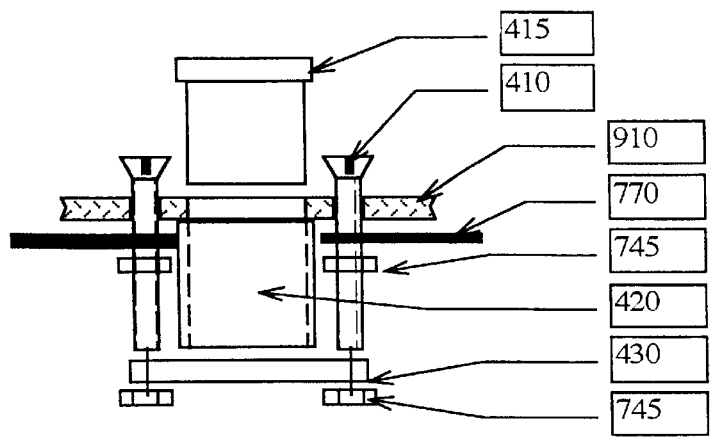
Fig. 49 SMALL SAMPLE ASSEMBLY (    #400)
Next Assembly    #900

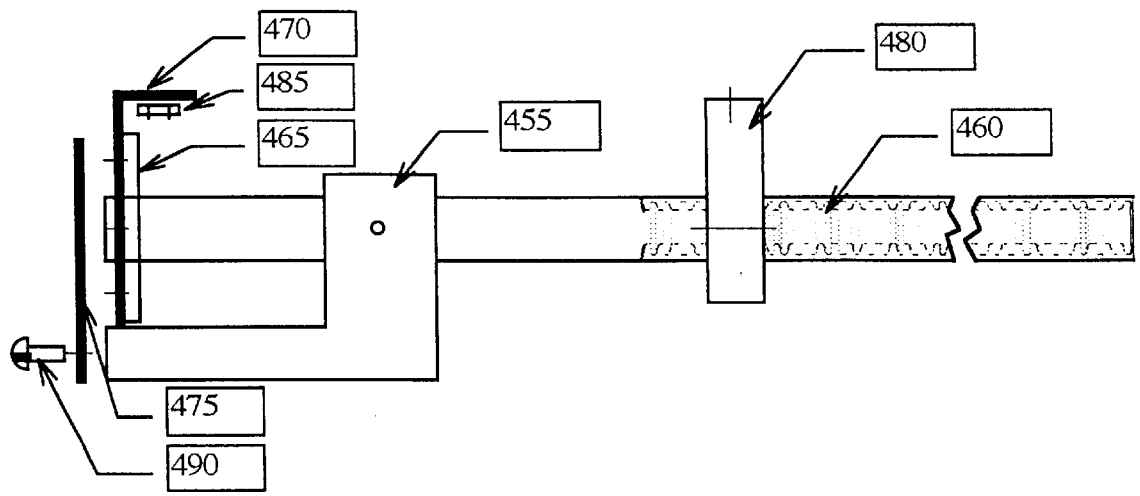
Fig. 50 DIAL SAMPLE ASSEMBLY (    #450)
Next Assembly    #900

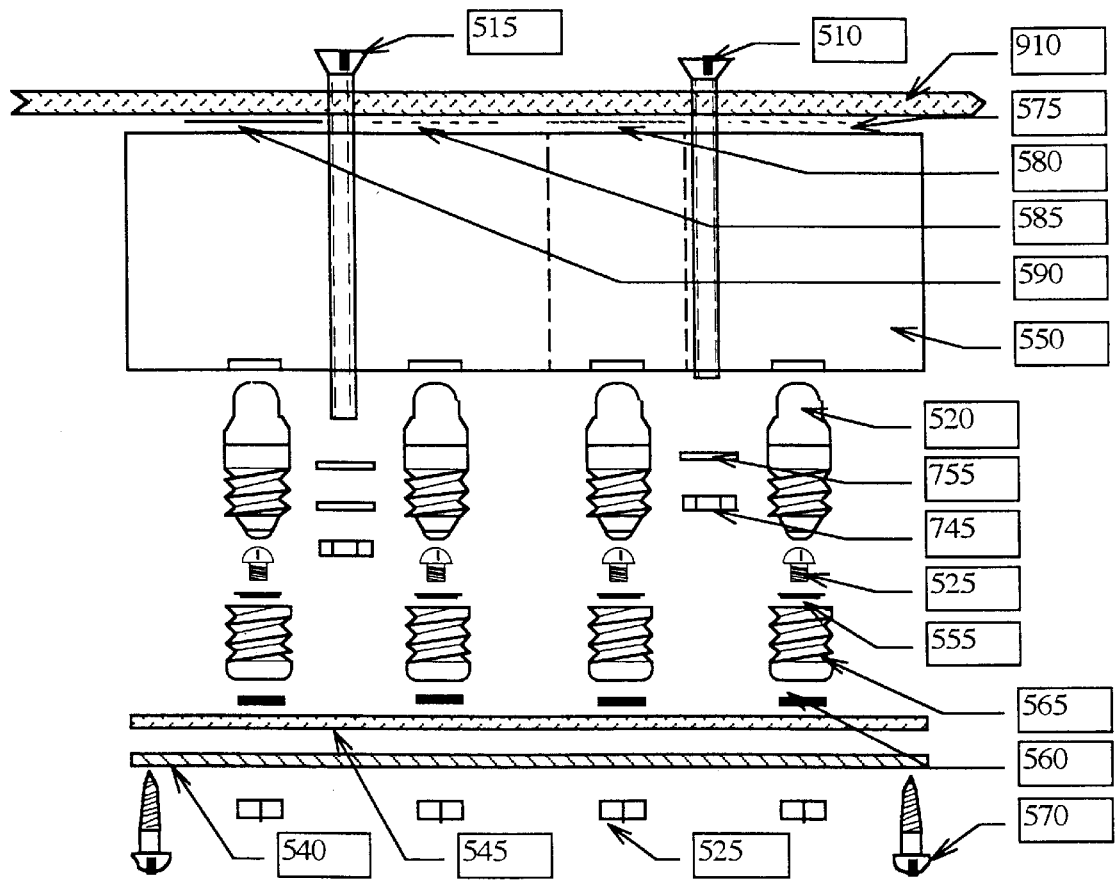
FIG. 51 LAMP HOUSING ASSEMBLY ( #500)
Next Assembly #900

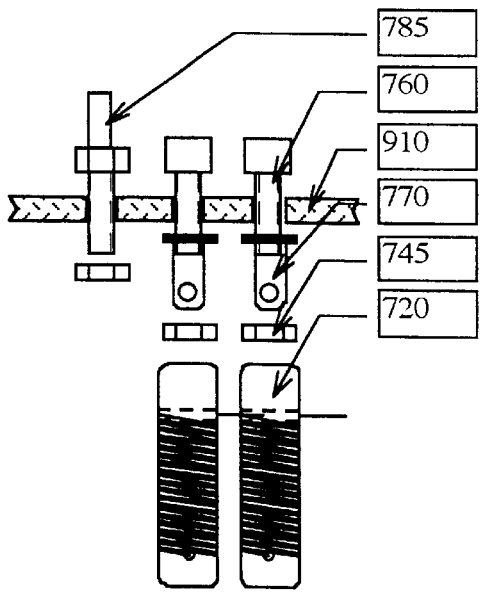
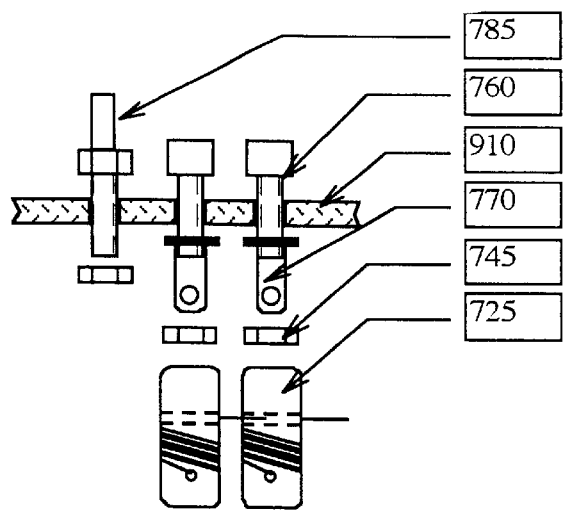
0-9 Thousands Dial      0-9 Hundreds Dial
only 2 of 9 contacts and coils shown
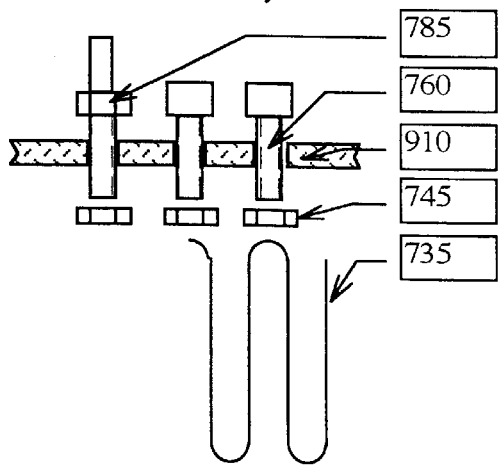
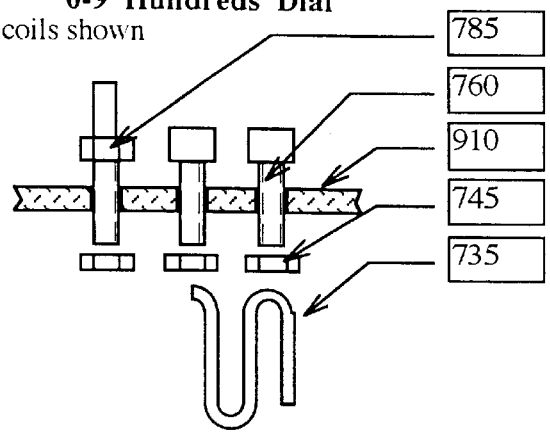
0-9 Tens Dial      0-9 Units Dial
Fig. 52 GAMUT COILS ASSEMBLY ( #700)

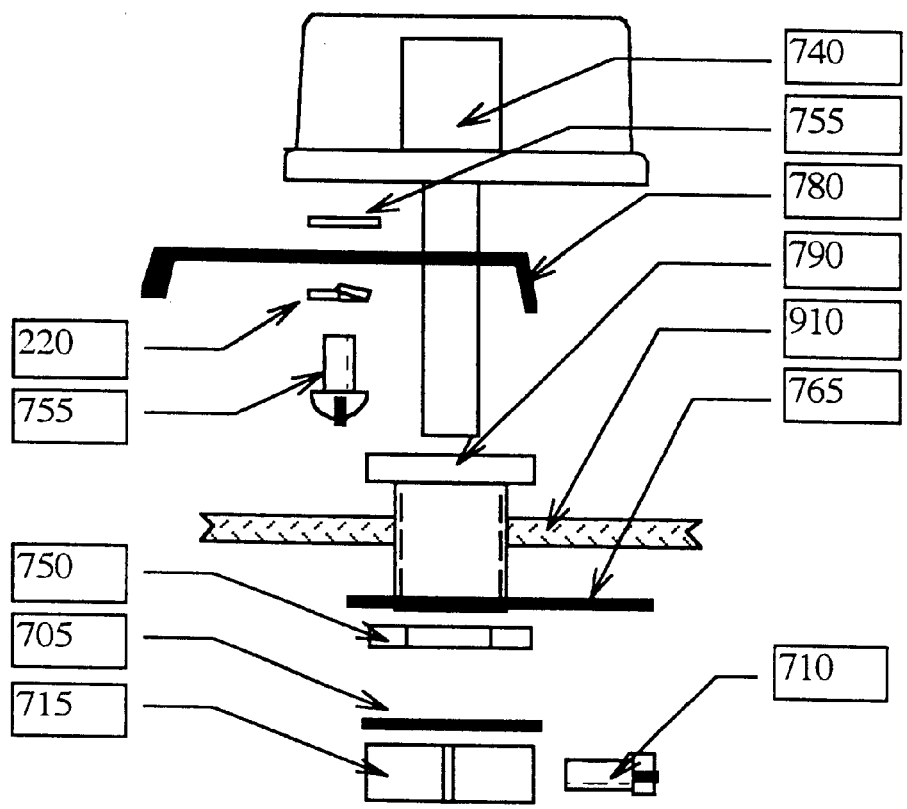
Fig. 53 GAMUT SWITCHES ASSEMBLY ( #700)
Next Assembly #900

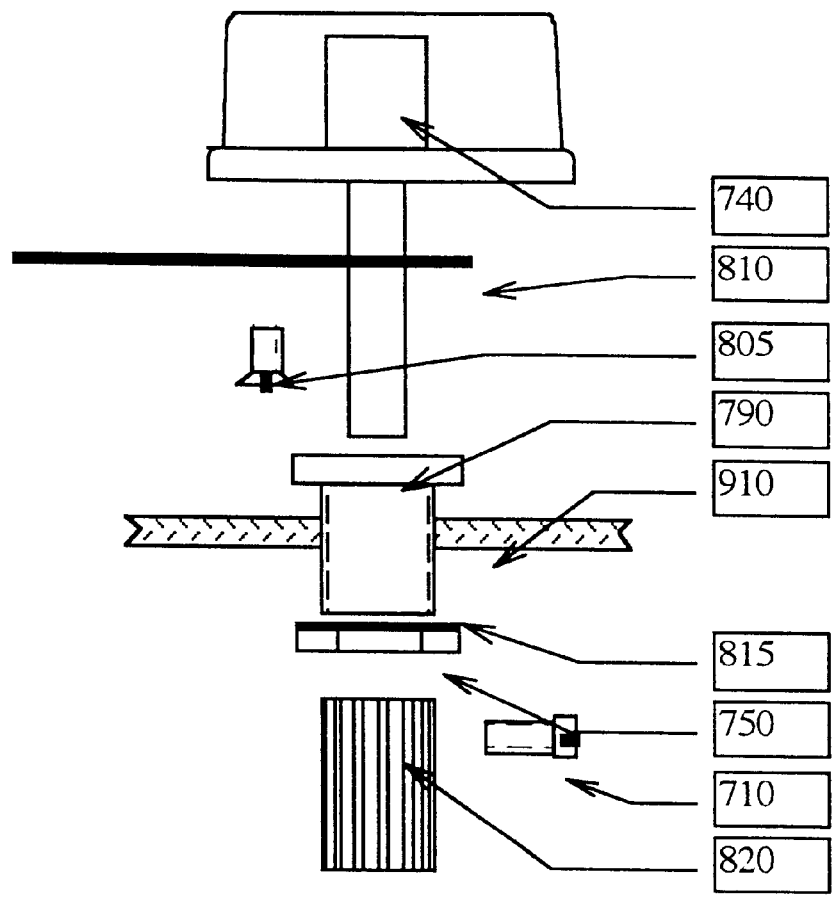
Fig. 54 DIAL KNOB ASSEMBLY (    #800)
Next Assembly    #900

Fig. 55 Battery, Clamp and Nut Installation
Next Assembly     #100
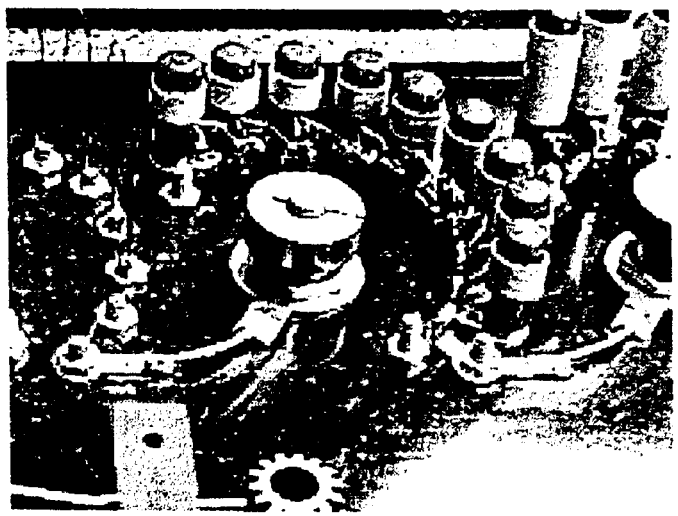
Fig. 56 Wiring the coils
Next Assembly     #100

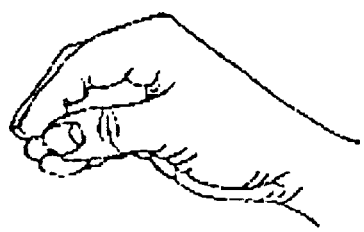
Fig. 57 THE POSITION OF THE FINGERS FOR LOCALIZING
SENSOR LOCATION AND STROKE AREAS ON REAGENT'S ABDOMEN
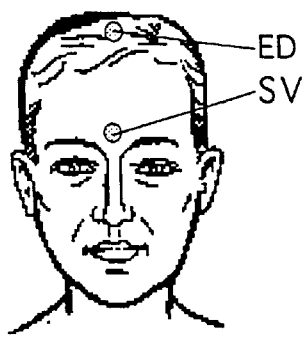 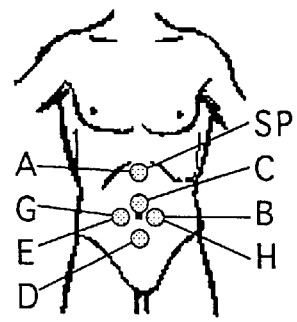
Fig. 58

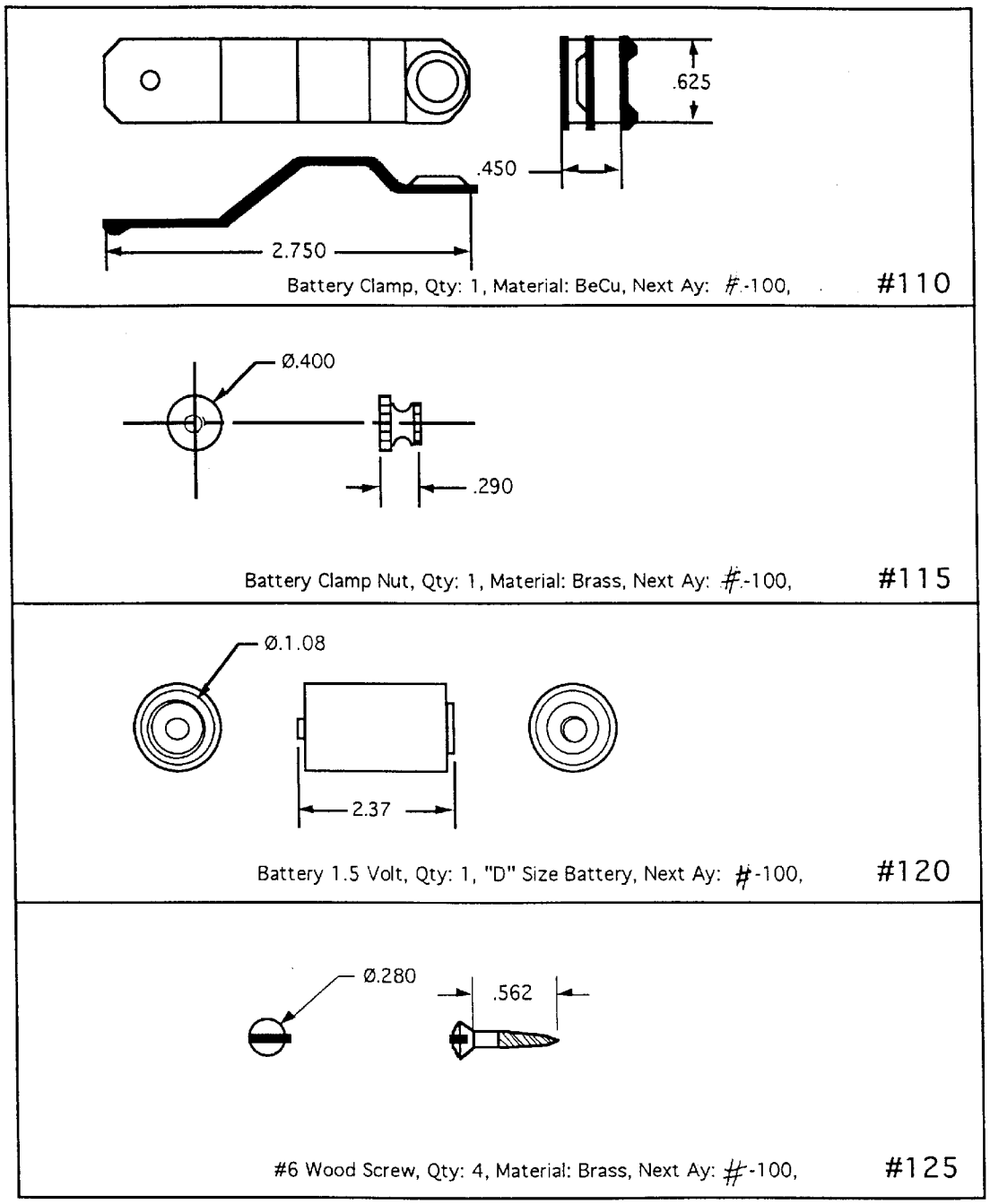
FIG. 59 PART DRAWINGS
1 (at top) THROUGH 4 (at bottom)

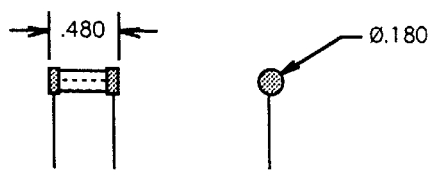
5pF Fixed Capacitor, Qty: 2, Material: Ceramic, Next Ay: #-100,    #130
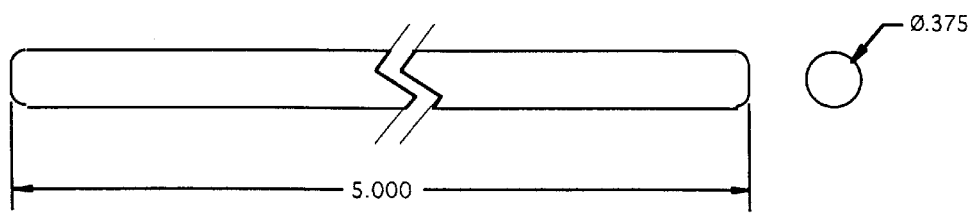
Glass or Lucite Rod, Qty: 1, Material: Glass or Lucite, Next Ay: #-100,    #135
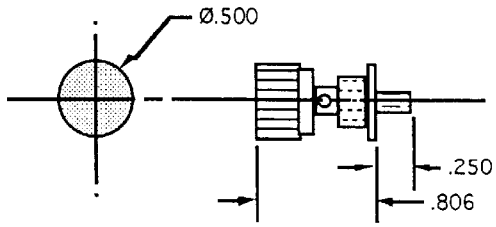
Binding Post, Qty: 2, Material: Brass & Phenol, Next Ay: #-200,    #210
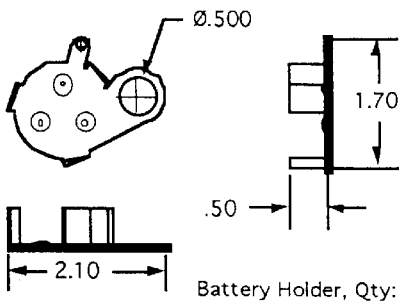
Battery Holder, Qty: 1, Brass, Next Ay: #-200,    #215
FIG. 60 PART DRAWINGS
1 (at top) THROUGH 4 (at bottom)

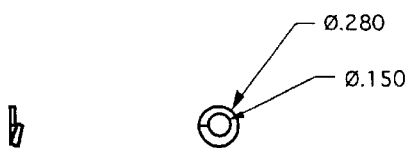
Lock Washer #6, Qty: 5, Stainless Steel, Next Ay: #-200,    #220
Shaft Clamp "B:, Qty: 1, Material: Brass, Next Ay: #-200,    #225
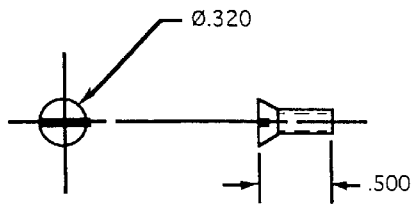
Bolt 8-32 FH Machine Screw, Qty: 1, Material: Stainless Steel, Next Ay: #-300,    #310
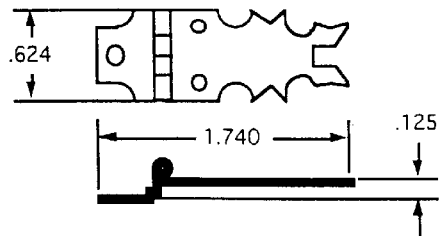
Large Sample Hing, Qty: 1, Brass, Next Ay: #-300,    #315
FIG. 61 PART DRAWINGS
1 (at top) THROUGH 4 (at bottom)

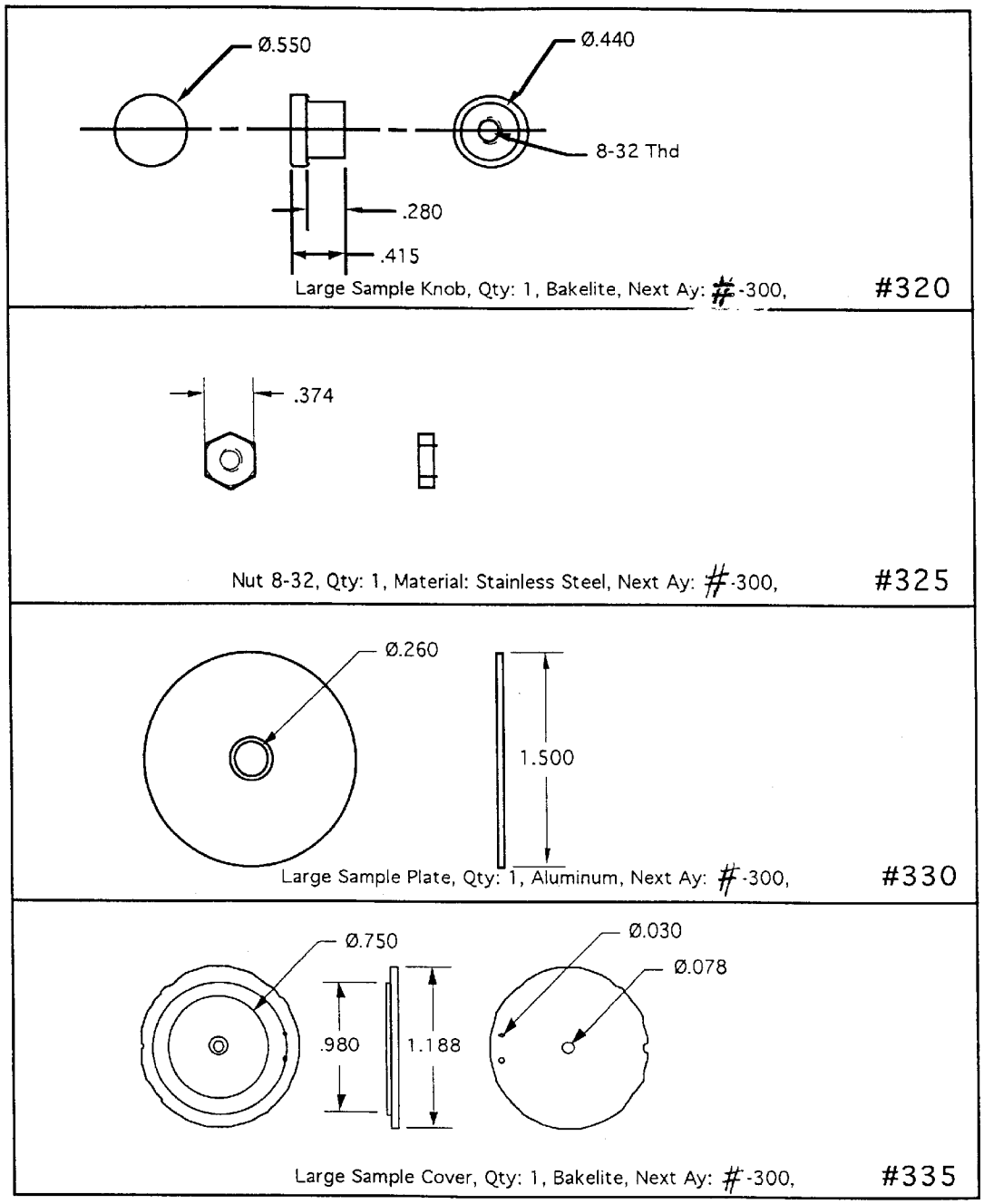
FIG. 62 PART DRAWINGS
1 (at top) THROUGH 4 (at bottom)

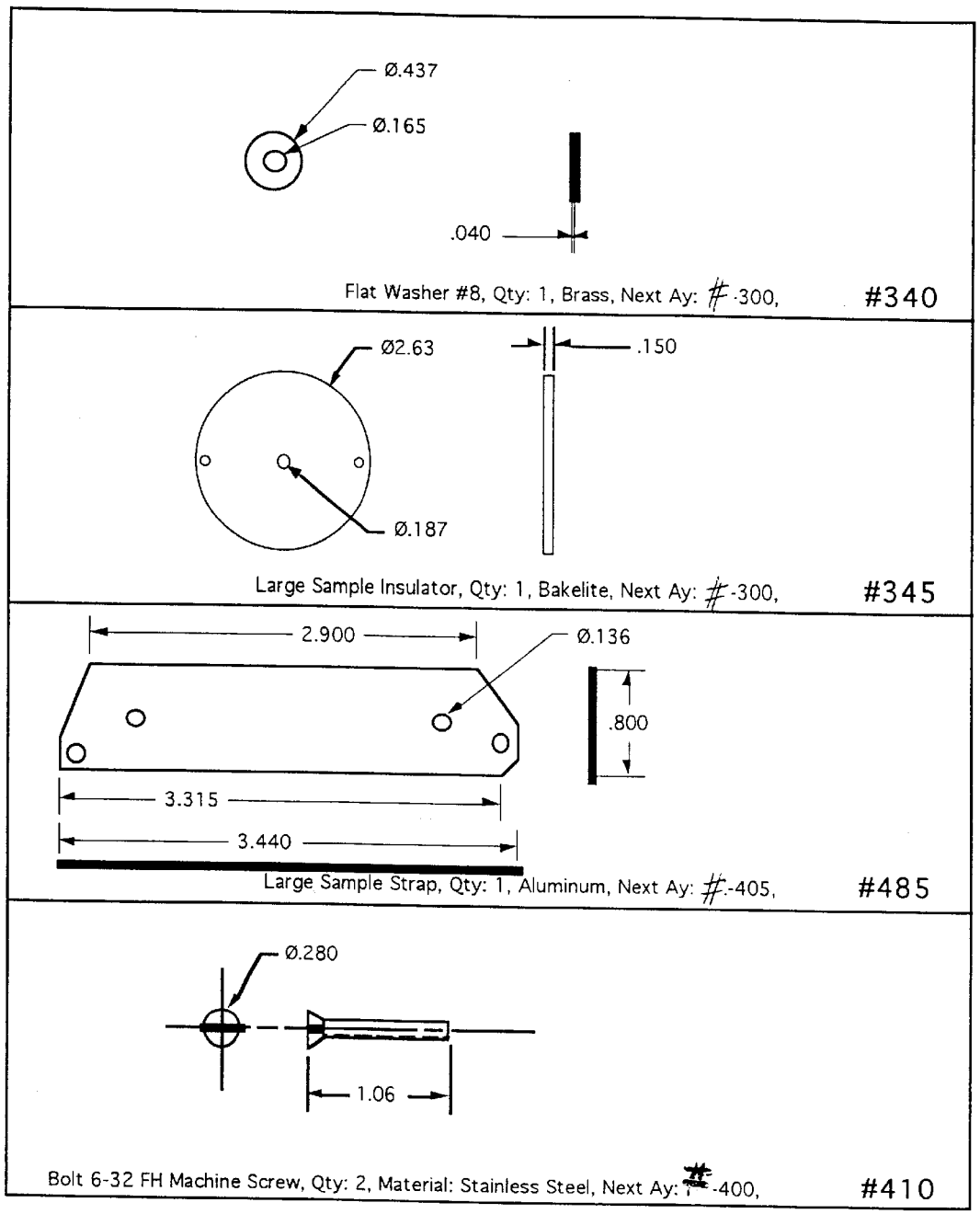
FIG. 63 PART DRAWINGS
1 (at top) THROUGH 4 (at bottom)

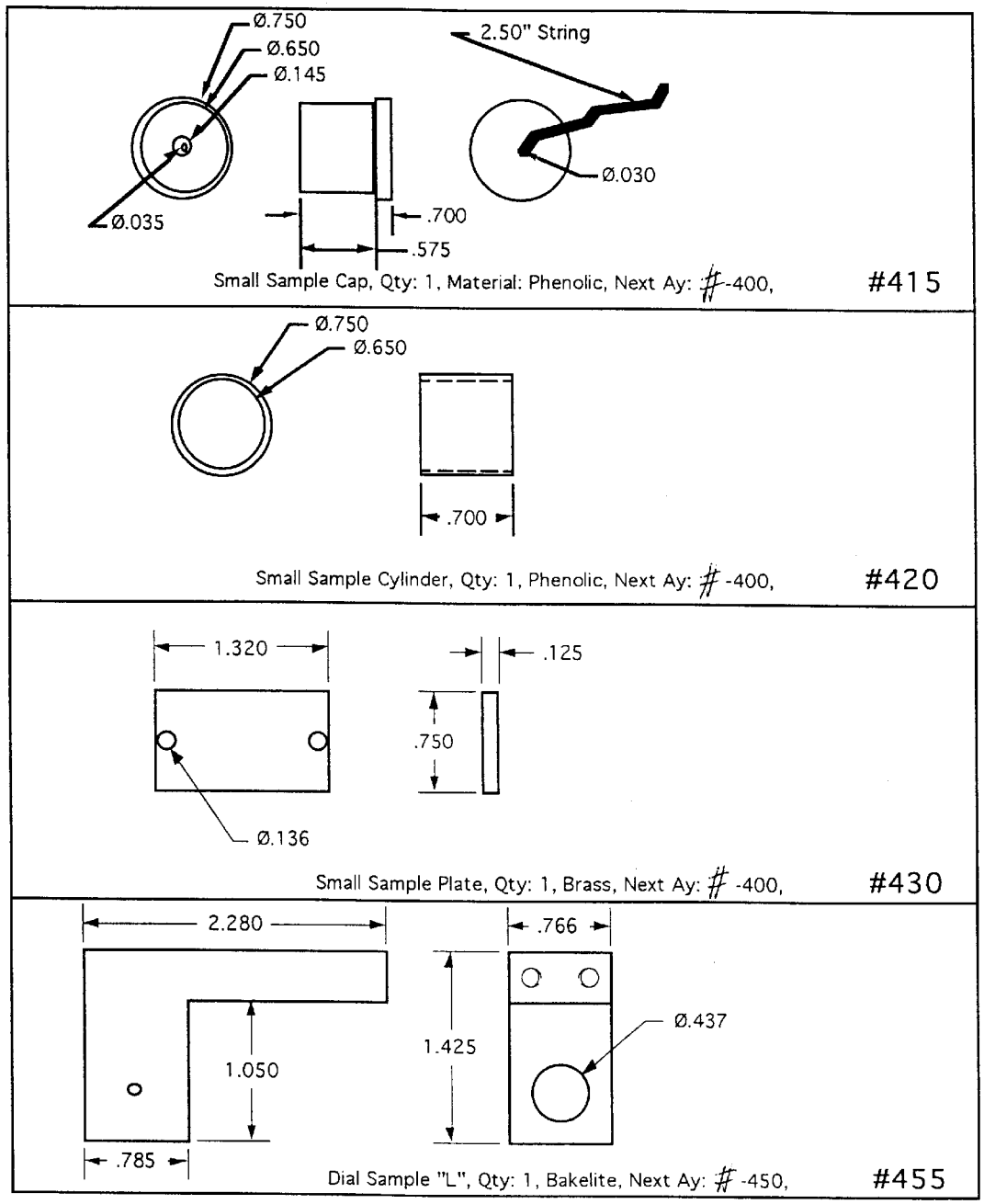
FIG. 64 PART DRAWINGS
1 (at top) THROUGH 4 (at bottom)

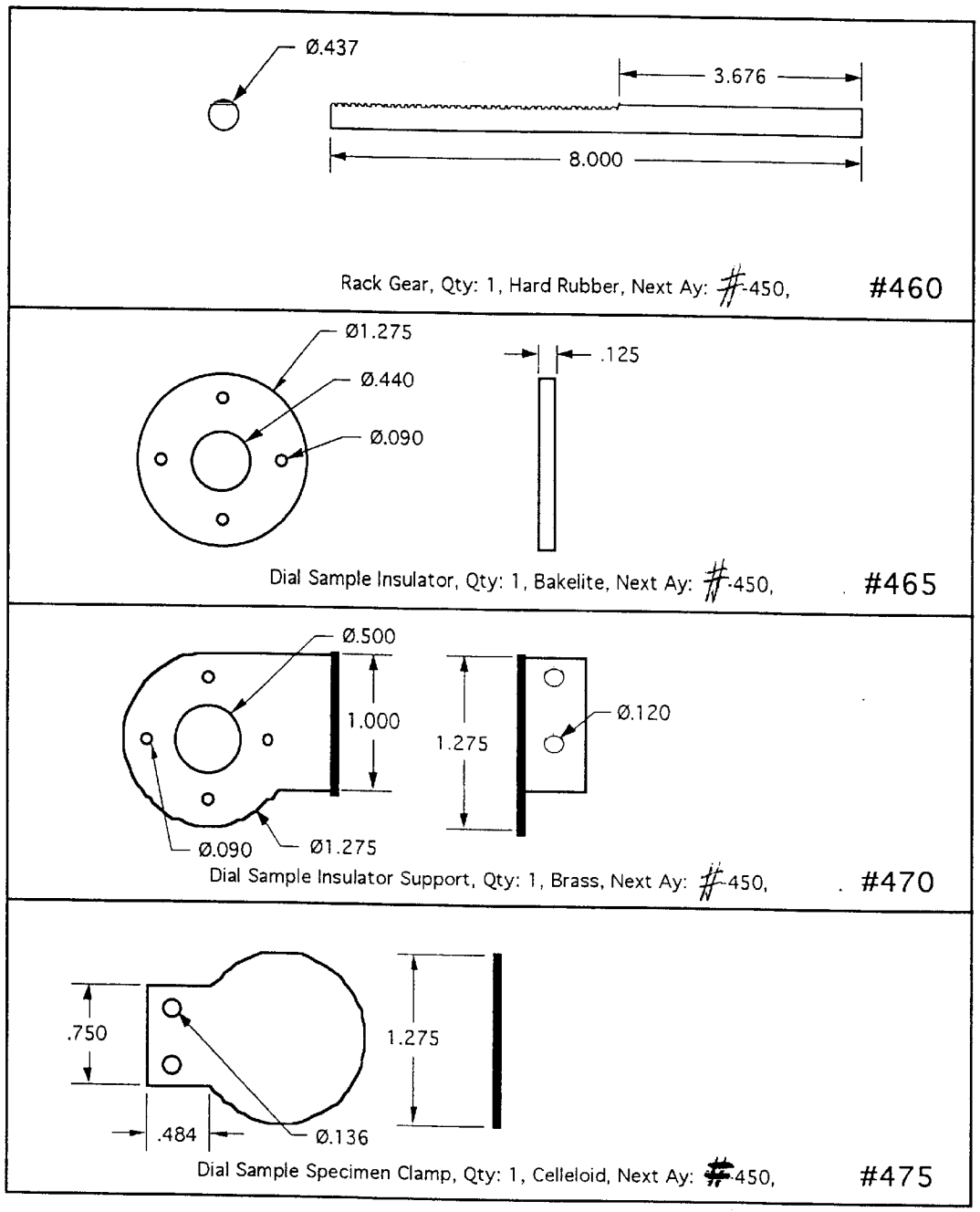
FIG. 65 PART DRAWINGS
1 (at top) THROUGH 4 (at bottom)

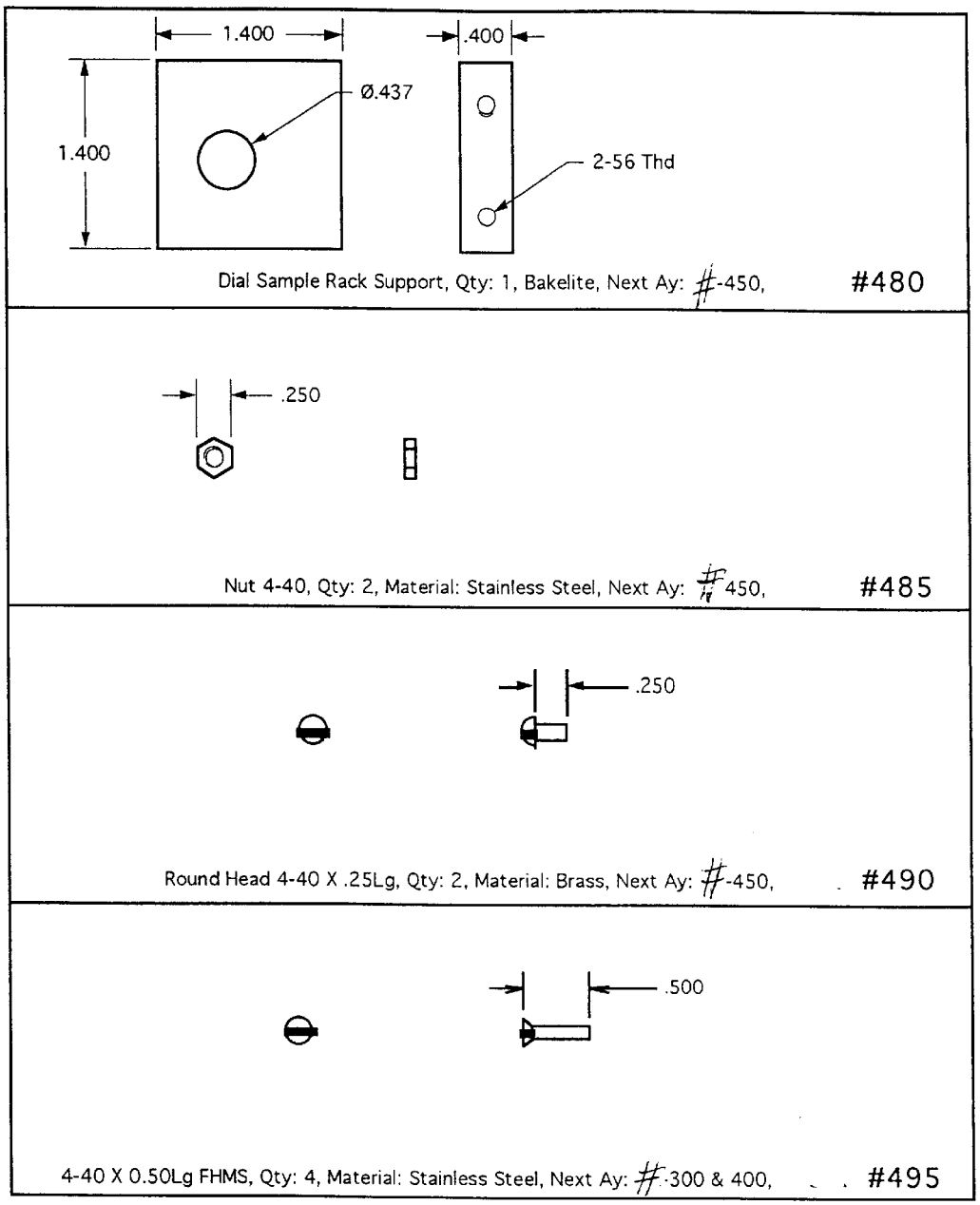
FIG. 66 PART DRAWINGS
1 (at top) THROUGH 4 (at bottom)

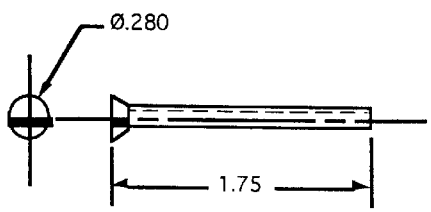
Bolt 6-32 FH Machine Screw, Qty: 1, Material: Stainless Steel, Next Ay: #-500,  #510
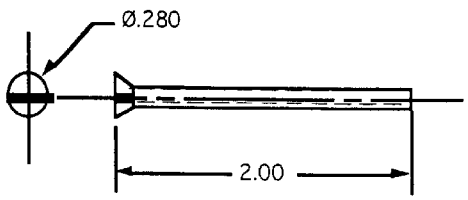
Bolt 6-32 FH Machine Screw, Qty: 1, Material: Stainless Steel, Next Ay: #-500,  #515
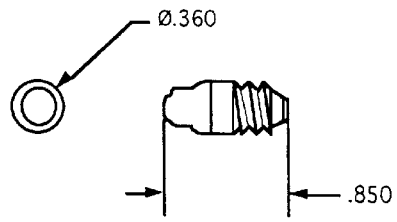
Lamp 2.2 Volt, Qty: 4, Mazda 222, Next Ay: #-500,  #520
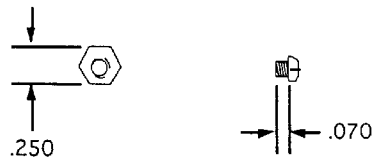
Bolt & Nut 2-56 X .07, Qty: 4, Stainless Steel, Next Ay: #-500,  #525
FIG. 67 PART DRAWINGS
1 (at top) THROUGH 4 (at bottom)

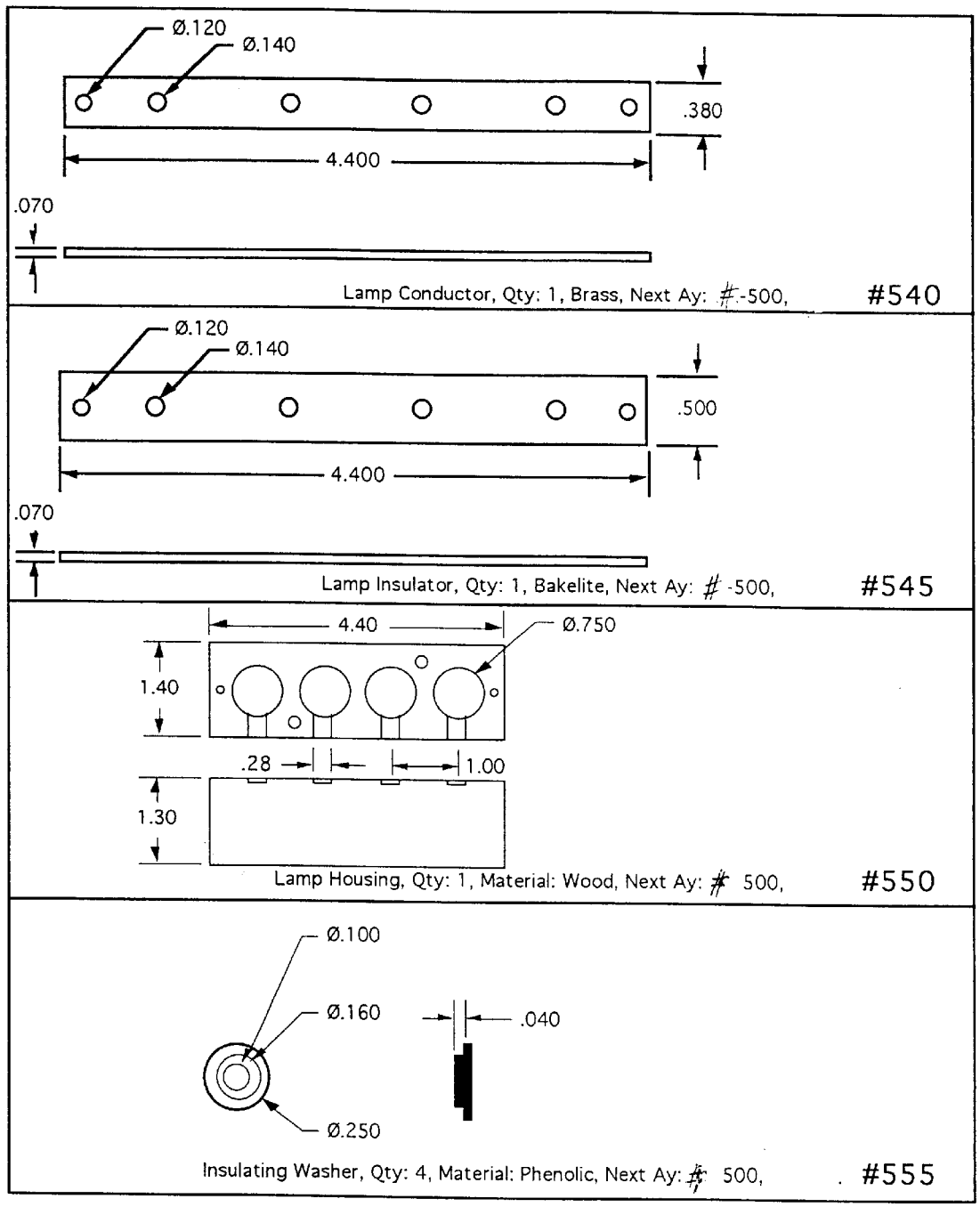
FIG. 68 PART DRAWINGS
1 (at top) THROUGH 4 (at bottom)

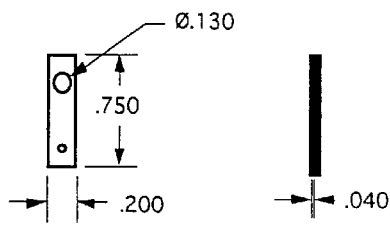
Lamp Lug, Qty: 4, Material: Brass, Next Ay: #-500,    #560
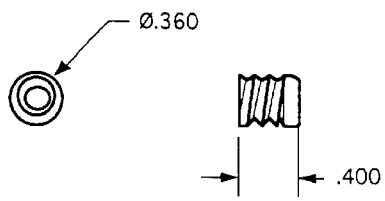
Lamp Socket, Qty: 4, Material: Brass, Next Ay: #-500,    #565
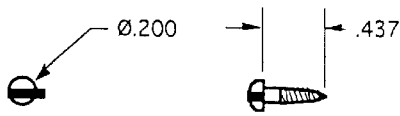
5 Wood Screw, Qty: 2, Material: Brass, Next Ay: # 500,    #570
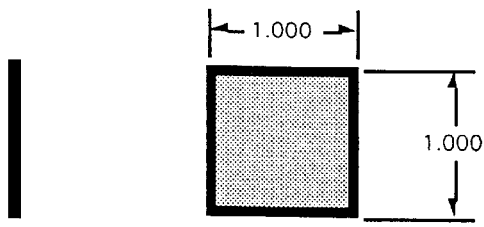
Colored Filter, Qty: 1, Material: 0.038 Thk BLUE Plastic, Next Ay:  -#500,    #575
FIG. 69 PART DRAWINGS
1 (at top) THROUGH 4 (at bottom)

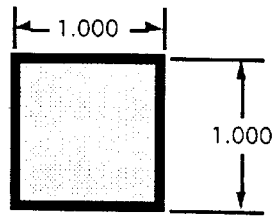
Colored Filter, Qty: 1, Material: 0.038 Thk RED Plastic, Next Ay:  -#500,    #580
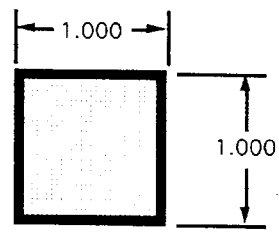
Colored Filter, Qty: 1, Material: 0.038 Thk YELLOW Plastic, Next Ay:  -#500,    #585
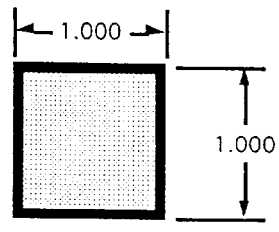
Colored Filter, Qty: 1, Material: 0.038 Thk GREEN Plastic, Next Ay:  #500,    #590
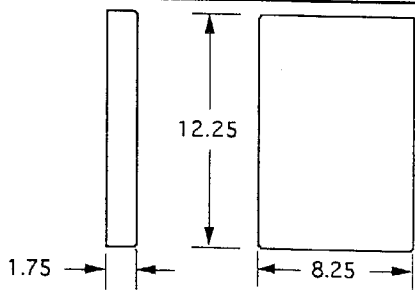
Top Cover, Qty: 1, Material: Wood & Vinyl, Next Ay: #-605,    #610
FIG. 7O PART DRAWINGS
1 (at top) THROUGH 4 (at bottom)

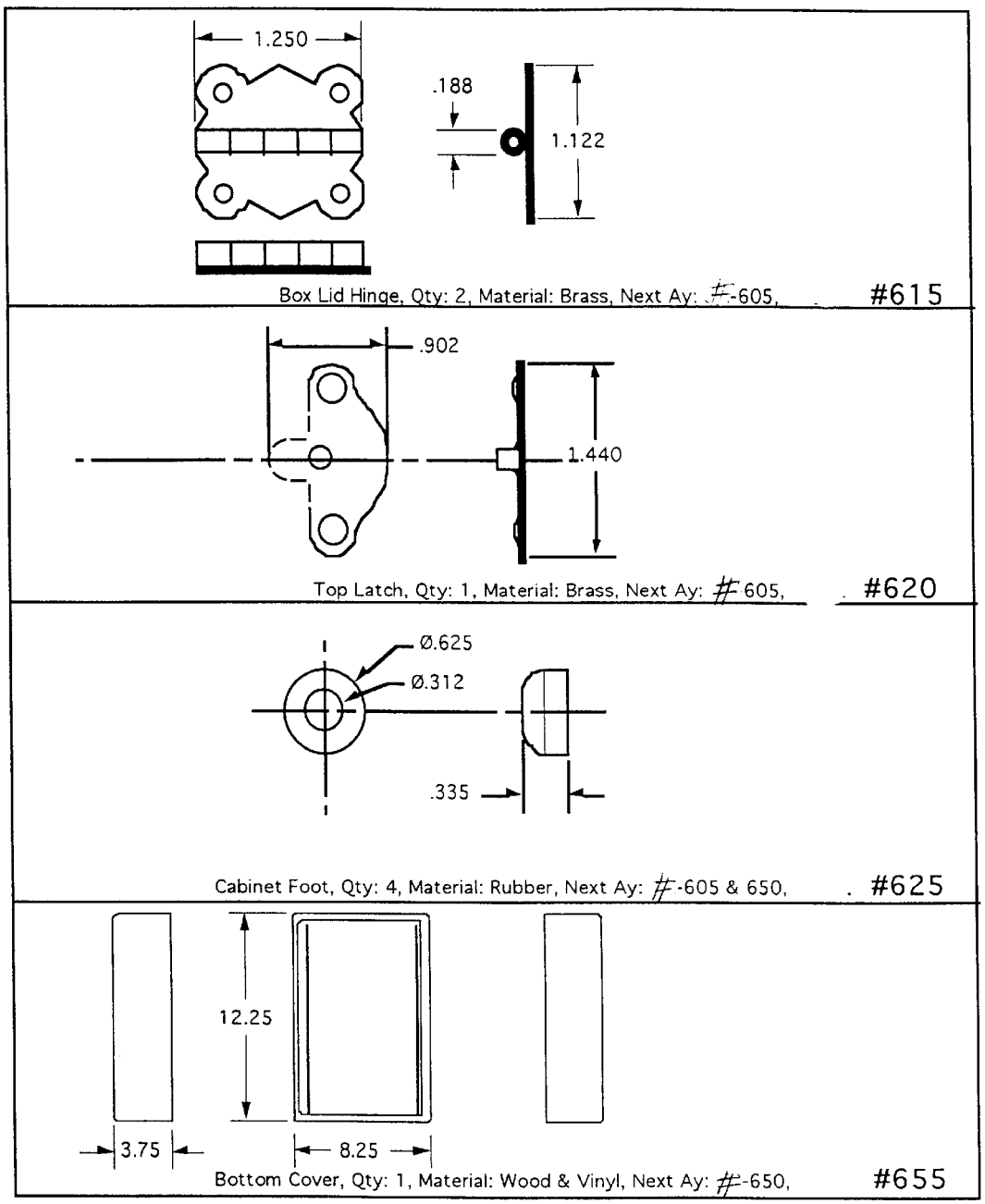
FIG. 7H PART DRAWINGS
1 (at top) THROUGH 4 (at bottom)

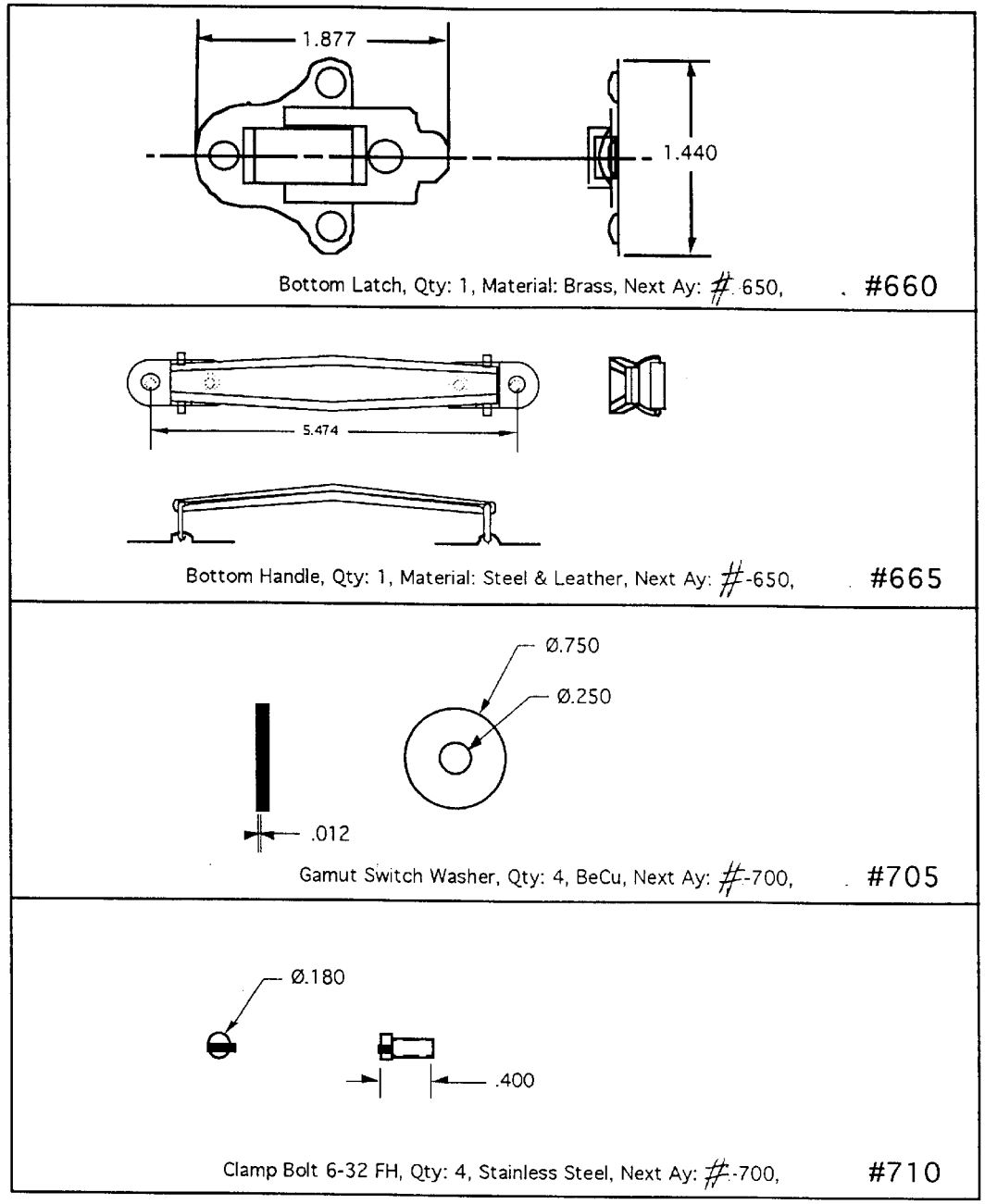
FIG. 72 PART DRAWINGS
1 (at top) THROUGH 4 (at bottom)

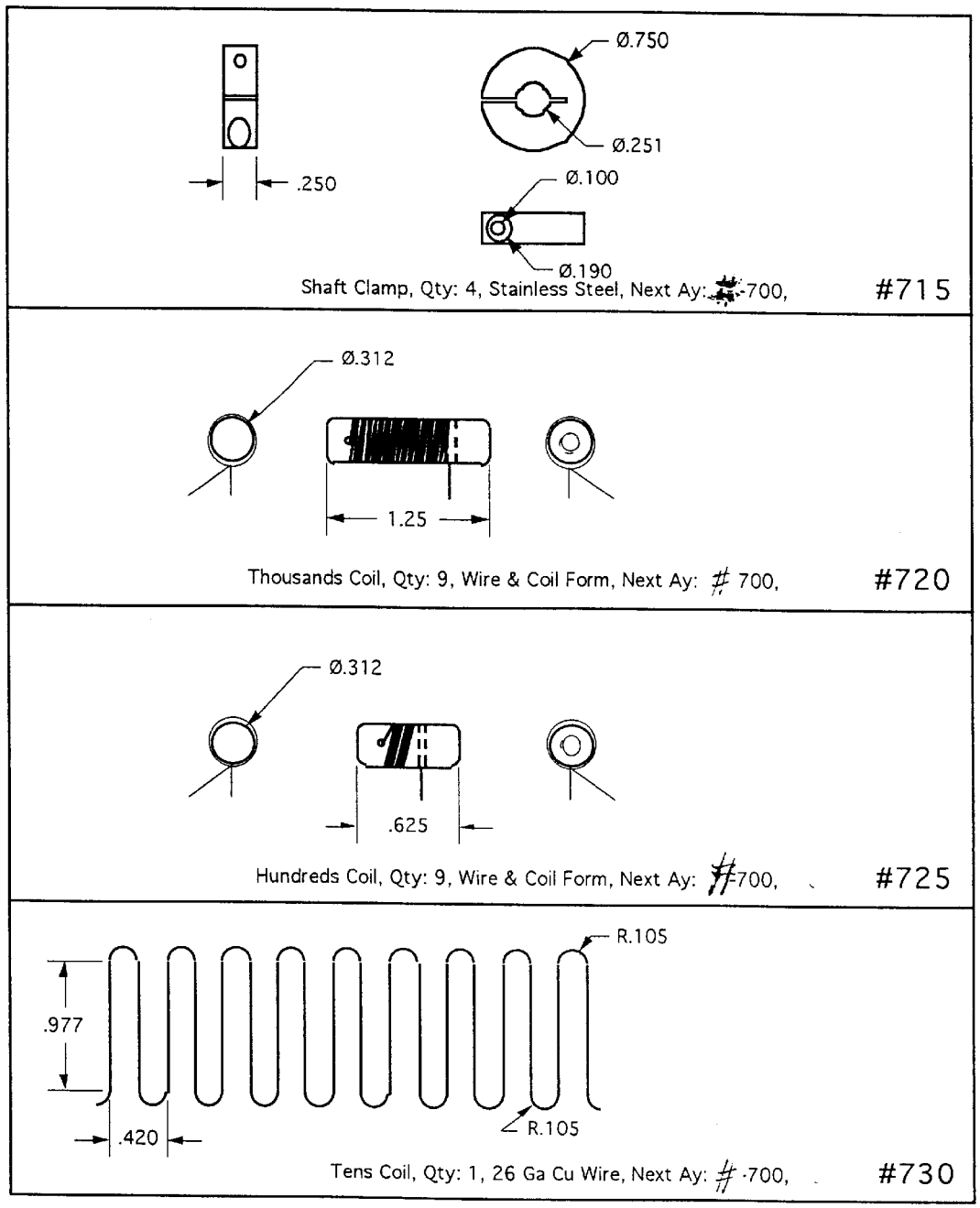
FIG. 73 PART DRAWINGS
1 (at top) THROUGH 4 (at bottom)

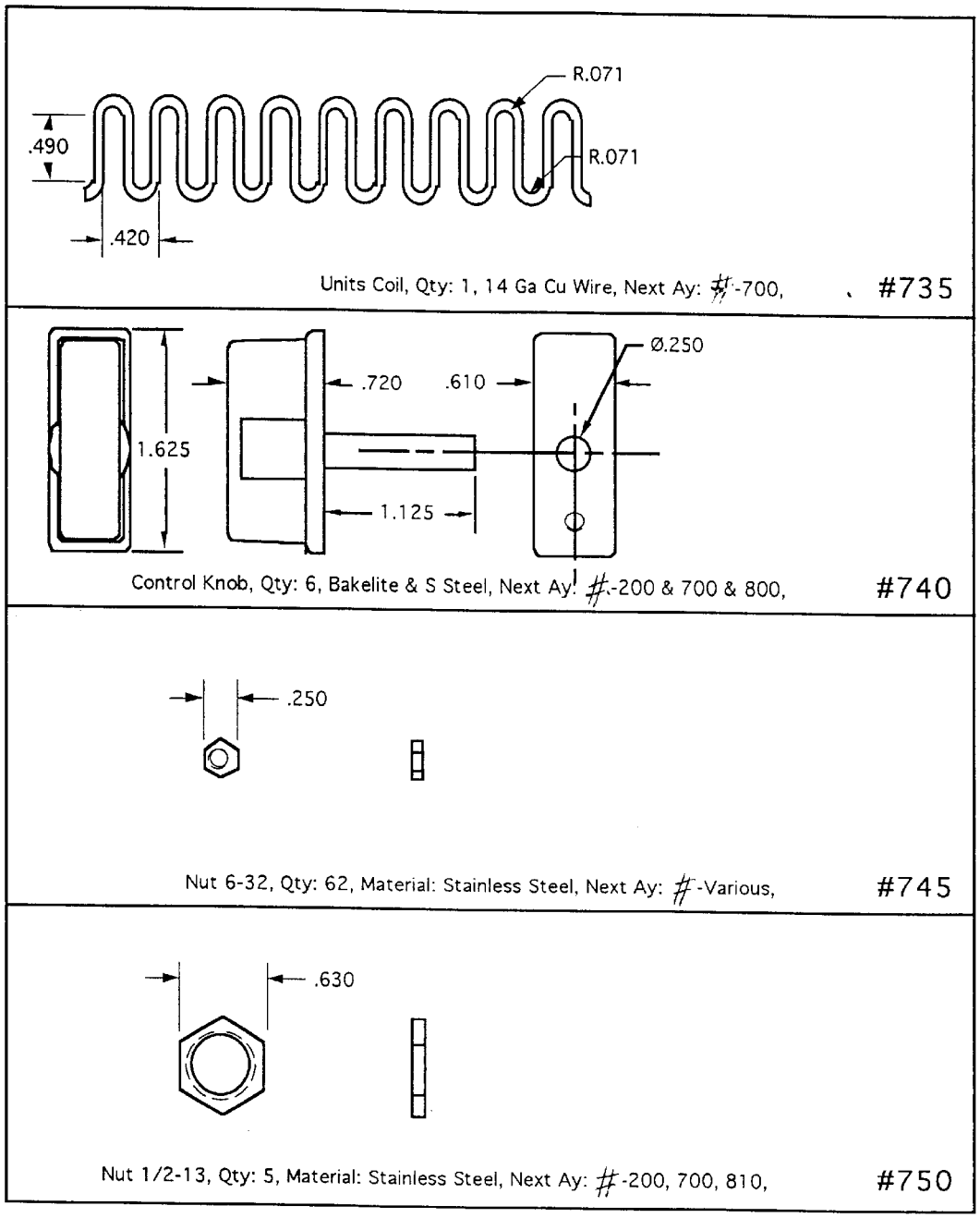
FIG. 74 PART DRAWINGS
1 (at top) THROUGH 4 (at bottom)

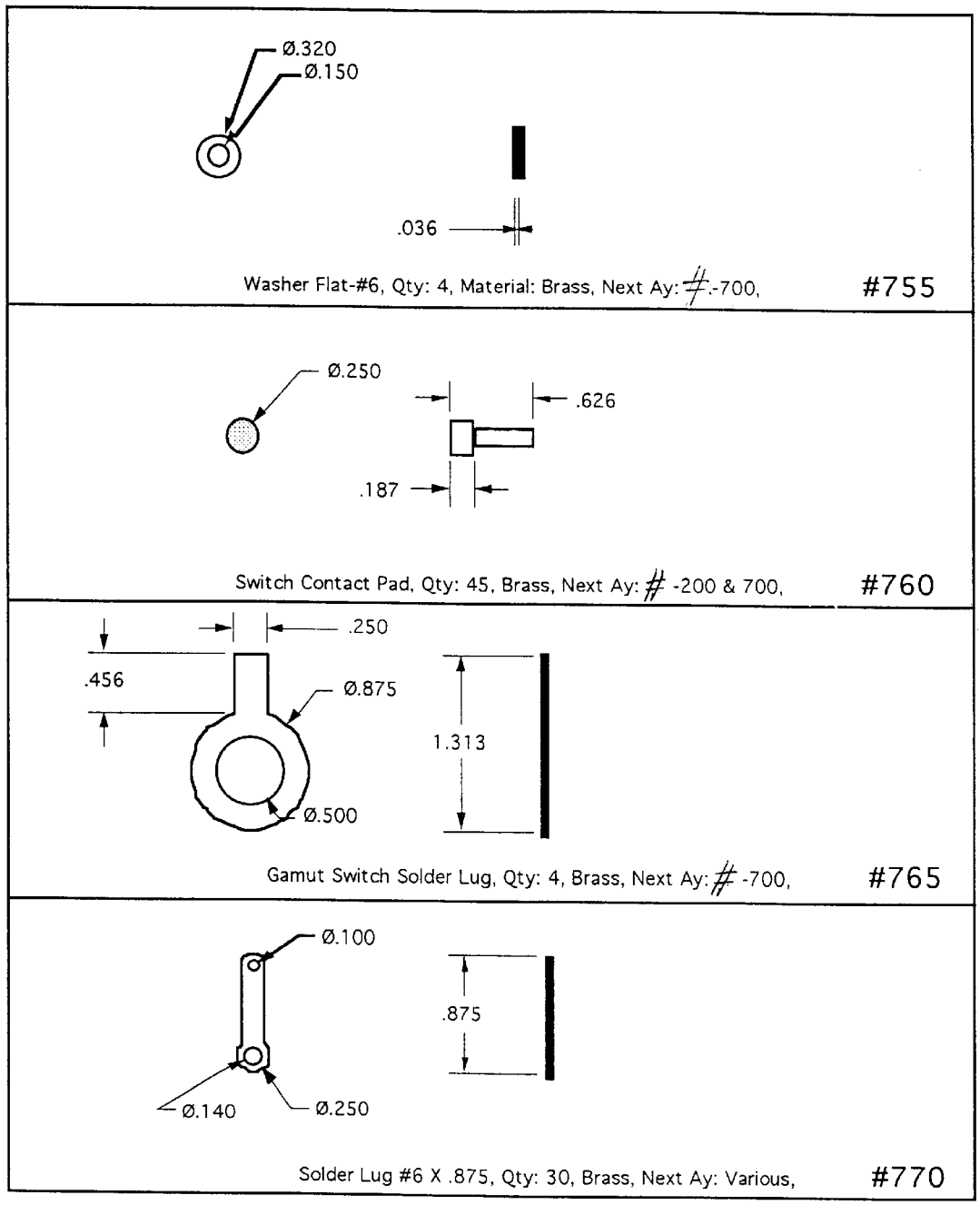
FIG. 75 PART DRAWINGS
1 (at top) THROUGH 4 (at bottom)

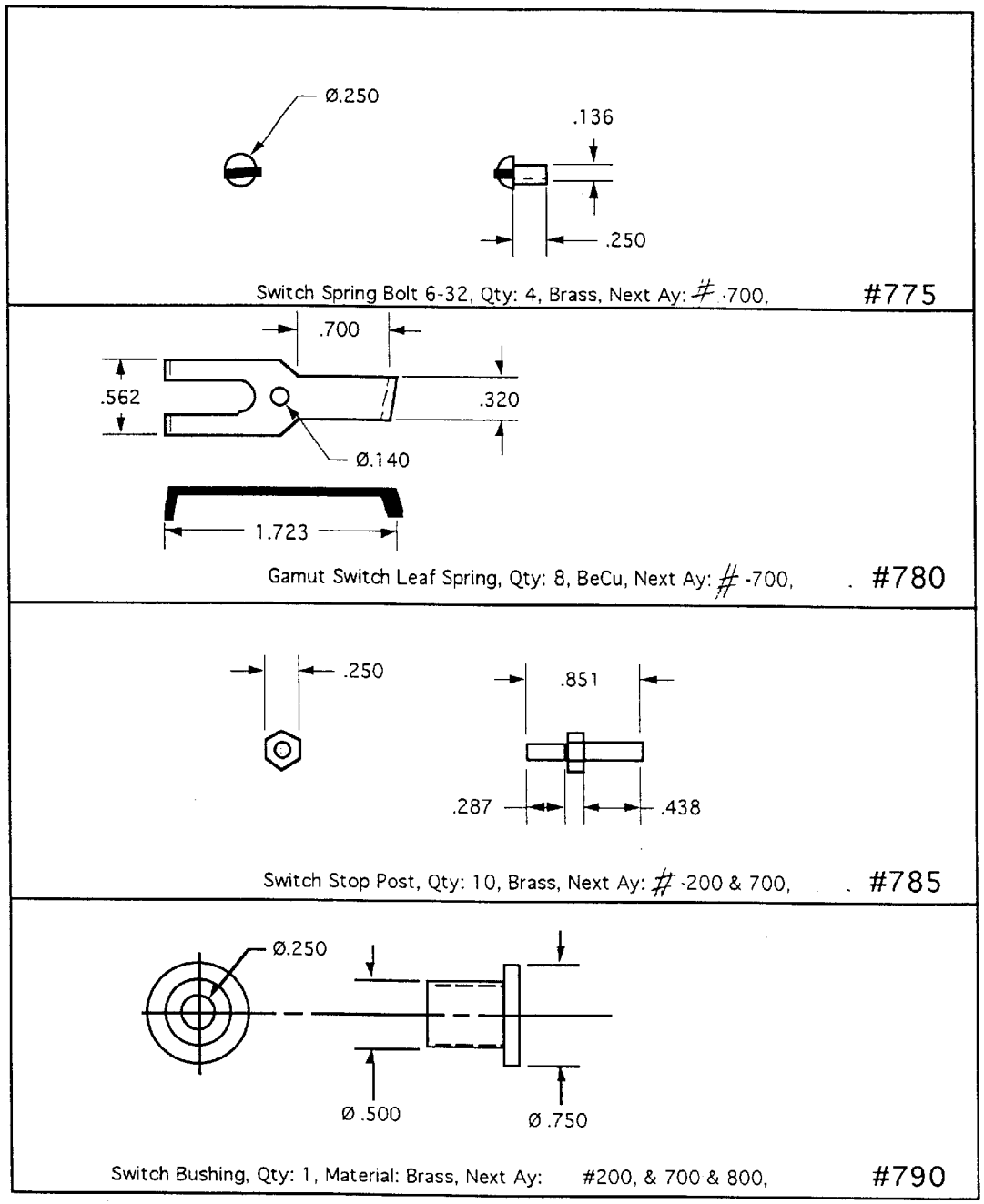
FIG. 76 PART DRAWINGS
1 (at top) THROUGH 4 (at bottom)

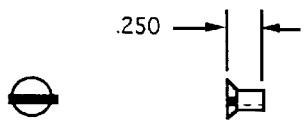
Machine Screw-#6 FH , Qty: 1, Material: Brass, Next Ay: # #800,  #805
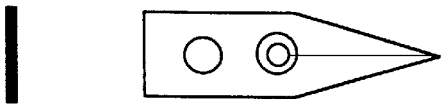
Knob Pointer, Qty: 1, Material: 0.038 Thk Clear Plastic, Next Ay: # #800,  #810
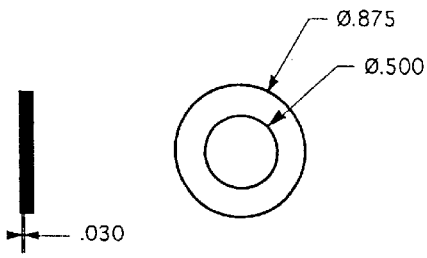
Dial Knob Washer, Qty: 1, Brass, Next Ay: # 800,  #815
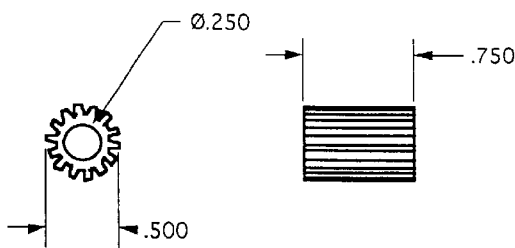
Pinion Gear 14 Tooth, Qty: 1, Brass, Next Ay: # -800,  #820
FIG. 77 PART DRAWINGS
1 (at top) THROUGH 4 (at bottom)

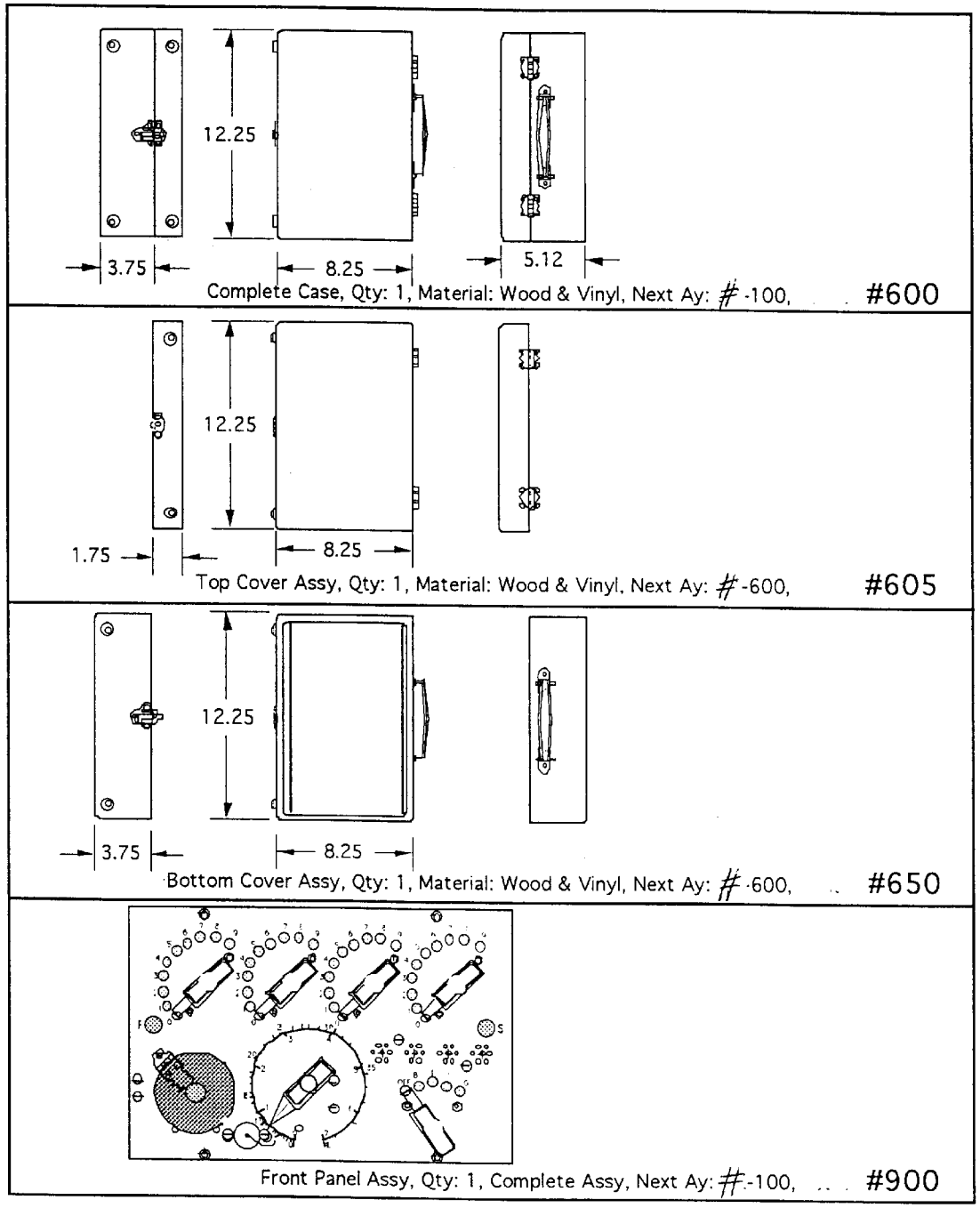
FIG. 78 PART DRAWINGS
1 (at top) THROUGH 4 (at bottom)

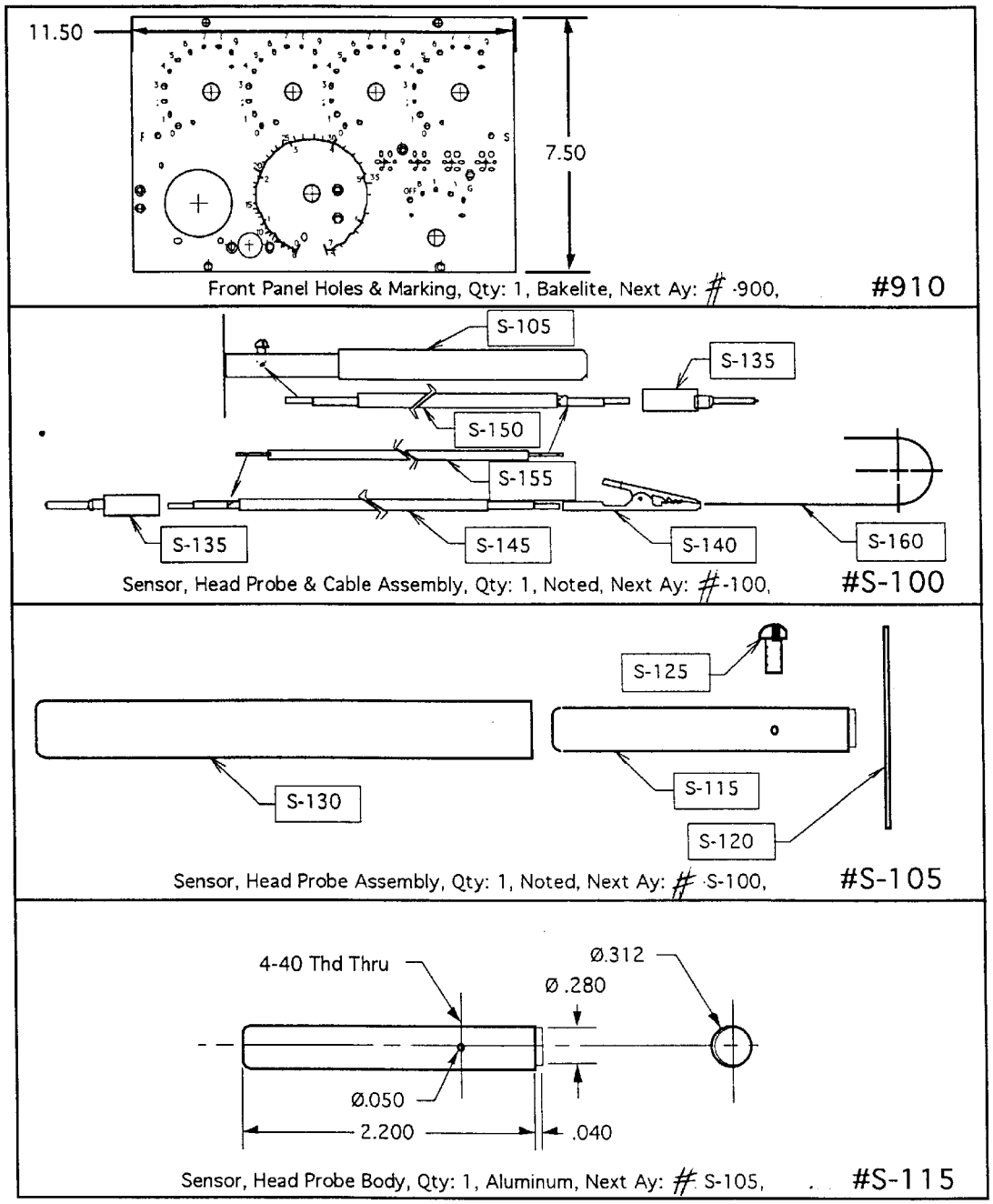
FIG. 79 PART DRAWINGS
1 (at top) THROUGH 4 (at bottom)

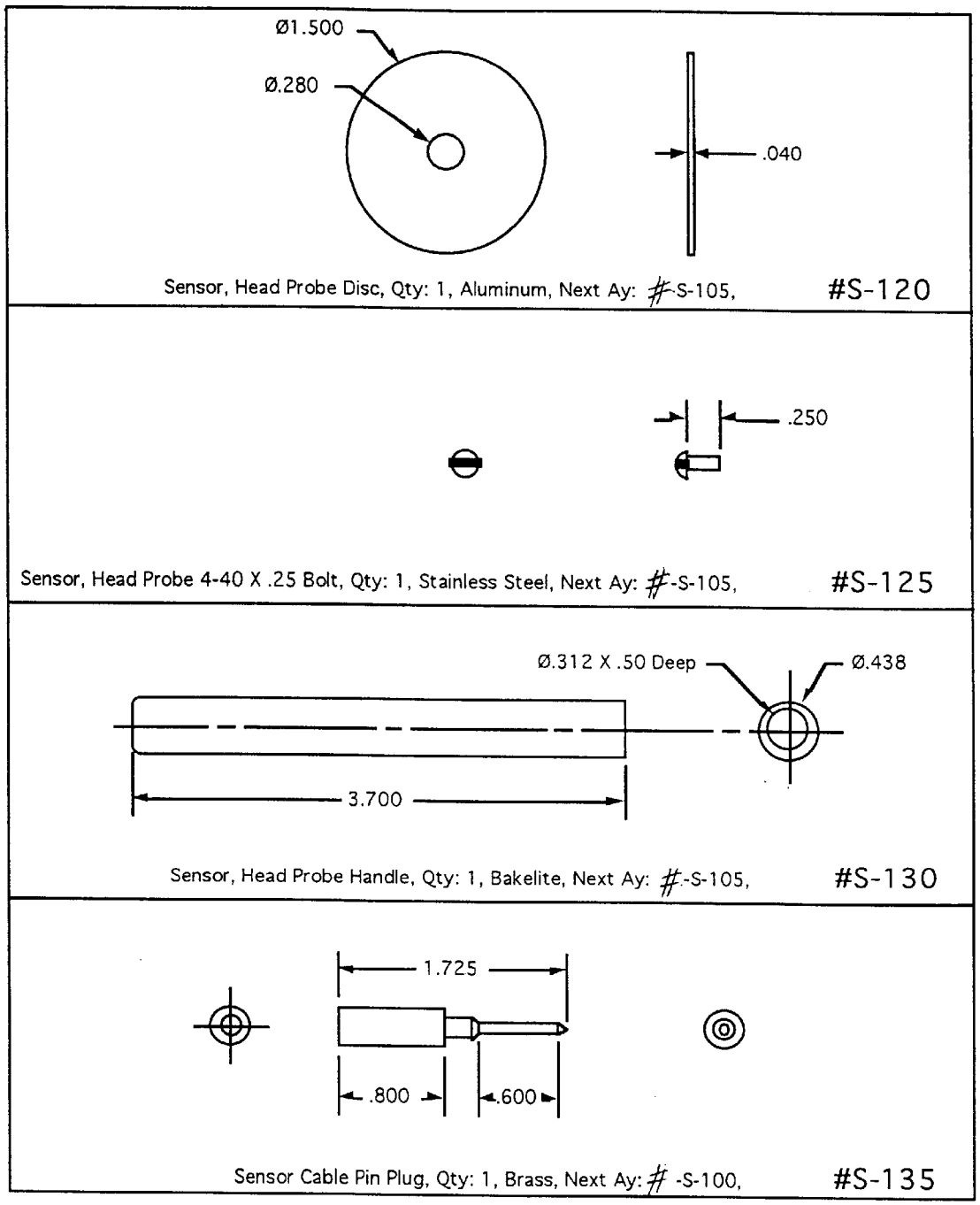
FIG. 80 PART DRAWINGS
1 (at top) THROUGH 4 (at bottom)

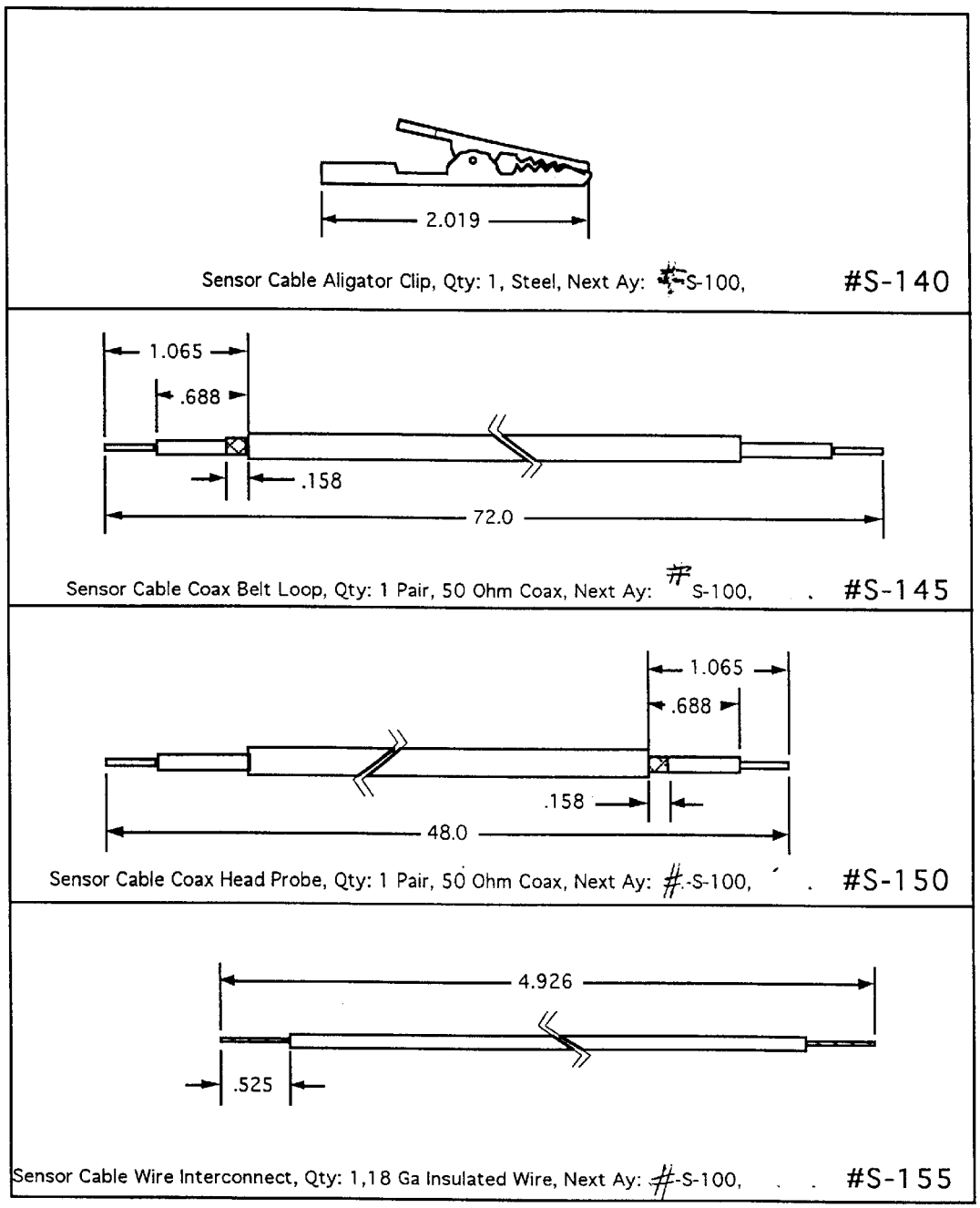
FIG. 81 PART DRAWINGS
1 (at top) THROUGH 4 (at bottom)

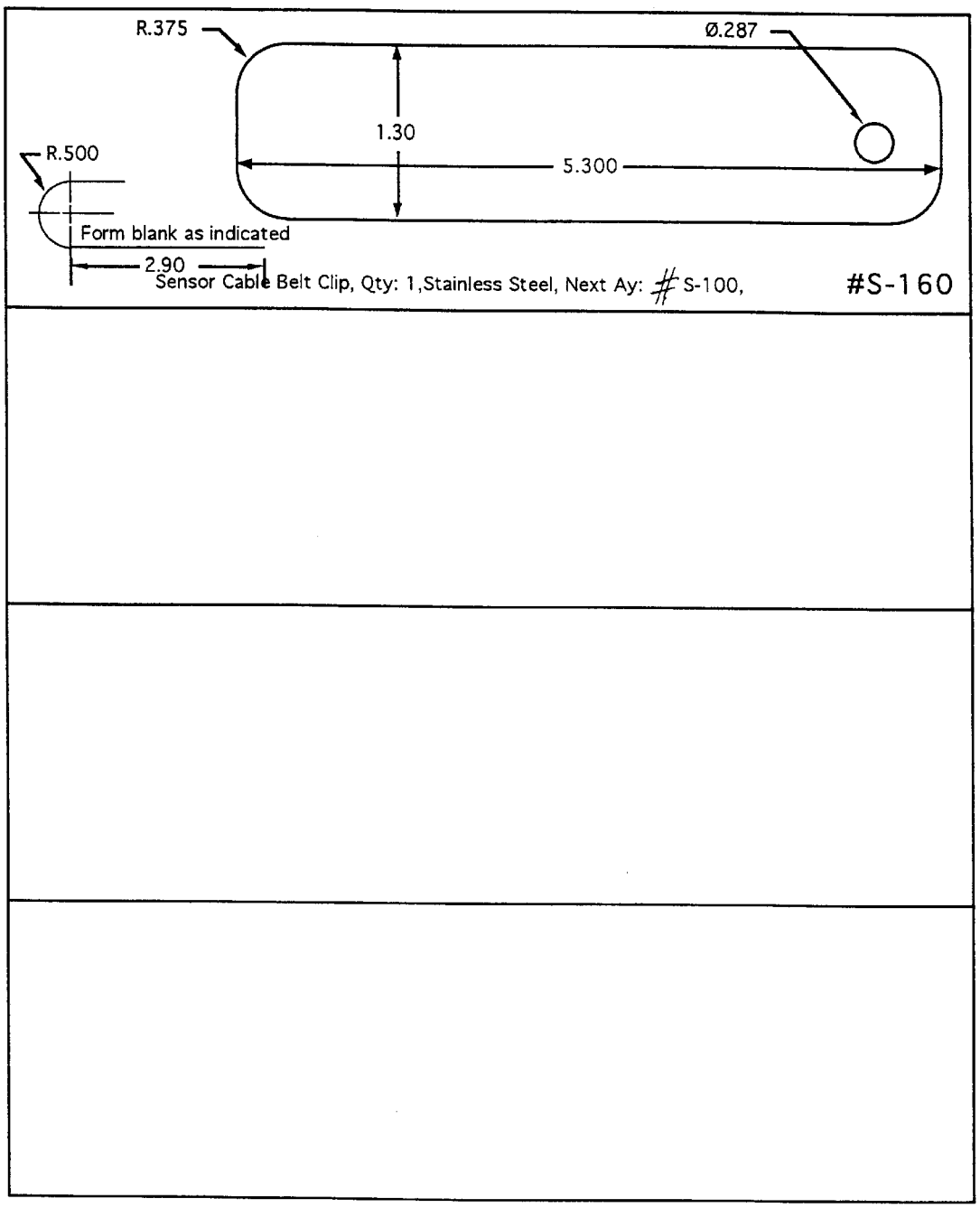
FIG. 82 PART DRAWINGS
1 (at top) THROUGH 4 (at bottom)

THERAPEUTIC AND DIAGNOSTIC APPARATUS AND METHOD

This application is a continuation-in-part of pending U.S. application Ser. No. 09/804,949, filed Mar. 31, 2001, abandoned which is divisional to pending U.S. application Ser. No. 09/141,691, filed Aug. 28, 1998, now issued as U.S. Pat. No. 6,321,120; which is a continuation of international application no. PCT/US97/23845, filed on Dec. 29, 1997; claiming benefit of U.S. provisional application No. 60/034, 561, filed on Dec. 30, 1996 and 60/043,764, filed on Apr. 11, 1997, both of which are DOW abandoned. All of these applications are incorporated herein by reference.

FIELD OF INVENTION

This invention generally relates to apparatus and methods for diagnosing and treating cancer and other illness in humans and animals, and more particularly to a diagnostic method focused on detecting the effect of magnetic fields on blood and tissue samples, and a therapeutic apparatus and method based upon the administration of precisely regulated, low power, pulsed electromagnetic radiation (EMR).

BACKGROUND OF THE INVENTION

There is a considerable body of early literature regarding treatment of various illnesses with radio frequencies (RF) in the 43 MHz range. In U.S. Pat. No. 2,545,087, F. J. Hart disclosed an apparatus for treating a subject with a sequence of radio frequencies in the 43 MHz. range, applied in a stepwise fashion. These frequencies were each modulated sinusoidally at 60 Hz., and further pulsed by a second slow sinusoidal oscillator operating at 90 cycles per minute (1.5 Hz.). The RF frequencies employed by Hart were specified to three decimal places.

The instruments available to Hart and the other researchers of his day were based on tube amplifiers, which resulted in oscillators with considerable drift that could not be precisely tuned. Hart's means for applying the RF energy to a subject most often consisted of a metal plate acting as an antenna. As a result of such oscillator drift and imprecision, and the inefficiency of the available output devices, Hart and his contemporaries were not able to conduct scientific tests with precisely controlled frequencies, or to discover optimal treatment modalities.

Modern electronic technologies make it relatively simple to construct more precise and stable instruments than Hart had at his disposal. As a consequence, it has become possible to study systematically the potential therapeutic value of EMR. The present inventors have undertaken such studies over the course of many years, and as a result have perfected apparatus and methods which have proved effective in treating cancerous tumors in laboratory mice. The inventors believe that the same methods can be effectively adapted for human treatment.

The present inventors have constructed an apparatus designed to overcome the limitations of Hart's approach. They have further sought to establish the utility of their invention through a program of animal testing, and have in turn used the results of such testing to refine the apparatus and the methods for effectively using such apparatus. The resulting apparatus and methods, and the experimental results of applying such apparatus and methods to treat cancerous tumors in mice, will be described below.

Diagnostic elements of the invention are used in conjunction with the therapeutic elements. Development of the diagnostic elements of this invention utilized an apparatus originally developed by Dr. Albert Abrams who was born in San Francisco in 1863. Abrams got his medical degree from the reputed German University of Heidelberg at the age of 19. He received another degree from the Cooper Medical School (later incorporated into the Stanford Medical School) in the San Francisco Bay Area.

One of Dr. Albert Abrams inventions was the Radioscope which was used for diagnosis. This diagnosis and treatment, to date, has come about in several progressive steps. First, Abrams found that when a cancer patient faced west, percussion revealed a dullness on the patient's abdomen. Second, when a piece of cancer tissue was held close to the forehead of a healthy person, whom Abrams called the "reagent," percussion revealed the same dullness on the reagent's abdomen. Third, the energy radiated from the cancerous tissue could be conducted over a wire to the reagent and produce the same dullness as when the tissue was held to the forehead of the reagent. Fourth, by the same procedure not only cancer, but other diseases, could be detected by the energy radiated from the patient, or from a sample of the patient's blood.

It would seem obvious from Abrams' discoveries that disease could be identified by simply tuning in on the frequency that moved along the wire from the sample to the reagent's forehead. His first diagnosis device was made with wire-wound rheostats which when set at 30 and 50 ohms, Abrams said he found the "vibration rates" of carcinoma because the dullness then occurred on the abdomen of the reagent. It seems strange now but at that time Abrams thought he was dealing with resistance. But identification of "vibrations" in terms of ohms of resistance on its face makes no electronic sense at all. And so it is not surprising that medical science at once branded Abrams as a fake without any investigation to see if perchance, the rheostats could have been inductively wound so that the settings of 30 and 50 could have fortuitously turned in on the frequency radiated by cancer. At that time electronic science had not developed enough to accept any such explanation of the Abrams' phenomenon.

A Canadian doctor, T. Proctor Hall, was curious enough to attend an Abrams seminar demonstration. Hall was so thoroughly convinced by what he saw that he read a paper before the British Columbia Academy of Science on Apr. 27, 1923 in which he reported that Abrams' diagnosis and treatment really did work, although, "it seems ridiculously simple".

A few years before Dr. Abrams passed away in 1924 he founded the Electronic Medical Foundation in San Francisco. Dr. Thomas Colson, B.S., L.L.B., D.O. was the one at the Foundation who developed and made practicable many of Abrams' procedures.

In 1953 The Foundation published a booklet entitled MOLECULAR RADIATIONS by Thomas Colson, Editor, Journal of Electronic Medicine, 1928–1946. Fred Hart assisted in preparation of the booklet for publication. In the booklet Colson explains why the Abrams' procedure permits functions and diseases of the body to be discovered in the molecules (which are present in the blood) before the cells of the body are effected. Colson also contributed to and reported on the development of the "Radioscope" which has a circuit designed after a radio receiver but which has no detector of its own but instead gets reactions from the reflexes on the abdomen of the reagent.

Fred Hart continued with the work of Abrams and Colson. Many tests were performed using the Radioscope to diagnose the bloods of both humans and animals. From about 1953 to present more tests and experiments were performed by Fred Hart's daughter using the Radioscope for blood analysis and diagnosis. Her research into the use of the Radioscope has proven to be successful, tests are repeatable, and her analysis of ailments to be accurate. She has perfected the procedures required for repeatable results and wishes to make her finding public for the benefit of mankind.

SUMMARY OF THE INVENTION

It is generally the object of the present invention to provide a method for diagnosis and treatment of cancer and other illnesses using a Radioscope to diagnose the illness, a Therapeutic Apparatus to treat the illness, and a Radioscope to monitor the treatment such that the treatment can be modified as necessary.

It is also generally the object of the present invention to utilize electromagnetic radiation to provide effective treatments for cancer and other illnesses.

It is a further object of this invention to achieve reliable and reproducible therapeutic results from EMR treatment methods by achieving precise control over the treatment frequency.

It is also an object of the present invention to provide an efficient means of transmitting EMR from the generating means to the subject.

It is another object of the present invention to provide an EMR treatment that may be applied at very low power levels that can cause no harm.

These and other objects are achieved in accordance with the present invention through the use of a Radioscope for diagnosis, and a Therapeutic Apparatus for treatment.

The Therapeutic Apparatus is an apparatus involving an oscillator that outputs, at a power of less than one mw, an RF frequency in the 43 MHz range, regulated and stabilized to the fifth or sixth decimal place, which is in turn modulated with a 60 Hz. 50% duty cycle square wave, which is in turn gated, again on a 50% duty cycle, at a rate of 1.167 Hz. (70 pulses per minute).

The RF frequency is chosen for a particular subject based on the believed effectiveness of the frequency in treating the illness in question, as summarized herein.

The modulated RF signal output by the apparatus of the present invention is applied to a flat loop of wire approximately 60 cm. long, grounded at one end and wound in five flat, concentric spiral-rectangular turns spaced about 3.175 mm. apart, the loop (herein referred to as a "treatment loop") being mounted on an insulating layer adhesively bonded to a metal plate.

In using this apparatus, the metal plate is placed, loop down, on the subject's body near the area to be treated. RF power is applied to the loop at one precise treatment RF frequency for at least one hour at a time. During treatment, the treatment loop is shielded from direct light and moving air currents.

There are alternative embodiments of the invention that differ somewhat in their circuit and construction details. The first, referred to as the "Battery SCPO," is a battery-powered "Single Crystal Pulsed Oscillator" in a metal housing with an internal quartz crystal, and an integral, externally mounted treatment loop. Each Battery SCPO is limited to a single frequency. A variation is shown (the "Mouse SCPO") in which an SCPO is powered by an external DC power module rather than batteries. An alternate embodiment, referred to as the "Generator Embodiment", derives its treatment signal from the modulated output of a Hewlett-Packard Model 8662A frequency generator, and supplies the signal to the treatment loop over a short coaxial cable. The frequency and power of the Generator Embodiment is easily adjusted with controls on the front panel of the 8662A frequency generator. Another alternative embodiment, also based on the HP 8662A Frequency Generator, modulates the RF signal entirely externally to the HP 8662A, and employs a specific type of coaxial cable to carry the signal from the modulator to the treatment loop. These alternative embodiments differ somewhat in their circuitry and construction details, as will be more fully described below.

In any of the alternative embodiments, treatment is non-restrictive and utilizes a low power believed to be completely safe for humans.

The diagnostic and other objects of this invention are achieved through the use, as outlined below, of a diagnostic apparatus called the "Radioscope." The Radioscope has a receptacle for a blood sample. Its dial settings tunes in frequencies of the energy radiated from the blood sample. Another dial determines the strength of the radiated energy. Each such disease frequency as it is tuned in is separately transmitted to the forehead of the reagent. When the dullness occurs on the reagent's abdomen (when being percussed), it indicates the presence, in the blood sample, of the disease entity to which that particular frequency belongs.

The Radioscope is connected to the reagent by two wires, one to a hand-held sensor touching the forehead or top of the head, and the other wire to a metal "U" shaped loop that hangs on the reagent's belt. The reagent's abdomen is exposed for stroking with a Lucite rod by the operator. The operator obtains a "stick" if the patient has a disease determined by the dial settings. The settings of the Radioscope and the sensor and stroking locations are found in a table called "The Gamut," which has been developed over thousands of tests and many years of trial and error experimentation.

Some Electromagnetic Phenomenons:

The orientation of the Radioscope is positioned so that the movable sample axis is on a North-West line, that is, the axis of the large sample strap (# 350) is on a North-South line. The reagent faces West.

While the reagent faces West, reflexes on the abdomen of the reagent will detect the radiations from the blood sample as they are tuned in by the Radioscope and transmitted by wire from the Radioscope to a particular spot on the forehead of the reagent.

But, if the reagent turns slightly to the South, or slightly to the North, reflex detection stops. Reflex detection is manifested by a peculiar kind of difference in magnetic potential. This difference in potential occurs between the area of reflex and what touches it during the stroking process by the operator of the Radioscope. This difference is manifested by a stick or grab between the skin of the reflex area and the stroking instrument being used by the operator. (The adherence is similar to a nail being drawn to a magnet.)

The operator's stroking instrument could be
1. Fingers of the operator's right hand
2. A glass rod, plastic rod or copper spoon held in the operator's right hand
3. Or the North pole of a bar magnet.

But the "stick or grab" is squelched when that stroked area on the skin is touched by:
1. Forefingers of the operator's left hand
2. The South Pole of a bar magnet.

Thus both the Radioscope (which is simply the tuning device) and the reagent's reflex (which is simply the detector) as well as the blood sample (which is the source of the radiations) are all activated (if not energized) by the earth's magnetic field. Moreover, the Radioscope diagnosis must be conducted in a room very dimly lighted because bright light on the blood (or on the Radioscope circuit) squelches the radiations.

Other features and advantages of the present invention will become apparent from the following more detailed description, taken in conjunction with the accompanying drawings, which illustrate, by way of example, the principles of the invention.

BRIEF DESCRIPTION OF THE DRAWINGS
Figure Listing:

FIGS. 9A1–9J4 show the treatment housings and treatment loops used for treating mice in the experiments described herein.

FIG. 38 shows the Radioscope front panel.

FIG. 42 shows the complete case assembly with reference numbers.

FIG. 43 shows the top cover assembly with reference numbers.

FIG. 44 shows the bottom cover assembly with reference numbers.

FIG. 45 shows the front panel assembly with reference numbers.

FIG. 46 shows the front panel holes and marking with dimensions.

FIG. 47 shows the binding post and lamp switch assembly with reference numbers.

FIG. 48 shows the large sample assembly with reference numbers.

FIG. 49 shows the small sample assembly with reference numbers.

FIG. 50 shows the dial sample assembly with reference numbers.

FIG. 51 shows the lamp housing assembly with reference numbers.

FIG. 52 shows the gamut coil assemblies with reference numbers.

FIG. 53 shows the gamut switch assembly with reference numbers.

FIG. 54 shows the dial knob assembly with reference numbers.

FIG. 55 shows the battery clamp and nut assembly with reference numbers.

FIG. 56 shows the coil wiring details.

FIG. 57 shows the position of fingers for localizing.

FIG. 58 shows the sensor locations and stroke areas on reagents abdomen.

FIG. 59 shows detailed drawings of parts # 110, 115, 120, 125.

FIG. 60 shows detailed drawings of parts # 130, 135, 210, 215.

FIG. 61 shows detailed drawings of parts # 220, 225, 310, 315.

FIG. 62 shows detailed drawings of parts # 320, 325, 330, 335.

FIG. 63 shows detailed drawings of parts # 340, 345, 350, 410.

FIG. 64 shows detailed drawings of parts # 415, 420, 430, 455.

FIG. 65 shows detailed drawings of parts # 460, 465, 470, 475.

FIG. 66 shows detailed drawings of parts # 480, 485, 490, 495.

FIG. 67 shows detailed drawings of parts # 510, 515, 420, 525.

FIG. 68 shows detailed drawings of parts # 540, 545, 550, 555.

FIG. 69 shows detailed drawings of parts # 560, 565, 570, 575.

FIG. 70 shows detailed drawings of parts # 580, 585, 590, 610.

FIG. 71 shows detailed drawings of parts # 615, 620, 625, 655.

FIG. 72 shows detailed drawings of parts # 660, 665, 705, 710.

FIG. 73 shows detailed drawings of parts # 715, 720, 725, 730.

FIG. 74 shows detailed drawings of parts # 735, 740, 745, 750.

FIG. 75 shows detailed drawings of parts # 755, 760, 765, 770.

FIG. 76 shows detailed drawings of parts # 775, 780, 785, 790.

FIG. 77 shows detailed drawings of parts # 805, 810, 815, 820.

FIG. 78 shows detailed drawings of parts # 600, 605, 650, 900.

FIG. 79 shows detailed drawings of parts # 910, S-100, S-105, S-115.

FIG. 80 shows detailed drawings of parts # -120, S-125, S-130, S-135.

FIG. 81 shows detailed drawings of parts # -140, S-145, S-150, S-155.

FIG. 82 shows detailed drawings of parts # S-160.

Figure 1B:
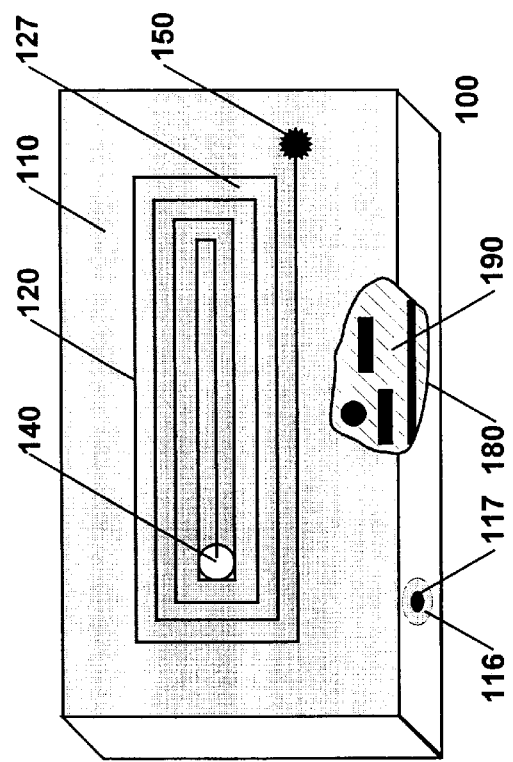
FIGS. 1A and 1B show top and bottom external views of the Battery SCPO.

Table Listing:

TABLE 1 shows treatment frequencies.
TABLE 2 shows exemplary crystal measurements.
TABLE 3 shows a parts list for Battery SCPO.
TABLE 4 shows a parts list for generator embodiment.
TABLE 4A shows an additional part for externally pulsed generator embodiment.
TABLE 5 shows the treatment summary for OUJ-456.
TABLE 6 shows the treatment summary for OUJ-470.
TABLE 7 shows the treatment summary for OUJ-471.
TABLE 8 shows the treatment summary for OUJ-473.
TABLE 9 shows the treatment summary for OUJ-475.
TABLE 10 shows the treatment summary for OUJ-496.
TABLE 11 shows the treatment summary for OUJ-506.
TABLE 12 shows the treatment summary for OUJ-516.
TABLE 13 shows the treatment summary for OUJ-526.
TABLE 14 shows the treatment summary for OUJ-650.
TABLE 15 shows the summary for A-486.
TABLE 16 shows the summary for A-488.
TABLE 17 shows the summary for A-490.
TABLE 18 shows the summary for A-492.
TABLE 19 shows the summary for A-500.
TABLE 20 shows the summary for A-538.
TABLE 21 shows the summary for A-540.
TABLE 22 shows the summary for A-542.
TABLE 23 shows the summary for A-592.
TABLE 24 shows the summary for A-594.
TABLE 25 shows the days of life, measurement, and number of tumors for treated mice.
TABLE 26 shows the data regarding tumors that disappeared.
TABLE 27 shows the comparative weight changes between the control mice and the treated mice.
TABLE 28A shows a comparison of maxim um tumor size for the treated mice.
TABLE 28B shows a comparison of maximum tumor size for the control mice.
TABLE 29 shows the disappearance of tumors on mice treated with HP 8662A Frequency Generator Embodiment.
TABLE 30 shows a complete parts list for the Radioscope.
TABLE 31 shows the gamut table.

DETAILED DESCRIPTION OF THE PREFERRED EMBODIMENTS

I. Preferred Embodiments for the Therapeutic Elements of the Present Invention:

1. Design Considerations

According to experiments conducted by the present inventors, treatment with EMR is most effective under the following conditions:

a) The treatment frequency is selected with a precision extending to the fifth or sixth decimal point, or at least one half part per million.

b) The frequency is extremely stable over the course of the treatment.

c) The precise frequency chosen is held at that frequency and applied without variation for at least one hour.

d) RF power applied to the subject is held to less than one milliwatt (mW).

e) The EMR is applied through a coiled loop of wire, which, for treatments in the 43 MHz. Range, is approximately 60 cm. long.

The frequencies listed in Table 1 are believed to be effective for treating the indicated maladies:

TABLE 1

| Treatment Frequencies | |
|---|---|
| Frequency | Malady |
| 43,322,480 | Sarcoma (generalized) |
| 43,322,492 | Sarcoma (intestines) |
| 43,322,485 | Sarcoma (breast) |
| 43,346,000 | Tuberculosis (general) |
| 43,346,090 | Tuberculosis (intestines) |
| 43,346,000 | Tuberculosis (breast) |
| 43,346,050 | Common cold |
| 43,353,800 | Carcinoma (general) |
| 43,353,800 | Carcinoma (intestines) |
| 43,353,850 | Carcinoma (breast) |
| 43,353,800 | Malignancy |
| 43,296,000 | Strep |
| 43,351,830 | Treats several diseases |
| 43,351,850 | Treats several diseases |
| 43,351,855 | Treats several diseases |
| 43,351,870 | Treats several diseases |
| 43,352,000 | Pneumonia |
| 43,245,000 | Staph |

The foregoing list includes all of the frequencies studied by the present inventors and found to be effective. The inventors believe that different frequencies, even close to the above-stated frequencies are not effective. They have found that the effectiveness of the treatment depends critically on the precise frequency chosen, to the precision indicated herein. They have also found that steady treatment frequencies are more effective than swept or varied frequencies.

This invention is not intended to be limited to the frequencies stated in the above table. The inventors believe that there may be other frequencies in the 43 MHz. range that the present inventors have not as yet studied, that may also be effective. Similarly, the present inventors believe that there may be effective treatment frequencies in completely different ranges, for example, at much higher frequencies. The most important factor, in the view of the present inventors, is a precisely chosen frequency steadily applied for at least an hour at a time.

2. Construction of Alternative Treatment Devices

For twenty years we have been working to obtain the correct frequencies with which to treat the mice and also the best possible instrument (method) with which to deliver the treatment to the mouse. Some of our experiments included using two plates (a hot and ground) rather than the treatment loop. All things considered, we feel the embodiments employing treatment loop electrodes have performed the best in our experiments on the mice.

Detailed descriptions of the alternate embodiments of the invention are set forth here to demonstrate that the principles taught in this invention are readily reducible to practice. It should be understood that these embodiments represent but a few of the possible configurations of the present invention, and that, utilizing the principles of the present invention as disclosed herein, analogous apparatus and methods may be readily devised for controlled therapeutic application of RF energy.

A. Battery SCPO

Figure 1A:
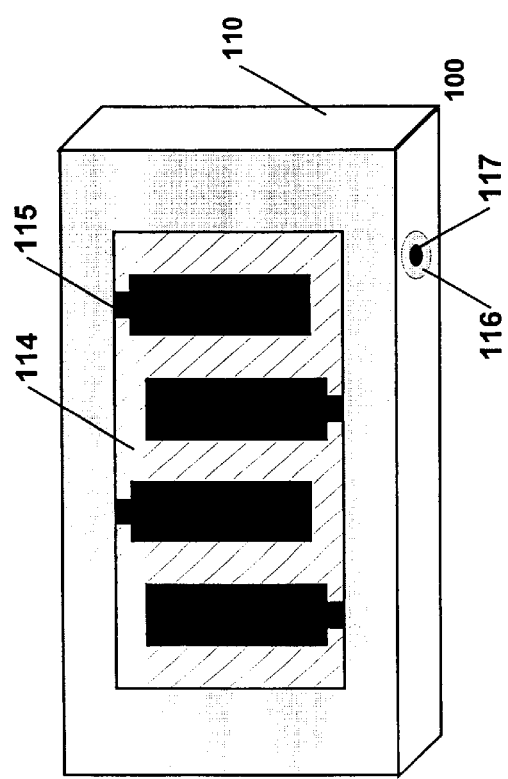

Top and bottom external views of the battery-operated embodiment of the treatment device are shown in FIGS. 1A and 1B. The device 100 is built in a small, self-contained rectangular metal package measuring about 7.37 cm. long, 5.46 cm. wide, and 1.78 cm. in thickness.

Housing 110 is preferably metal. It provides mechanical protection for the apparatus and serves as a electromagnetic shield. Housing 110 is soldered shut. In battery holder 114 (Caltronics BH-124) accessible from outside the package (and which may be recessed or attached to the exterior of housing 110), the housing accommodates four standard 1.5 volt "AA" alkaline batteries 115 of approximately 1.5 volts each, which provide the electrical power for the unit.

The underside of the device, shown in FIG. 1B, accommodates a surface mounted coil of wire 120 referred to as the "treatment loop." One end of treatment loop 120 enters the bottom housing surface through a wire feed hole 140 in the bottom of housing 110. The other end of treatment loop is grounded at solder point 150 to the outside of housing 110. The treatment loop itself consists of five concentric, spiraled, rectangular turns of 20 AWG solid copper wire embedded in a 2 mm. (0.080 inch) thick sheet of high impact styrene 111 adhesively fastened to the bottom surface of housing 110. (Alternatively, the treatment loop may be constructed on a printed circuit board.) The windings are spaced 3.175 mm. apart and the overall dimensions of the loop are 2.858×5.258 cm.

The treatment loop 120 has a broad radiating pattern off the coil. It is not a "focused" radiation but a spreading radiation. More signal is available from the front then off the back of treatment loop 120 (the back is shielded by a ground plane). Tests were run using a loop without the back shield but the results were not as good as with a back shield. The signal is strongest in the center since that is where the "hot" lead connects to treatment loop 120.

Figure 3:
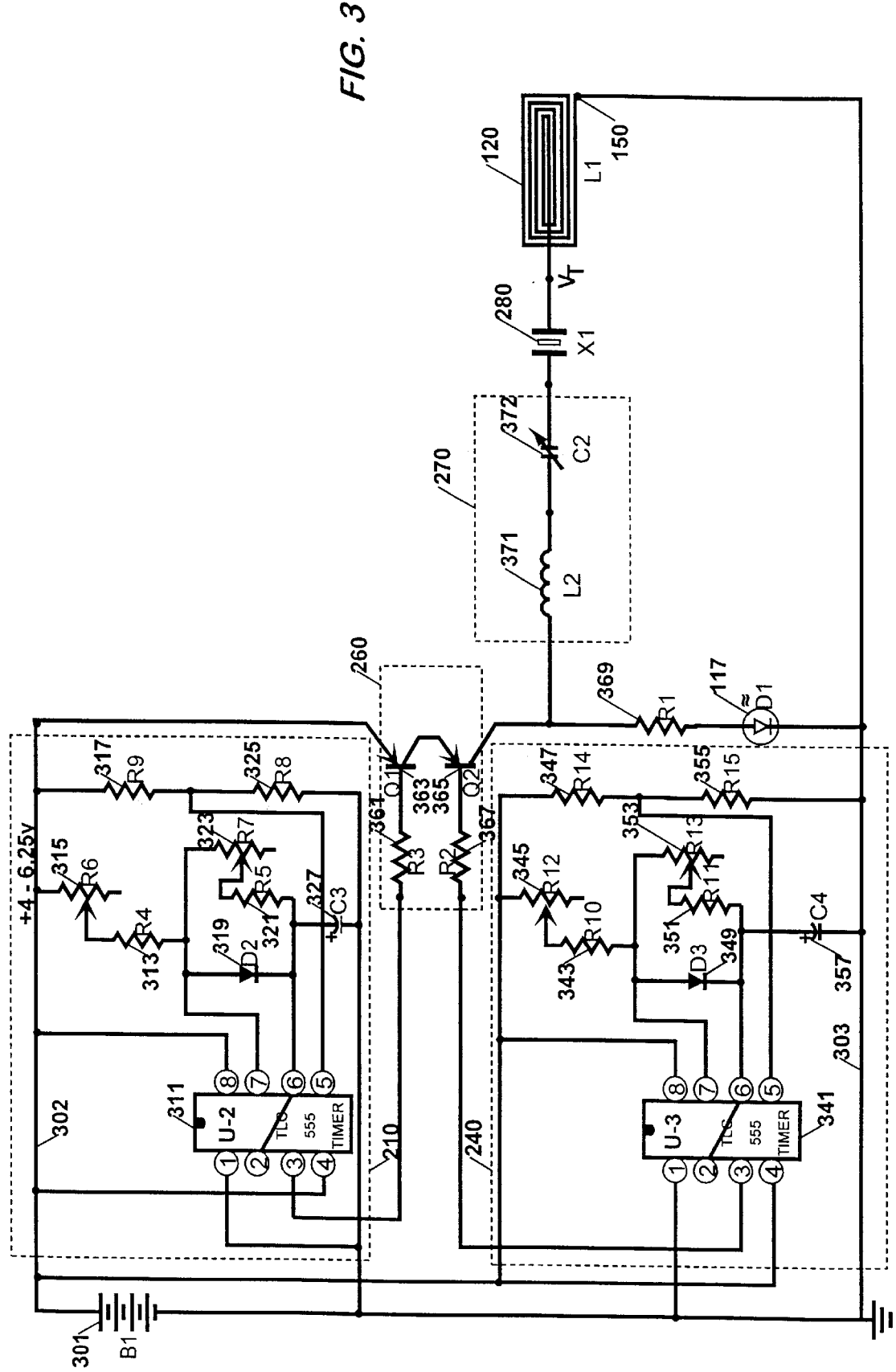
FIG. 3 is a schematic diagram of the Battery SCPO.
Figure 4A:
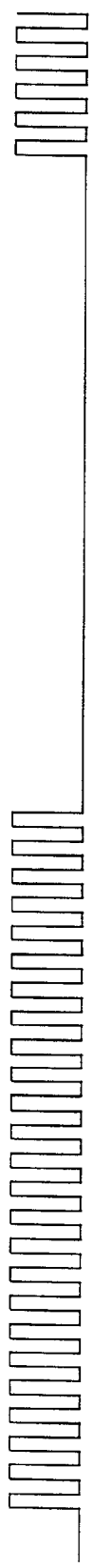
FIG. 4A shows the modulation waveform of the Battery SCPO.
Figure 4D:
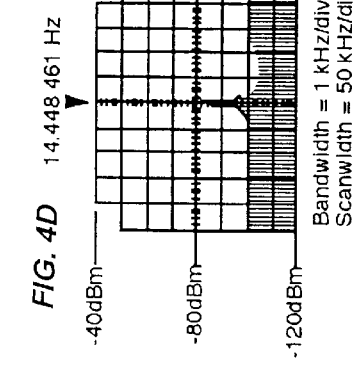
FIGS. 4B through 4F show spectrum analyses of the output of the Battery SCPO.
Figure 4C:
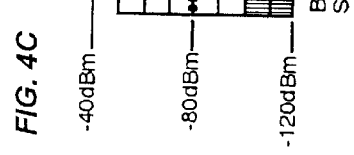
Figure 4F:
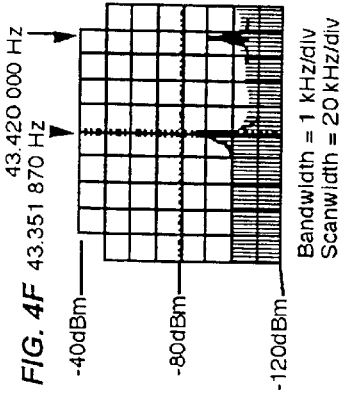
Figure 4B:
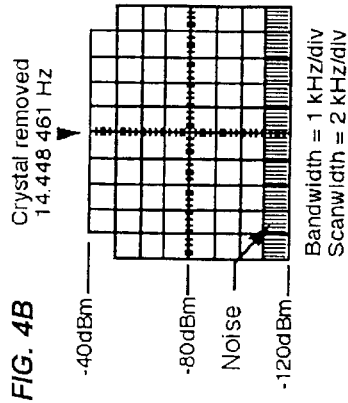
Figure 4E:
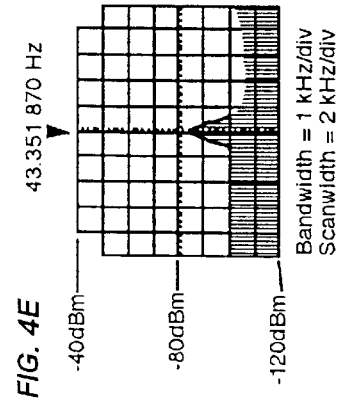

The circuitry that drives treatment loop 120 is contained on a printed circuit board 190 (shown in the cutaway 180 in FIG. 1B) within housing 110. The schematic for this circuit is shown in FIG. 3. The circuit comprises two timer circuits 210 and 240, which provide approximately a 60 Hz. approximately 50% duty cycle square wave, and an approximately 70 pulse per minute (1.167 Hz.) approximate 50% duty cycle square wave, respectively. These two square waves are combined in AND gate 260 in order to produce an approximately 60 Hz. square wave pulsed at approximately 1.167 Hz., each of the 60 Hz. Square wave and the 1.167 Hz. pulse having an approximate 50% duty cycle. The waveform output by AND gate 260 is shown in FIG. 4A.

The output of AND gate 260 is then directed through filter 270, and then to quartz crystal X1 280. Although many frequencies could be chosen from, the Battery SCPOs built to date have used a crystal cut for a third harmonic frequency of 43.351830±20 Hz., 43.351850±20 Hz., 43.351855±20 Hz. and 43.351870±20 Hz. (corresponding to base frequencies in the 14.450 MHz range). These frequencies have been found most effective for treating a broad range of maladies. The output of crystal 280 is directed to treatment loop 120.

Viewed in further detail, the schematic diagram in FIG. 3 shows the power for the circuit derived from the four cell battery 301. This power supply feeds positive rail 302 and ground rail 303.

The approximately 60 Hz. timing circuit 210 is based on a low power TLC 555 timer U2 311, set up as an astable multivibrator by connecting pins 2 (Trigger) and 6 (Threshold) together. Pin 1 is connected to ground 303. Pins 4 and 8 are connected to the positive supply rail 302. Pin 5 is connected to the midpoint of a voltage divider comprised of 1K resistor R9 317 (this, and all other fixed resistors referred to herein being 5%, ¼ Watt, unless otherwise specified) from the positive supply and 2.2 K resistor R8 325 to ground 302. Pin 6 is in addition connected to 1N914, 75 PIV, switching diode D2 319 forward biased from pin; to 0.22 uF (50 volt) electrolytic capacitor C3 327 to ground 303; to 47K resistor R5 321 to the wiper of 20K, 15 turn, ¾ watt adjustable resistor R7 323, one end of which is open and the other end of which is connected to pin 7. Pin 7 in addition is connected to 33K resistor R4 313 to the wiper of 20K, 15 turn, ¾ watt adjustable resistor R6 315, one end of which is open and the other end of which is connected to the positive supply rail 302. Pin 3 is the output.

The square wave frequency and duty cycle produced by 555 Timer U2 215 are adjusted by 20K, 15 turn, ¾ watt adjustable resistors R6 315 and R7 323 in accordance with the following formulas:

$t1$ (output high)$=0.693 \times (R4+R5+R6+R7) \times C3$ $t2$ (output low)$=0.693 \times (R5+R7) \times C3$ $T$ (total period)$=t1+t2$ $f$ (frequency)$=1/T$ $D$ (duty cycle)$=(R5+R7)/((R4+R6)+2 \times (R5+R7))$ (Units: R—Ohms; C—Farads; t, T—Seconds, f—Hz.)

The exact frequency and duty cycle of this square wave varies with the battery voltage and precise component values The 60 Hz. and 50% duty cycle figures required for successful operation of the preferred embodiment are believed to be plus or minus 10%, based on the condition of the batteries, exact component characteristics and environmental factors such as ambient and operating temperature.

The 1.167 Hz (70 pulse per minute) timing circuit 240 is similar to that of circuit 210. The approximately 1.167 Hz. timer circuit 240 is based on a low power TLC 555 timer U3 341, set up as an astable multivibrator by connecting pins 2 (Trigger) and 6 (Threshold) together. Pin 1 is connected to ground 303. Pins 4 and 8 are connected to the positive supply rail 302. Pin 5 is connected to the midpoint of a voltage divider comprised of 1K resistor R14 347 from the positive supply and 2.2 K resistor R15 355 to ground 303. Pin 6 is in addition connected to 1N914, 75 PIV, switching diode D3 349 forward biased from pin 7; to 10.0 uF (16 volt) electrolytic capacitor C4 357 to ground 303; to 47K resistor R11 351 to the wiper of 20K, 15 turn, ¾ watt adjustable resistor R13 353, one end of which is open and the other end of which is connected to pin 7. Pin 7 in addition is connected to 33K resistor R10 343 to the wiper of 20K, 15 turn, ¾ watt adjustable resistor R12 345, one end of which is open and the other end of which is connected to the positive supply rail 302. Pin 3 is the output.

The output voltage of both TLC 555 timer circuits 210 and 240 is approximately 4 volts, which varies with battery supply voltage.

The approximately 1.667 Hz. signal is combined with the approximately 60 Hz. signal in AND gate 260 which consists of 330 Ohm input resistors R2 367 and R3 367, and MPS2907 PNP transistors Q1 280 and Q2 290. FIG. 4A shows the waveform output from AND gate 260.

From the output of the AND gate 260 is a 2.15K resistor R1 369 in series with 2 ma red light emitting diode (LED) D1 117 (Radio Shack 276-044 or equivalent) forward biased to ground 303. The LED is visible on the outside of housing 110, and is in the circuit merely to provide a visual indicator that the Battery SCPO is operating.

The remainder of the circuit consists of 8.2 mH inductor L2 371 (Miller 8230-18), 5.5–18 pF trimmer capacitor C2 372 (Sprague-Goodman GY A22000 or equivalent), quartz crystal X1 280 and treatment loop L1 120 to ground 303.

Crystal X1 280 is cut so as to have a base frequency in the 14.4 MHz. Range, and a third harmonic at one of the following frequencies: 43.351830±20 Hz., 43.351850±20 Hz., 43.351855±20 Hz and 43.351830±20 Hz. Quartz crystal 280 is obtained from International Crystal Manufactures, P.O. Box 26330, Oklahoma City, Okla. 73126, and selected with great care. Other sources for crystals that have been used include CTS Corporation, Knights Division, 400 East Reimann Ave., Sandwich Ill. 60548 (which is no longer in business) and NEL Frequency Controls, Inc. 357 Beloit Street, Burlington Wis.

Crystals are ordered approximately 25–50 at a time for each frequency, and are then individually tested on a Saunders Crystal Test System so as to allow selection of crystals with the desired frequency characteristics. For one representative crystal, driven with a reference frequency near the expected series resonance frequency, with a drive level of 2060 uWatts into 44 Ohms, with a 10 pF capacitative load, the results of this testing were as shown in Table 2.

TABLE 2

Exemplary Crystal Measurements

| Parameter | Description | Value |
| --- | --- | --- |
| Fr(Hz.) | Series resonant frequency | 43,351,870 Hz. |
| Co(pF) | Shunt capacity | 4.0 pF |
| Rr(Ohms) | Motional Resistance | 18.2 Ohms |
| Q(k) | Quality factor | 161.0K |
| C1(fF) | Motional capacity | 1.3 femtoFarads |
| L(mH) | Motional Inductance | 10.7 mH |
| Fl(Hz.) | Loaded resonant frequency | 43,353,820 Hz. |
| Ts(ppm/pF) | Trim sensitivity | 3.2 ppm/pF |
| PWR(uWatt) | Power level | 2740.0 uWatts |

No oven is used in this device. Instead, the unit is turned on for 10 minutes before use, and used in a room at an ambient temperature of approximately 72 degrees Fahrenheit.

The output portion of the Battery SCPO involves a series LC circuit, a series crystal, and the treatment loop, which is another inductor. The large Motional Inductance of the crystal, and its very small Motional Capacitance, dominate the output circuit. This is driven by the square wave train coming out of AND gate 260. The modulation waveform output from AND gate 260, measured at the collector of transistor Q2 365, as shown in FIG. 4A, has a rise time of 18 nS and fall time approximately 120 nS. To a reasonable approximation, each 60 Hz. cycle in the modulation waveform represents a 4 volt step input with the aforementioned rise and fall times, into a series LC circuit with low series resistance. The high frequency components of the steep rise and fall of this square wave stimulates a ringing of the crystal at its characteristic base frequency and harmonics.

The actual output of the Battery SCPO at the point of input to Treatment Loop 120 can be observed on an oscilloscope, and visibly contains RF frequencies. This was observed using an SCPO constructed with a 43.351870 Hz. Crystal. When the signal from the SCPO was input into a spectrum analyzer, a −75 dB peak is observed at the 14.448461 MHz. base crystal frequency, and a −85 dB peak is seen at the 43.351870 MHz. third harmonic frequency of the crystal. An additional, weaker RF signal is observed at 43.420000 MHz. These various spectrum analyzer scans are shown in FIGS. 4B through 4F.

In sum, rather than using a conventional crystal oscillator circuit, the battery SCPO uses a crystal series driven by audio range square wave input pulses, in order to generate low power, yet precisely tuned, pulsed RF energy.

The treatment device is used by applying it, treatment loop down, to the subject's body in the area desired to be treated. The unit is left in place for approximately one hour at a time.

As indicated above, battery SCPOs have been built with crystals tuned to 43.351830±20Hz., 43.351850±20 Hz., 43.351855±20 Hz and 43.351870±20 Hz. These frequencies were chosen because they are each believed to be useful for treating a plurality of illnesses, and because a multipurpose device is advantageous by reason of the inconvenience of changing crystals. However, there is no reason why this embodiment, would not be effective at any of the frequencies identified above as being therapeutically useful, as well as, with an appropriately tuned output element, if necessary, at any frequency found in the future to be therapeutically useful.

A parts list for the Battery SCPO is set forth in Table 3.

TABLE 3

Parts List for Battery SCPO

| Ref. No. | Description | Source |
| --- | --- | --- |
| 110 | SCPO Housing | Fabricated - See text |
| 114 | Battery Holder | Caltronics BH-124 |
| 115 | "AA" Battery 4 ea | Wallgreens 1.5 V AA Ultra Alkaline or equiv. |
| 117 | D1 Indicator Light - 2 mA LED Diode | Radio Shack 276–044 or equiv. |
| 120 | Treatment Loop | Fabricated - See text |
| 127 | Backing for treatment loop | High Impact Styrene 0.080" thick |
| 280 | Quartz Crystal | ICM, CTS, or NEL - See text |
| 311 | U2 - TLC 555 Timer | Radio Shack 276-1723 or equiv. |
| 313 | R4 33K +/− 5% 1/4 Watt Carbon Resistor | Radio Shack 271-1341 or equiv. |
| 315 | R6 20K 15 Turn 3/4 Watt Adj. Resistor | Radio Shack 271-340 or equiv. |
| 317 | R9 1.0K +/− 5% 1/4 Watt Carbon Resistor | Radio Shack 271-1321 or equiv. |
| 319 | D2 1N914 Switching Diode 75 PIV | Radio Shack 276-1122 or equiv. |

TABLE 3-continued

Parts List for Battery SCPO

| Ref. No. | Description | Source |
|---|---|---|
| 321 | R5 47K +/− 5% 1/4 Watt Carbon Resistor | Radio Shack 271-1342 or equiv. |
| 323 | R7 20K 15 Turn 3/4 Watt Adj. Resistor | Radio Shack 271-340 or equiv. |
| 325 | R8 2.2K +/− 5% 1/4 Watt Carbon Resistor | Radio Shack 271-1325 or equiv. |
| 327 | C3 0.22 uf Electrolytic Capacitor, 50 Volts | Radio Shack 272-1070 or equiv. |
| 341 | U3 - TLC 555 Timer | Radio Shack 276-1723 or equiv. |
| 343 | R10 33K +/− 5% 1/4 Watt Carbon Resistor | Radio Shack 271-1341 or equiv. |
| 345 | R12 20K 15 Turn 3/4 Watt Adj. Resistor | Radio Shack 271-340 or equiv. |
| 347 | R14 1K +/− 5% 1/4 Watt Carbon Resistor | Radio Shack 271-1321 or equiv. |
| 349 | D3 1N914 Switching Diode 75 PIV | Radio Shack 276-1122 or equiv. |
| 351 | R11 47K +/− 5% 1/4 Watt Carbon Resistor | Radio Shack 271-1342 or equiv. |
| 353 | R13 20K 15 Turn 3/4 Watt Adj. Resistor | Radio Shack 271-340 or equiv. |
| 355 | R15 2.2K +/− 5% 1/4 Watt Carbon Resistor | Radio Shack 271-1325 or equiv. |
| 357 | C4 1 Ouf Electrolytic Capacitor, 16 Volts | Radio Shack 272-1436 or equiv. |
| 361 | R2 330 Ohm +/− 5% 1/4 Watt Carbon Resistor | Radio Shack 271-1315 or equiv. |
| 363 | Q1 MPS2907 PNP Transistor | Radio Shack 276-2023 or equiv. |
| 365 | Q2 MPS2907 PNP Transistor | Radio Shack 276-2023 or equiv. |
| 367 | R3 330 Ohm +/− 5% 1/4 Watt Carbon Resistor | Radio Shack 271-1315 or equiv. |
| 369 | R1 2.2K +/− 5% 1/4 Watt Carbon Resistor | Radio Shack 271-1325 or equiv. |
| 371 | L2 8.2 uH Inductor | Miller 8230-18 |
| 372 | C2 5.5 - 18 pF Trimmer Capacitor | Sprague-Goodman GYA22000 or equiv. |

B. Generator Embodiment

Figure 5:
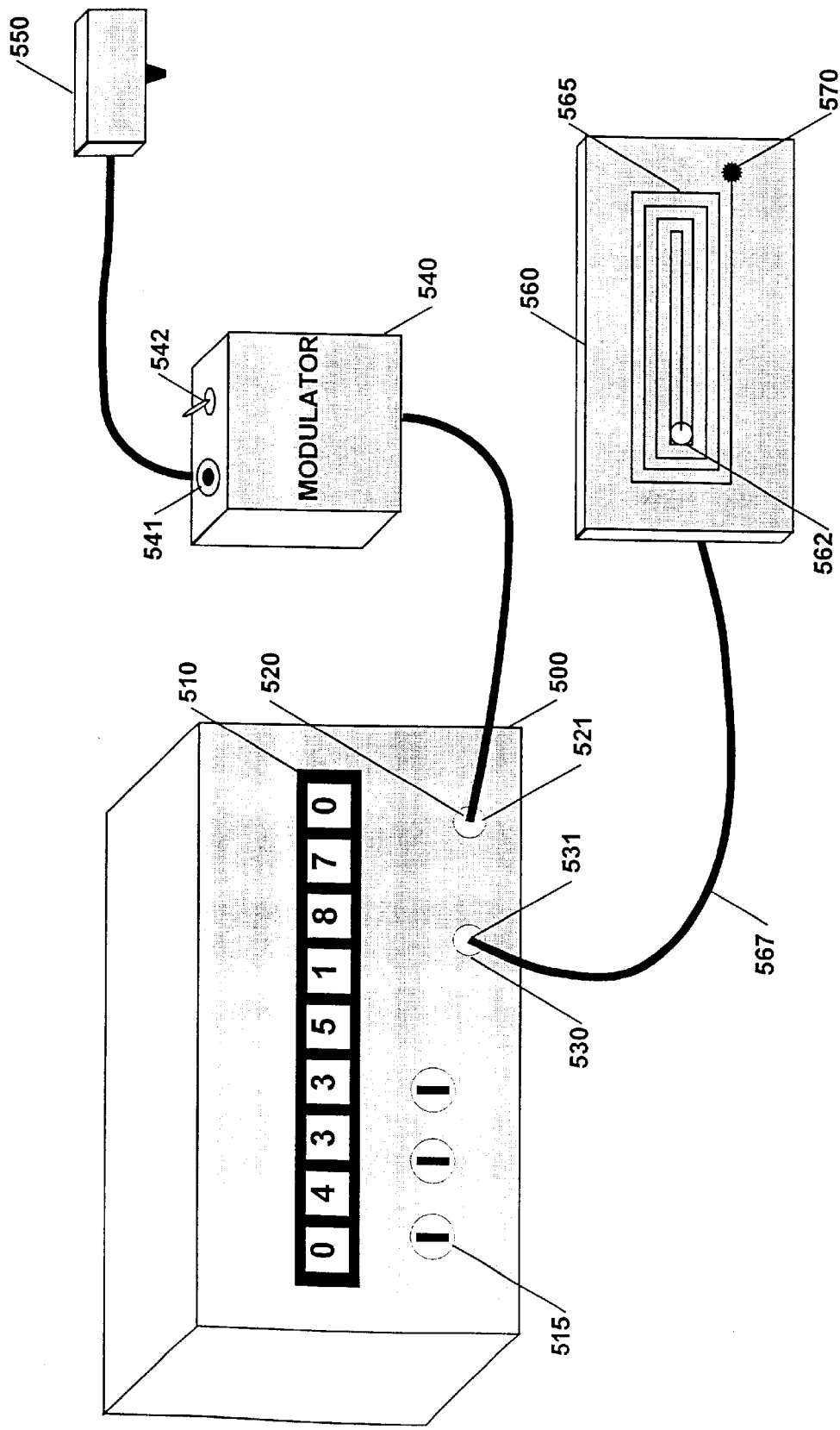
FIG. 5 is an external view of the components of the Generator Embodiment.

The alternate embodiment of the treatment device is shown in FIG. 5. It employs a model 8662A frequency generator 500 manufactured by the Hewlett-Packard Company. Frequency generator 500 has a modulation input 520, to which is connected modulator unit 540, which provides an approximate 60 Hz square wave with an approximate 50% duty cycle, which is in turn gated with an approximately 1.167 (70 pulse per minute) square wave, also with an approximately 50% duty cycle.

The circuitry of modulator unit 540, which is more fully described below, is similar to that of the Battery SCPO, up to the point of AND gate.

Figure 6:
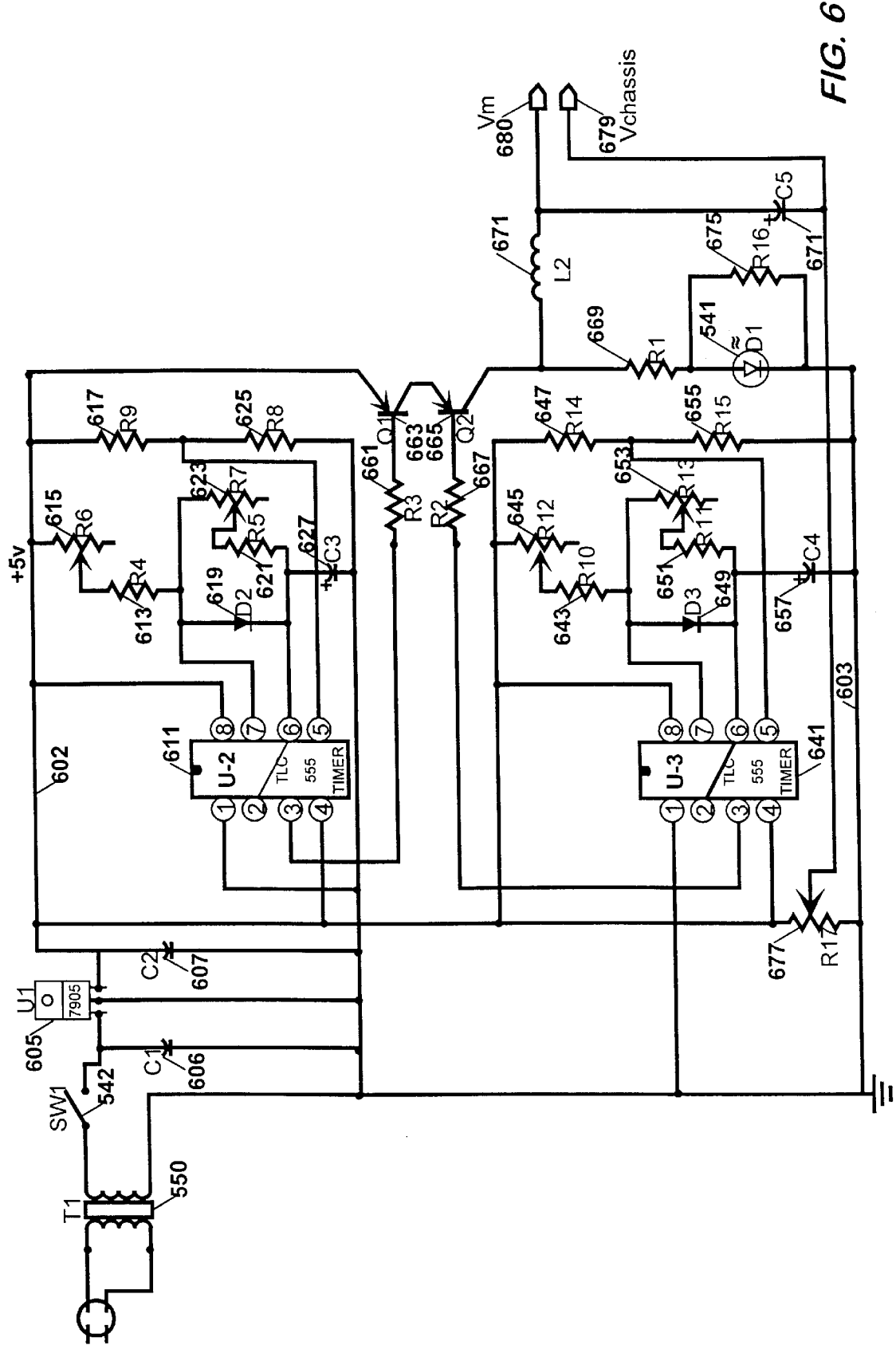
FIG. 6 is a schematic diagram of the modulator circuit for the Generator Embodiment.

As shown in FIG. 6, power is provided by a plug-in DC power module 550, Radio Shack Cat. No. 273-1455C or equivalent, which is rated at 9 volts D.C. at 0.3 amperes. The positive lead from the module is switched through power switch SW1 542, and then directed to a 7805 5 volt voltage regulator U1 605. The negative lead of the supply is attached to the unit's ground rail 603. Both the input and output of voltage regulator U1 605 is bypassed to ground by a 0.01 uF, 500 volt disc ceramic capacitor, C1 606 and C2 607. The output, a regulated 5 volts, is applied to positive supply rail 602.

The circuitry associated with the TLC 555 timers 611 and 641 is shown in FIG. 6, and is identical with the corresponding circuitry described above in the context of the Battery SCPO. The reference numerals "611" through "657" in FIG. 6 correspond to the identical elements "311" through "357" in FIG. 3.

The AND gate of the modulator for the Generator Embodiment is configured identically here as in the Battery SCPO. R2, R3, Q1 and Q2 (661, 663, 665, and 667) have the same values as in the SCPO circuit (361, 363, 365 and 367).

The LED indicator circuit R1 669 and D1 541 differs from its counterpart in the Battery SCPO in that R1 669 is 330 Ohms rather than 2.15K. The resistor difference is for the purpose of obtaining the proper LED brightness in each circuit.

Adjustable resistor R17 677 provides a voltage divider between positive rail 602 and ground 603. The wiper of R17 677 provides a positively offset "ground" for purposes of output to the HP 8662A. The reason for this is that the HP 8662A expects an DC signal for purposes of modulation, so this adjustment is provided to offset the output around "zero volts" as referenced to the chassis of the HP 8662A.

The output of AND gate at the emitter of Q2 665 is connected to 8.2 uH inductor L2 671 (Miller 8230-18). The resultant signal is bypassed to ground by a relatively large electrolytic capacitor, 1.5 uF, rated at 35 volts C5 673, and then passed to the center lead of output BNC connector 521.

Figure 7A:
FIGS. 7A and 7B show, respectively, the modulation waveform and a portion of the output waveform of the Generator Embodiment.
Figure 7B:
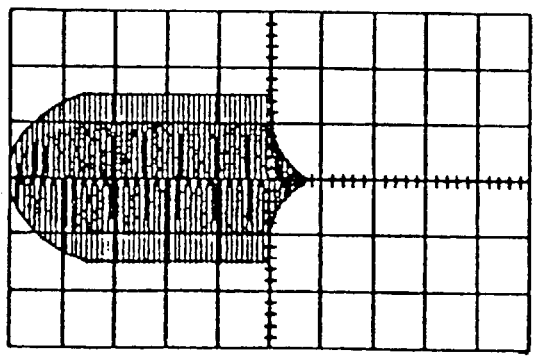

The approximate modulation waveform produced by modulator unit 540 is shown in FIG. 7A. The rounding of the rise and fall of the waveform is the result of capacitor C5 673. The modulated waveform of one of the 60 Hz. cycles output by the HP 8662A is shown in FIG. 7B (the RF component in this figure is not drawn to scale). The output power of the frequency generator is less than 1 mw.

The output of frequency generator 500 is directed through a second BNC connector 531 connected to the panel of that instrument, and through a 50 Ohm, double-shielded coaxial cable 567 (RG 174 cable, Mouser #515-156-12 or equivalent). The coaxial cable is directed to a treatment loop 565 mounted on 2.0 mm. (0.080 inch) thick styrene sheet 566 which is laminated on stainless steel plate 560. The plate has dimensions of approximately 10.2 cm. by 6.35 cm. The treatment loop 565 is a 20 AWG solid copper wire approximately 60 cm. long, wound in a flat rectangular spiral comprising five turns, with a turn-to-turn spacing of approximately 3.175 mm. and overall dimensions of 2.858× 5.258 cm. The center of the loop is soldered to the center lead of coaxial cable 567. Shield 863 of coaxial cable 567 is soldered to the back of plate 560 at solder point 861. The outer end of treatment loop 565 is grounded by being soldered at solder point 570 to the loop side of plate 560. (Use A and B figures to show both sides of the plate.

The signal from the frequency generator based embodiment of the treatment device is stronger electromagnetically than that output by battery operated device 100. It is also characterized by having only a single pure RF component at the desired frequency in the 43 MHz range. The treatment loop of generator embodiment is applied to the subject in the same manner as in the case of the battery powered embodiment.

A parts list for the Generator Embodiment is set forth in Table 4.

TABLE 4

Parts List for Generator Embodiment

| Ref. No. | Description | Source |
|---|---|---|
| 500 | Hewlett-Packard 8662A Frequency Generator | Hewlett-Packard Company |
| 541 | D1 Indicator Light - 2mA LED Diode | Radio Shack 276-044 or equiv. |

TABLE 4-continued

Parts List for Generator Embodiment

| Ref. No. | Description | Source |
|---|---|---|
| 542 | SW1 Power Switch | Radio Shack 275-612 or equiv. |
| 550 | 9VDC Plug-In Power Supply Module | Radio Shack 273-1455C or equiv. |
| 560 | Treatment Loop holder | Fabricated - See text |
| 565 | Treatment Loop | Fabricated - See text |
| 567 | Coaxial Cable, 50 ohm, Shielded | RG174 cable Mouser #515-1156-12 |
| 605 | U 1 7805 5 Volt Voltage Regulator IC | Radio Shack 276-1770 or equiv. |
| 606 | 0.01 uF Disc Ceramic Capacitor, 500 Volt | Radio Shack 272-131 or equiv. |
| 607 | 0.01 uF Disc Ceramic Capacitor, 500 Volt | Radio Shack 272-131 or equiv. |
| 611 | U2 - TLC 555 Timer | Radio Shack 276-1723 or equiv. |
| 613 | R4 33K +/- 5% 1/4 Watt Carbon Resistor | Radio Shack 271-1341 or equiv. |
| 615 | R6 20K 15 Turn 3/4 Watt Adj. Resistor | Radio Shack 271-340 or equiv. |
| 617 | R9 1.0 K +/- 5% 1/4 Watt Carbon Resistor | Radio Shack 271-1321 or equiv. |
| 619 | D2 1N914 Switching Diode 75 PIV | Radio Shack 276-1122 or equiv. |
| 621 | R5 47K +/- 5% 1/4 Watt Carbon Resistor | Radio Shack 271-1342 or equiv. |
| 623 | R7 20K 15 Turn 3/4 Watt Adj. Resistor | Radio Shack 271-340 or equiv. |
| 625 | R8 2.2K +/- 5% 1/4 Watt Carbon Resistor | Radio Shack 271-1325 or equiv. |
| 627 | C3 0.22 uf Electrolytic Capacitor, 50 Volts | Radio Shack 272-1070 or equiv. |
| 641 | U3 - TLC 555 Timer | Radio Shack 276-1723 or equiv. |
| 643 | R 10 33K +/- 5% 1/4 Watt Carbon Resistor | Radio Shack 271-1341 or equiv. |
| 645 | R 12 20K 15 Turn 3/4 Watt Adj. Resistor | Radio Shack 271-340 or equiv. |
| 647 | R 14 1K +/- 5% 1/4 Watt Carbon Resistor | Radio Shack 271-1321 or equiv. |
| 649 | D3 1N914 Switching Diode 75 PIV | Radio Shack 276-1122 or equiv. |
| 651 | R11 47K +/- 5% 1/4 Watt Carbon Resistor | Radio Shack 271-1342 or equiv. |
| 653 | R13 20K 15 Turn 3/4 Watt Adj. Resistor | Radio Shack 271-340 or equiv. |
| 655 | R15 2.2K +/- 5% 1/4 Watt Carbon Resistor | Radio Shack 271-1325 or equiv. |
| 657 | C4 1 0uf Electrolytic Capacitor, 16 Volts | Radio Shack 272-1436 or equiv. |
| 661 | R2 330 Ohm +/- 5% 1/4 Watt Carbon Resistor | Radio Shack 271-1315 or equiv. |
| 663 | Q1 MPS2907 PNP Transistor | Radio Shack 276-2023 or equiv. |
| 665 | 02 MPS2907 PNP Transistor | Radio Shack 276-2023 or equiv. |
| 667 | R3 330 Ohm +/- 5% 1/4 Watt Carbon Resistor | Radio Shack 271-1315 or equiv. |
| 669 | R1 330 Ohm +/- 5% 1/4 Watt Carbon Resistor | Radio Shack 271-1315 or equiv. |
| 671 | L2 8.2 uH Inductor | Miller 8230-18 |
| 673 | C5 1.47 uF Electrolytic Capacitor, 35 Volts | Radio Shack 272-1433 & 1434 |
| 677 | R 17 5K Adj. 15 Turn 3/4 Watt Adj. Resistor | Radio Shack 271-340 or equiv. |

C. Alternative "Mouse SCPO" for Mouse Studies

Figure 2:
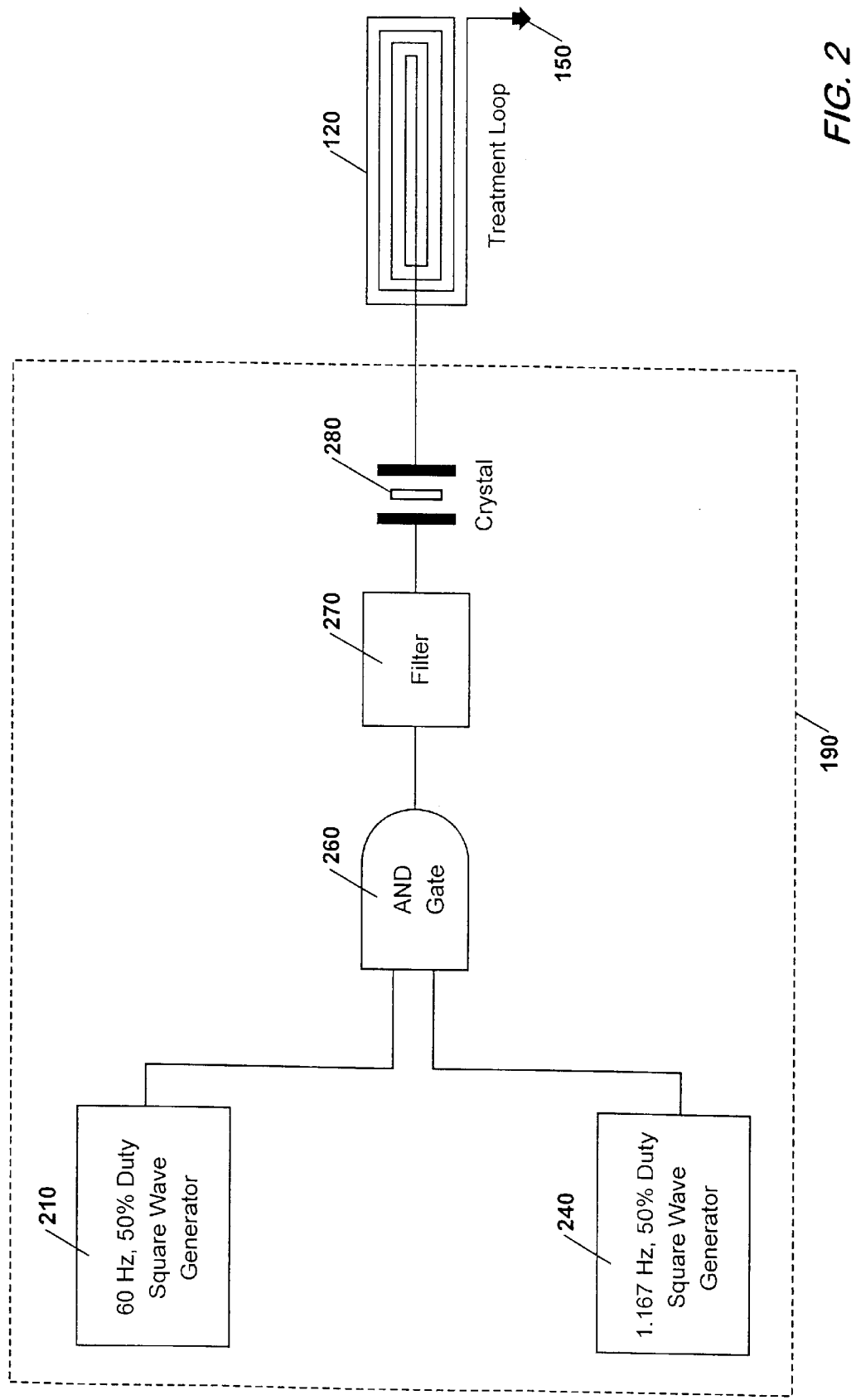
FIG. 2 is a block diagram of the major functional units of the Battery SCPO.

For purposes of the mouse studies described below, an alternative embodiment of the treatment device was developed, hereinafter referred to as the "Test Embodiment". The Mouse SCPO consisted of an apparatus similar to the battery SCPO described above, but without a battery compartment, and powered by an external AC power adapter. The power adapter used was the same Radio Shack adapter 550 used with the modulator for the Generator Embodiment. The power supply circuit in the Mouse SCPO was identical to that used in the modulator for the Generator Embodiment, comprising the 7805 regulator U1 605, and the two 0.01 uF bypass capacitors C1 606 and C2 607. In all other respects, the Mouse SCPO was as shown in FIGS. 1, 2 and 3, using the components listed in Table 4.

The feature lacked by the Mouse SCPO is the lack of restraint resulting from not being tethered by a wire. However, in the case of treating mice, this feature is irrelevant, since the mice must be immobilized for treatment in any event. On the other hand, the Test Embodiment had the advantage that it had no batteries to run low and to be checked and replaced.

D. Externally Pulsed Generator Embodiment

A further alternative embodiment of the treatment apparatus was developed, herein referred to as the "Externally Pulsed Generator." The Externally Pulsed Modulator embodiment is identical to the apparatus shown in FIG. 5, except that (1) the modulator does not attach to the Modulator Input of the HP 8662A, but rather attaches directly via a BNC connector to the RF output of the HP 8662A, (2) the modulator externally modulates the RF signal and does not utilize the internal modulation circuitry provided by the HP 8662A; and (3) the cable used to connect the modulator to the Treatment Loop is a specific type of coaxial cable, i.e., a Hewlett-Packard 10501A, 50 Ohm coaxial cable approximately 1.1 meters long.

The modulator in the Externally Pulsed Generator embodiment contains a series solid state RF switch and associated connectors, which is pulsed by a pulsing circuit identical to that shown in FIG. 6, except that potentiometer R17 677 and capacitor C5 671 have been removed and the ground is taken from the main power supply ground rail 1303 (corresponding to rail 603 in FIG. 6). (Since there is no need to interface with the modulator input of the 8662A, there is no need for the floating ground used in the output circuit of FIG. 6.)

Figures 36, 36A:
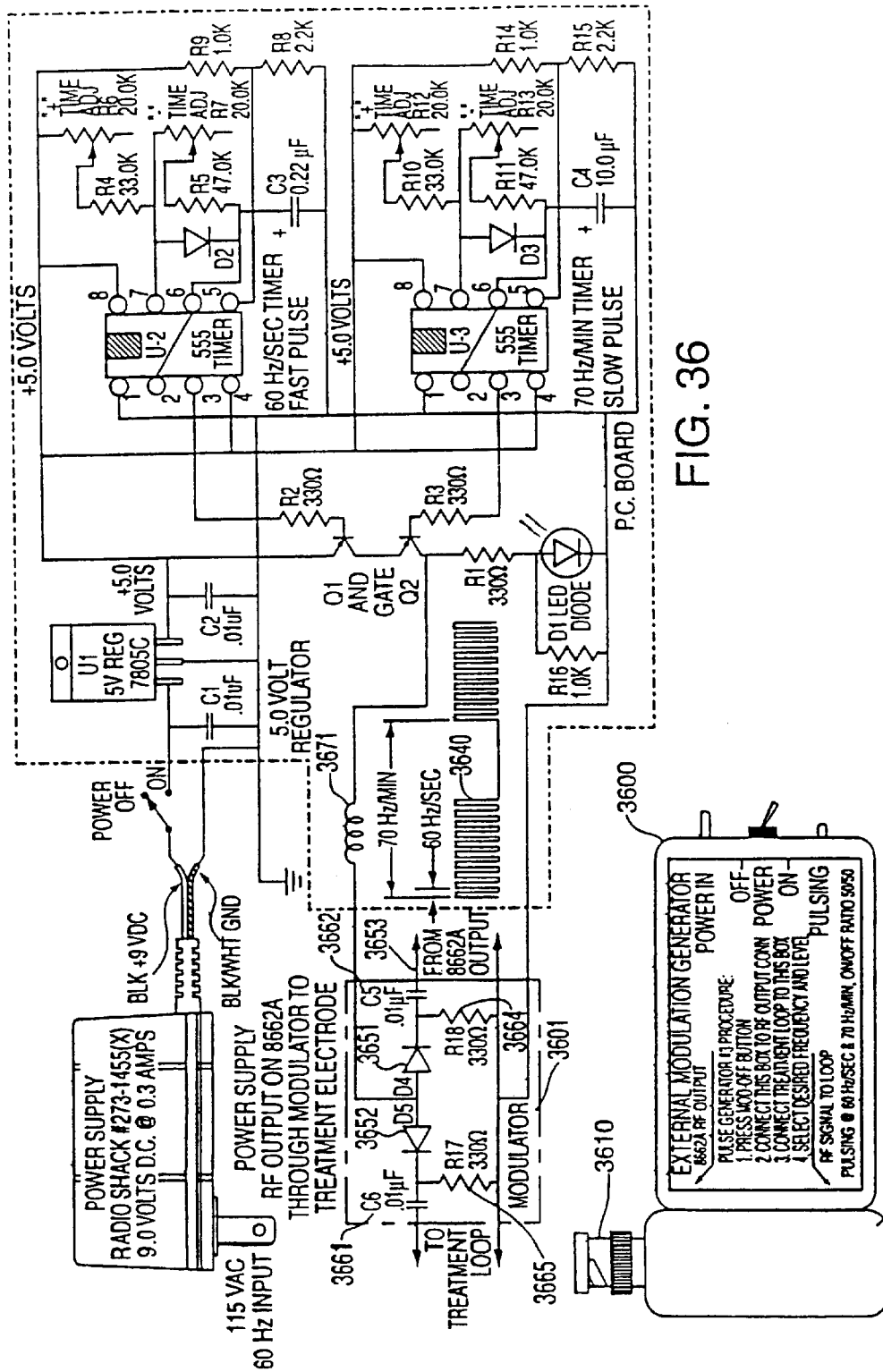
FIG. 36 is a schematic diagram for an external modulator that attaches to the radio frequency output of an HP 8662A Frequency Generator and FIG. 36A is a top view of the exterior of the device.

The schematic diagram in FIG. 36 shows the entire circuit of this external modulator. In FIG. 36A, which shows the exterior of the device, shielded box 3601 is attached to the end of modulator housing 3600. Male BNC connector 3610 attaches directly to the RF output of the 8662A. Female BNC connector 3620 attaches to the 10501 coax which in turn leads to the Treatment Loop. (Since this unit is a self-contained external modulator, it is necessary to turn off the modulation internal to the HP 8662A using the switch for that purpose on the control panel of the HP 8662A.)

In the RF switching circuit, the output of inductor L2 3671 is a 60 Hz/1.667 Hz. waveform 3640 (also as shown in FIG. 7A). This waveform shifts the bias on D4 3651 and D5 3652 so as to switch the RF applied to input 3653 in accordance with the pulses from L2 3671. In addition, inductor L2 3671 serves in this circuit as an RF choke keeping excessive RF from going back into the pulsing circuitry.

TABLE 4A

Additional Part for Externally Pulsed Generator Embodiment

| Ref. No. | Description | Source |
|---|---|---|
| 500 | C5 0.01 µf capacitor | Radio Shack 272-131 or equiv. |
| 541 | C6 0.01 µf capacitor | Radio Shack 272-131 or equiv. |
| 542 | R17 330 Ohm +/- 5% 1/4 Watt Carbon Resistor | Radio Shack 275-1315 or equiv. |
| 542 | R18 330 Ohm +/- 5% 1/4 Watt Carbon Resistor | Radio Shack 275-1315 or equiv. |

TABLE 4A-continued

Additional Part for Externally Pulsed Generator Embodiment

| Ref. No. | Description | Source |
|---|---|---|
| 550 | D4 1N914 Switching Diode 75 PIV | Radio Shack 273-1122 or equiv. |
| 560 | Metal Box | Any suitable supplier |
| 565 | Male BNC connector | Any suitable supplier |
| 567 | Female BNC connector | Any suitable supplier |

3. Experimental Procedure and Results

A controlled set of experiments were conducted during 1995 and 1996, to Jun. 25, 1996, to test the utility of the present invention with respect to the suppression and elimination of cancerous tumors, cysts, lesions, and neoplasia. The experiments were performed upon mice, by the topical application of electromagnetic (EMR) radiation at specific frequencies and intensities on a regular schedule, using the apparatus of the present invention as adapted for applying EMR to mice. We also present some additional measurements taken in 1997 with respect to one mouse that was treated using the Externally Pulsed Generator Embodiment.

"Suppression and elimination" means that tumors, etc. that do develop are smaller in size, occur relatively infrequently and are likely to disappear over time, as opposed to untreated tumors that are larger in size, occur more frequently and are unlikely to disappear before the death of the subject.

Use of JAX Mice as Experimental Subjects

The Jackson Laboratory at Bar Harbor, Me., 04609 supplies mice for scientific research. These special mice are "JAX Mice," of a special inbred breed identified as C3H HeOuJ. These mice are highly abnormal, in that they are inherently very susceptible to adenocarcinoma of the mammary gland, due to the contributing factors of inherited genes, excessive hormonal stimulation, and the mouse mammary tumor virus, which is passed to the young through the mother's milk. The adenocarcinomas develop spontaneously in these mice, and the breed is characterized by a high incidence of mammary tumors by eight months of age. Our project has used "JAX Mice" type C3H HeOuJ throughout all of its research for treatment of mouse tumors, including all of the treated and control mice referred to herein.

The JAX C3H HeOuJ mice were selected in order to provide a sensitive animal model for testing anticancer treatments. The effectiveness of various treatments for such tumors is measured by determining improvements in lifespan or other physical characteristics, such as gross appearance, health status, and other related data, of groups that have received the treatment, as against untreated controls. This manner of testing using JAX mice is accepted as a valid animal model for determining the prospective utility of cancer treatments in humans.

In a memorandum dated Mar. 18, 1997, The Jackson Laboratory notified users of C3H/HeOuJ that it had observed an alteration over time of the development and incidence of tumors in this strain. Our experiments were primarily conducted in a much earlier time frame than that concerned in this memorandum, and we do not believe any of our experimental results were affected thereby.

Summary of Experimental Procedures and Results

"Control" and "treated" selections of JAX mice (10 mice per group) were observed over the duration of their lives. Control mice were not exposed to the treatment procedure at all. The treated mice were exposed to EMR at the skin layer. The treatment given was exposure to electromagnetic radiation applied to the skin of the mouse, with the radiation held at a given frequency throughout the treatment. The duration of treatment was usually one-half to one hour, and during the treatment, the treating electrode was shielded from undue light and moving air currents.

The data from our experiments, discussed in detail below, show that:

1. Treated mice live much longer than controls.
2. The life spans of treated mice compare favorably with life spans of normal (i.e., non-JAX) mice.
3. Treated mice have good health throughout their life.
4. Prior treatment has prevented abdominal tumor development.
5. When an abdominal tumor has been treated directly on the electrode it is caused to disappear.
6. By contrast:
   a) Tumors on control mice grow rapidly until death of the mouse,
   b) And as tumors grow, a control mouse gains weight, its hematocrit decreases and its health fails rapidly until death.

Treatment of the particular mice herein discussed was by exposure of the JAX mice to radiation from an electrode which was energized by a low power source that was preset to provide frequencies of 43.351830 MHz, 43.351850 MHz and 43.351870 MHz. In some cases, an HP-8662A Signal Generator preset to these frequencies was used, equipped with a modulator (in all but the 1997 data, an internally coupled modulator), to provide approximately 1.667 and 60 Hz., approximately 50% duty cycle square wave pulse trains as previously described. In other cases, the same pulsed treatment frequencies were obtained with the "Mouse SCPO" embodiment described above, which contained its own modulator circuit, driving an internal quartz crystal.

The frequencies selected, as listed in the preceding paragraph, were based on prior experiments conducted over a period of many years, during which a large number of mice were treated under varying conditions and with various treatments. The three frequencies specified in the preceding paragraph are believed by the inventors to be among the most effective frequencies for treating a range of maladies. When using the Mouse SCPO embodiment, the treatment frequency used 69% of the time (659 hours out of a total of 950) was 43351870 Hz. When using the HP 8662A signal generator for treatment, many (35) different frequencies were used.

Treatment Procedures

One of the treated mice (OUJ-479) received treatments before a tumor appeared and lived and died tumor free.

Treatment of the remaining mice started as soon as a tumor reached 0.07" in length, width, and height, corresponding to an ellipsoid having a volume of 0.0295 cubic cm. (0.00018 cubic inches). The treatments for all these ten mice were every day except Sunday. The treatment frequencies are limited to a few specific frequencies within a narrow range, and the intensities are normally set to 0 dBm into a 50 ohm load.

Due to variations among individual mice (as in other species, including humans), a treatment configuration that is effective for one subject doesn't always work for another. Frequencies of 43.351850 MHz and 43.351870 MHz were used for standard treatment on almost all of the mice. These frequencies have demonstrated good results. Treating mice with 43.351850 MHz from a signal generator and/or pulsed crystal, appears to clear up their secondary infections, and treating with 43.351870 MHz seems to restore their general health. All of the treated mice appeared to be very lively and have a very healthy skin and hair appearance. Of the mice listed below, all hematocrit values have stayed in the healthy range of 38% to 46%, and their weight basically stayed the same since they began treatment.

Hematocrits for both the treated and the control mice were measured in accordance with the following procedure. The hematocrit was taken once a week. The mouse was placed under a heat lamp for a few minutes to cause the veins in the tail to dilate, thus making it easier to extract the blood for the sample. The amount of blood taken was about one-half of the standard 75 mm long capillary tube. The capillary tubes containing the blood are spun in a Micro-Hematocrit Centrifuge, at its "number three" marking. The capillary tubes are removed and placed in the Micro-hematocrit Tube Reader, which gives the percent of red blood cells found in the sample.

We have observed that tumors that have reached 0.07" in length, 0.07" in width, 0.07" in height are definitely a malignant growth, and benign or cystic lesions can be ruled out. Neoplasia measured under the agreed size are questionable. Almost all of the neoplasia encountered measured 0.07", 0.07", 0.07" and above.

The treatments employed a variety of treatment electrodes and housings, as shown in FIG. 9. The preferred housing was the "E" housing shown in FIG. 9A, and the preferred electrodes were the "I" electrode associated with the Mouse SCPO, FIG. 9J, and the "F" electrode used with the Hewlett-Packard signal generator, FIG. 9B.

Tumors treated directly on the treatment electrode slowly regressed until they were gone. Tumors that were not on, or only partially on, the electrode showed a decrease in growth rate, but the tumor would steadily grow and not regress back The electrode was re-designed so that any tumor could be treated. The tumor must be directly on the electrode to receive the maximum treatment needed for complete regression of growth. Mice with lesions on their abdomen had direct contact with the electrode, and all completely regressed back to zero. We've had similar success with some mice with lesions on the neck, left leg, right neck, right side, etc.

Since mammary tumors occur spontaneously in these mice, some mice were also treated before any tumors appeared in the hope of preventing the inevitable fate of the cancerous C3H strain, which have an almost 100% occurrence rate. At present one of the mice lived out its life span tumor free and died of old age.

Treated Mice

The following describes our experimental results with respect to each individual treated mouse. For each mouse, there is a corresponding drawing showing where on the mouse tumors appeared, and in which the tumors are identified by a "tumor number" T-X, as well as a drawing reference numeral; a graph showing tumor volume in cubic inches vs. time in days; a graph showing mouse weight in grams and hematocrit readings vs. time in days; and an Appendix setting forth all experimental measurements taken with respect to the mouse.

Figure 10A:
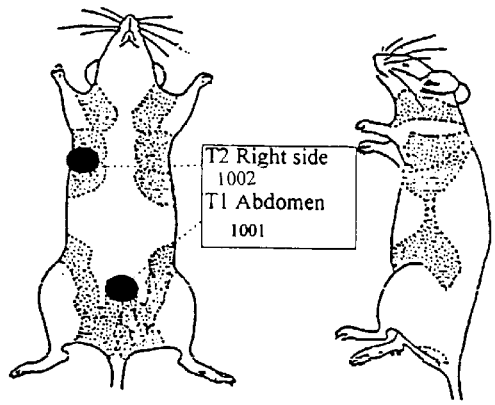
FIGS. 10 through 29 show, for each treated and control mouse involved in the inventors' experimental studies, A, the locations of the tumors (if any) that developed, B, plots (on a logarithmic scale) of the respective volumes of the various tumors as a function of time, and C, plots of the mouse's weight and hematocrit measurements as a function of time.
Figure 10B:
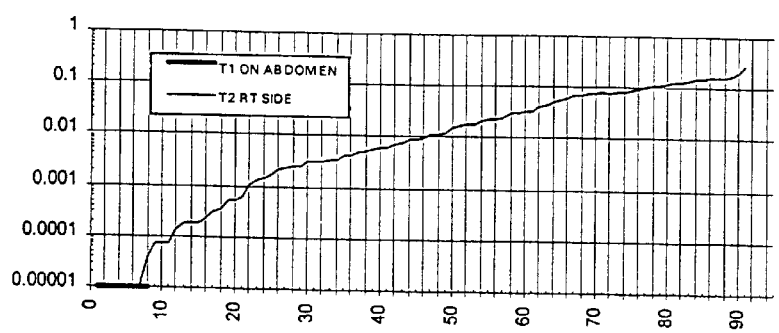
Figure 10C:
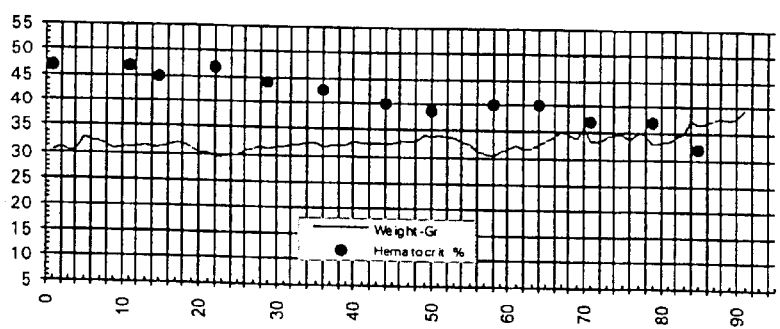
Figure 11A:
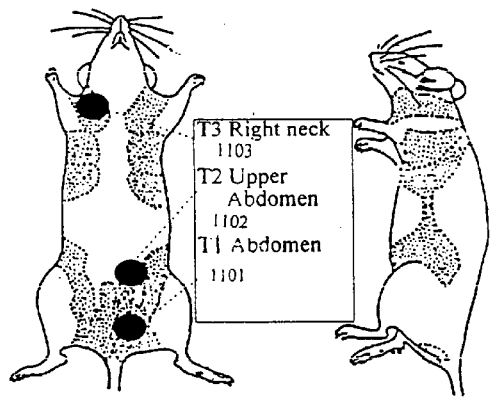
Figure 11B:
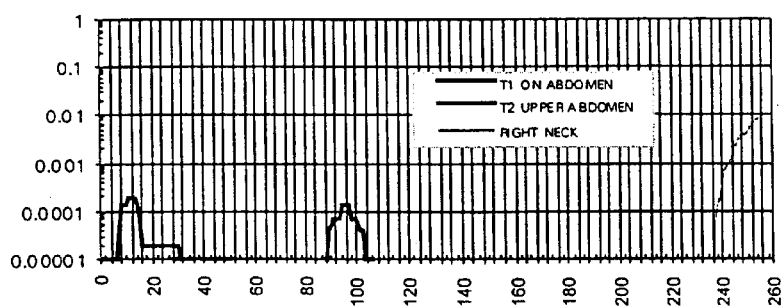

Each tumor growth graph (FIGS. 10B, 11B, etc.) shows the size of each tumor, in cubic inches, on the mouse in question as a logarithmic function of days after the appearance of the subject's first tumor. Tumor volume, in cubic inches, was calculated based on the assumption that the tumor was approximately an ellipsoid, and had a volume equal to ½ length×½ width×height×2.094.

Figure 11C:
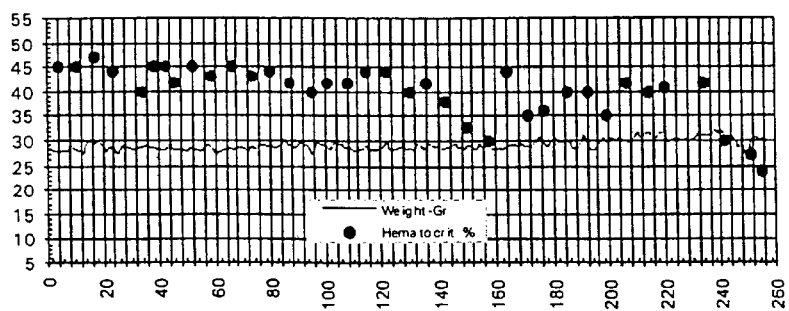

Each weight and hematocrit graph (FIGS. 0C, 11C, etc.) shows, in two separate plots, (a) the weight of the mouse, in grams, and (b) the subject's hematocrit values (percentage of red blood cells) as a linear function of days after the appearance of the subject's first tumor.

The detailed data collected with respect to each treated mouse is shown in tabular form in Appendices A-1, A-2, etc. attached hereto, and the data collected with respect to each control mouse is shown in tabular form in Appendices, B-1, B-2, etc. attached hereto. The data with respect to one mouse tested in 1997 is shown in tabular form in Appendix C.

EXAMPLE 1

Treated Mouse OUJ-456

TABLE 5

Treatment Summary for OUJ-456

| | |
|---|---|
| Date of Birth: | Sep. 08, 1994 |
| Date Died: | Aug. 04, 1995 |
| Lived: | 310 days |
| Treated: | 91 days |
| Tumor measurements started: | May 05, 1995 |
| Tumor measurements taken for: | 91 days |

This mouse lived 219 days before any tumor appeared. Notice (in FIG. 10B) that T-2 1002, which was hard to reach with our electrodes, grew, but at a slower rate than a typical control mouse. As will be seen from this and the other examples herein, treated mice live three times longer than controls after a tumor appears.

EXAMPLE 2

Treated Mouse OUJ-470

TABLE 6

Treatment Summary for OUJ-470

| | |
|---|---|
| Date of Birth: | Mar. 03, 1994 |
| Date Died: | Jul. 30, 1995 |
| Lived: | 515 days |
| Treated: | 257 days |
| Tumor measurements started: | Nov. 16, 1994 |
| Tumor measurements taken for: | 257 days |

This mouse lived 258 days before any tumor appeared. Notice (in FIG. 11B) that T-1 1101 appeared and went away at two different times. T-2 1102 appeared for a short period. T-3 1103 appeared when this mouse was 496 days old. This is one of the longest-lived mice in our experiments.

EXAMPLE 3

Treated Mouse OUJ-471

TABLE 7

Treatment Summary for OUJ-471

| | |
|---|---|
| Date of Birth: | Mar. 03, 1994 |
| Date Died: | Jul. 20, 1995 |
| Lived: | 504 days |
| Treated: | 199 days |

TABLE 7-continued

Treatment Summary for OUJ-471

| | |
|---|---|
| Tumor measurements started: | Jan. 02, 1994 |
| Tumor measurements taken for: | 199 days |

Figure 12A:
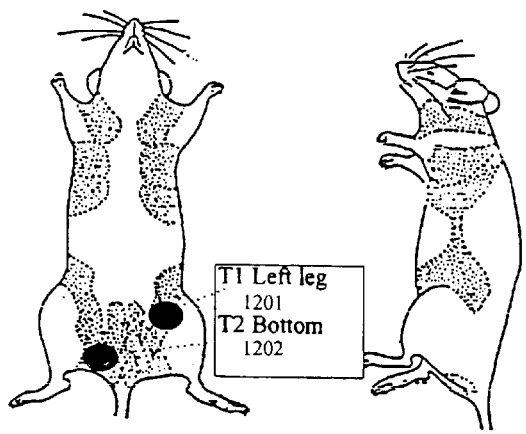
Figure 12B:
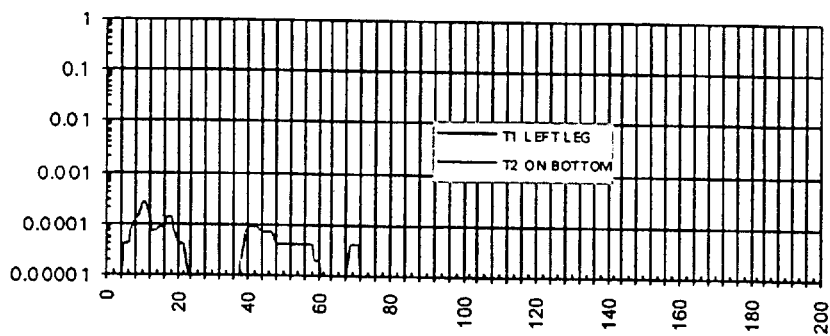
Figure 12C:
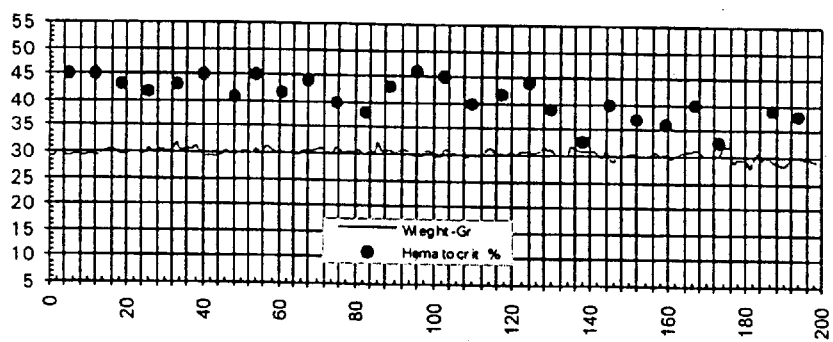

This mouse lived 305 days before any tumor appeared. Notice that T-1 1201 and T-2 1202 appeared for a short period. Notice (in FIG. 12C) the steady weight at 30 grams and constant high hematocrit percentage readings. This was also one of our longest-lived mice.

EXAMPLE 4

Treated Mouse OUJ-473

TABLE 8

Treatment Summary for OUJ-473

| | |
|---|---|
| Date of Birth: | Mar. 03, 1994 |
| Date Died: | Jul. 28, 1995 |
| Lived: | 514 days |
| Treated: | 211 days |
| Tumor measurements started: | Dec. 29, 1994 |
| Tumor measurements taken for: | 211 days |

Figure 13A:
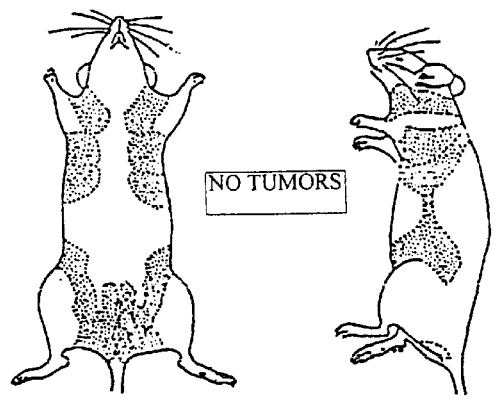
Figure 13B:
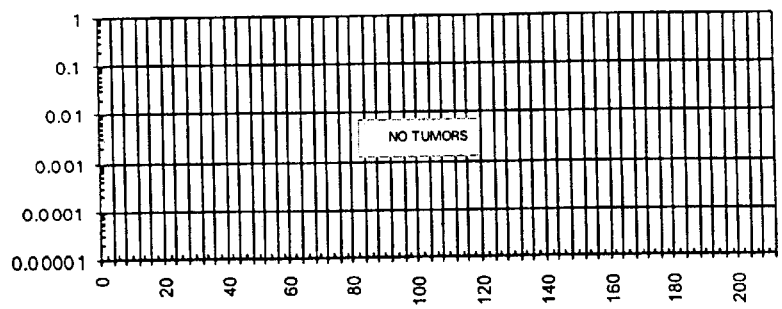
Figure 13C:
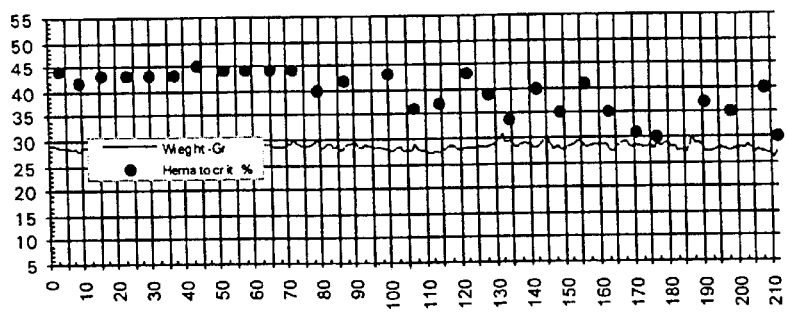

As an experiment, we treated this mouse before any tumors appeared. This mouse never developed any tumors (FIG. 13B). She lived 303 days before we started treatments. Notice (in FIG. 13C) the steady weight at 28 grams. This was also one of our longest-lived mice.

EXAMPLE 5

Treated Mouse OUJ-475

TABLE 9

Treatment Summary for OUJ-475

| | |
|---|---|
| Date of Birth: | Mar. 03, 1994 |
| Date Died: | Jul. 28, 1995 |
| Lived: | 514 days |
| Treated: | 256 days |
| Tumor measurements started: | Nov. 14, 1994 |
| Tumor measurements taken for: | 256 days |

Figure 14A:
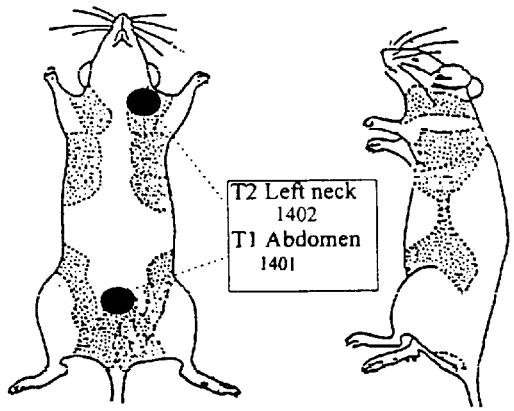
Figure 14B:
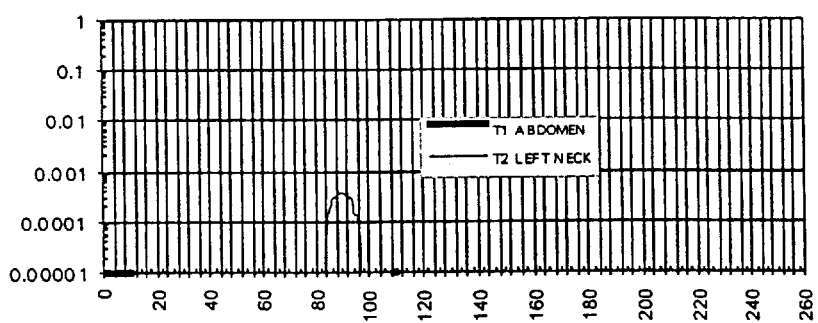
Figure 14C:
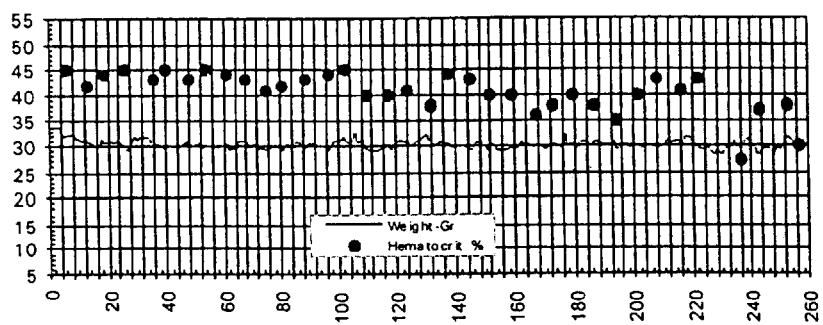

This mouse lived 258 days before any tumor appeared. Notice (FIG. 14B) that T-1 1401 and T-2 1402 appeared for a short period. Notice (FIG. 13C) the steady weight at 30 grams and quite-constant high hematocrit percentage readings. This was also one of our longest-lived mice.

EXAMPLE 6

Treated Mouse OUJ-496

TABLE 10

Treatment Summary for OUJ-496

| | |
|---|---|
| Date of Birth: | Dec. 21, 1994 |
| Date Died: | Jan. 05, 1996 |
| Lived: | 380 days |
| Treated: | 113 days |
| Tumor measurements started: | Sep. 15, 1995 |
| Tumor measurements taken for: | 113 days |

Figure 15A:
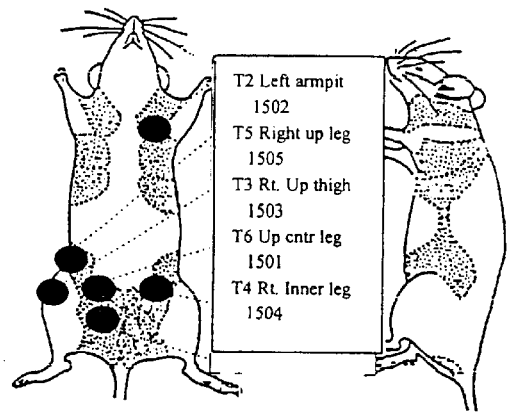
Figure 15B:
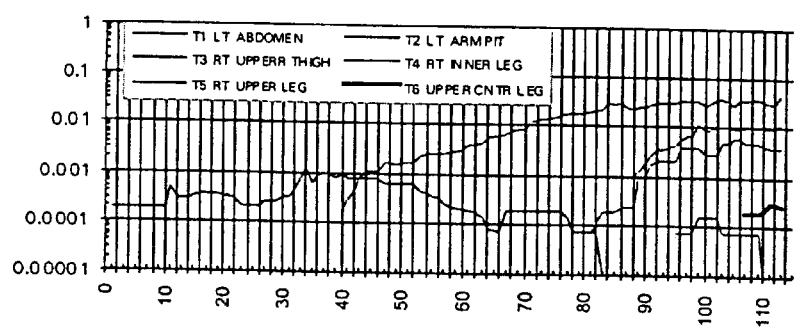
Figure 15C:
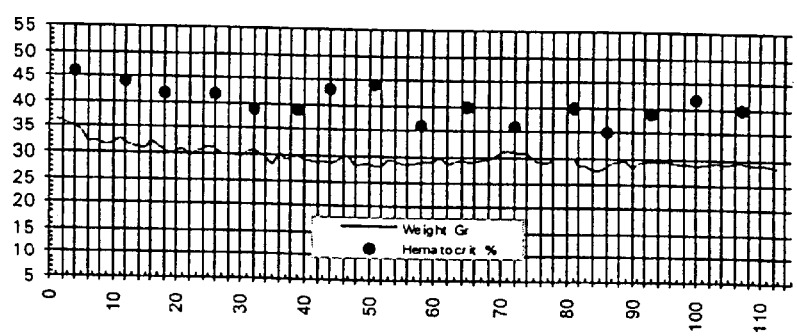

This mouse lived 267 days before any tumor appeared. Notice (FIG. 15B) that T-1 1501 and T-5 1505 appeared and left. Notice (FIG. 15C) the steady weight at 30 grams and high hematocrit percentage readings. Even with all these tumors, this mouse stayed healthy until the end and lived a long time.

EXAMPLE 7

Treated Mouse OUJ-506

TABLE 11

Treatment Summary for OUJ-506

| | |
|---|---|
| Date of Birth: | Jan. 05, 1995 |
| Still living: | Aug. 25, 1996 |
| Lived: | 537 days |
| Treated (and/or took data): | 250 days |
| Tumor measurements started: | Oct. 19, 1995 |
| Tumor measurements taken for: | 250 days |

Figure 16A:
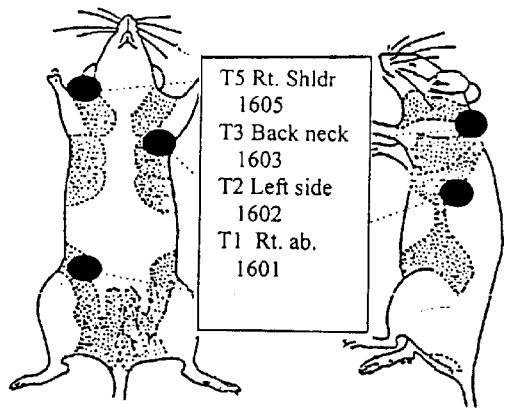
Figure 16B:
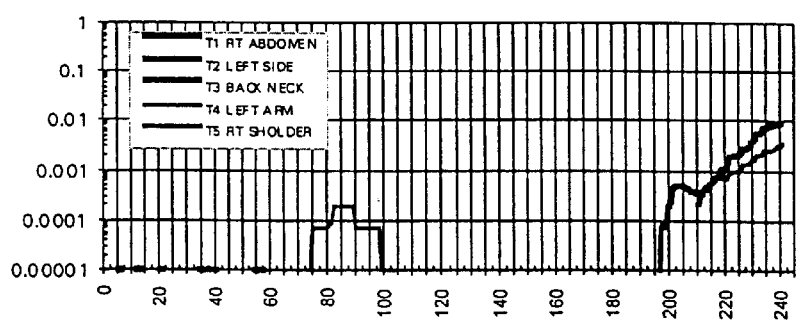
Figure 16C:
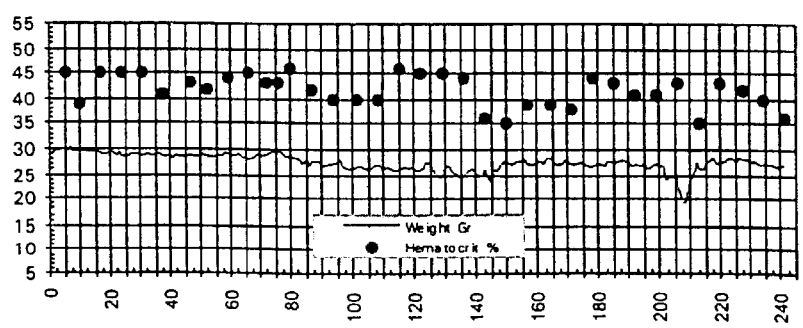

This mouse lived 287 days before any tumor appeared. Notice (FIG. 16B) that T-1 1601, T-2 1602, and T-3 1603 appeared for a short period. After 170 days, T-2 1602 reappeared. Notice (FIG. 16C) the constant high hematocrit percentage readings. This was our longest-lived mouse, and it had a long healthy life.

EXAMPLE 8

Treated Mouse OUJ-516

TABLE 12

Treatment Summary for OUJ-516

| | |
|---|---|
| Date of Birth: | Feb. 02, 1995 |
| Date Died: | Mar. 26, 1996 |
| Lived: | 418 days |
| Treated: | 240 days |
| Tumor measurements started: | Jul. 31, 1995 |
| Tumor measurements taken for: | 240 days |

Figure 17A:
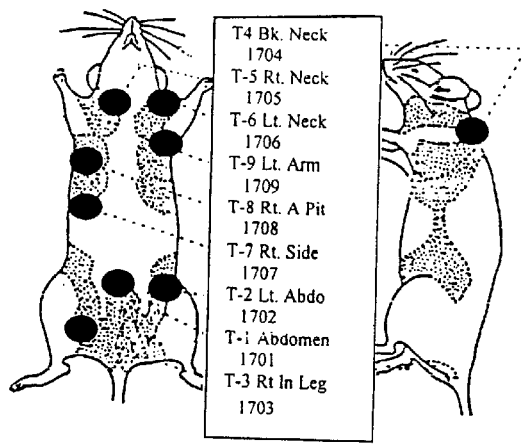
Figure 17B:
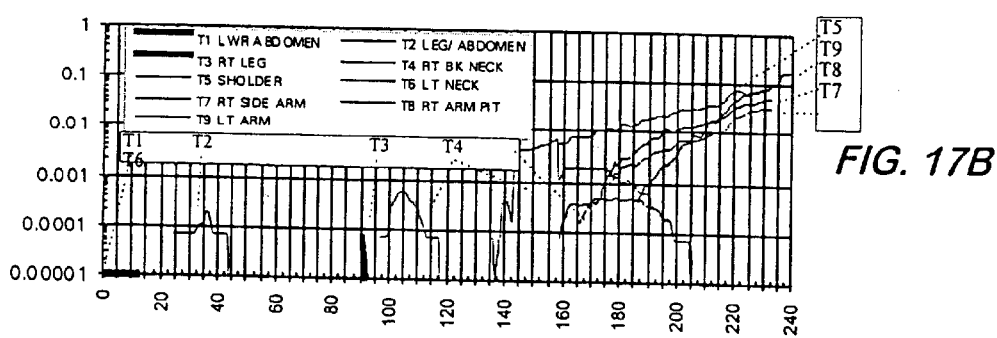
Figure 17C:
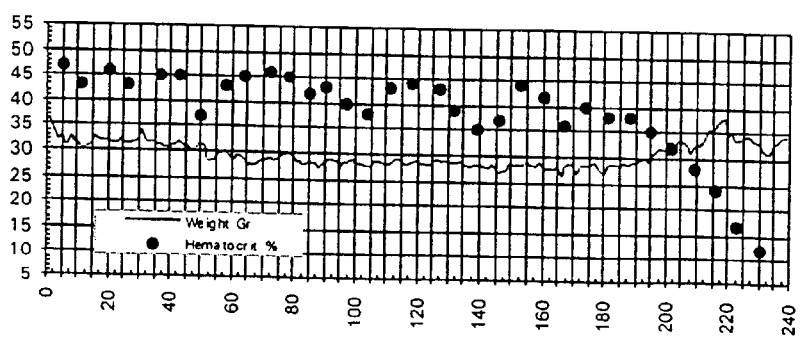

This mouse had a record number of tumors, many of which were not on the abdomen (FIG. 17A). After treatment all tumors disappeared except T5 1705, T7 1707, T8 1708, and T9 1709 (FIG. 17B). In spite of the large number of tumors, she lived 418 days.

EXAMPLE 9

Treated Mouse OUJ-526

TABLE 13

| Treatment Summary for OUJ-526 | |
| --- | --- |
| Date of Birth: | Feb. 02, 1995 |
| Date Died: | Apr. 12, 1996 |
| Lived: | 435 days |
| Treated: | 168 days |
| Tumor measurements started: | Oct. 28, 1995 |
| Tumor measurements taken for: | 168 days |

Figure 18A:
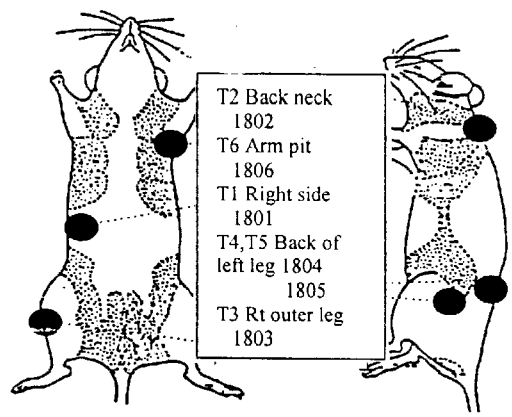
Figure 18B:
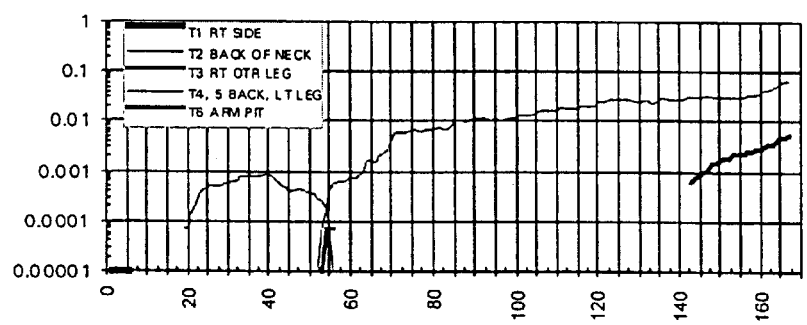
Figure 18C:
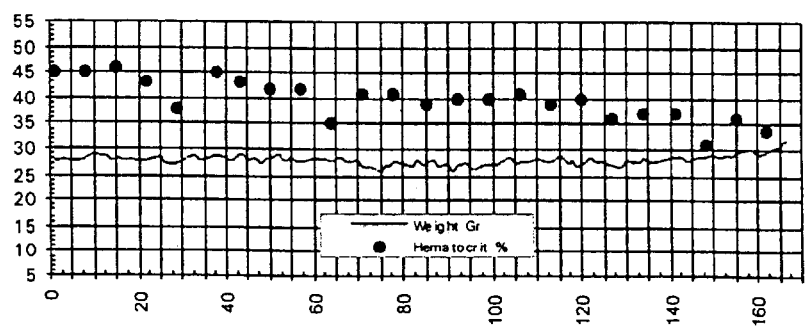

This mouse had three tumors which disappeared and never returned (FIG. 18B). She lived 267 days before any tumor appeared. T4 1804 and T5 1805 grew together as one tumor. Hematocrit percent (FIG. 18C) stayed quite high throughout her life.

EXAMPLE 10

Treated Mouse OUJ-650

TABLE 14

| Treatment Summary for OUJ-650 | |
| --- | --- |
| Date of Birth: | Apr. 04, 1995 |
| Still living: | Jun. 25, 1996 |
| Lived: | 448 days |
| Treated: | 195 days |
| Tumor measurements started: | Dec. 13, 1995 |
| Tumor measurements taken for: | 195 days |

Figure 19A:
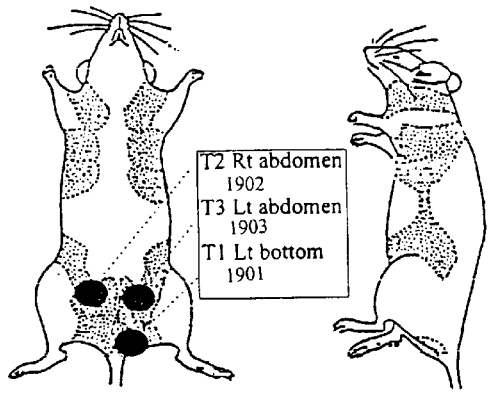
Figure 19B:
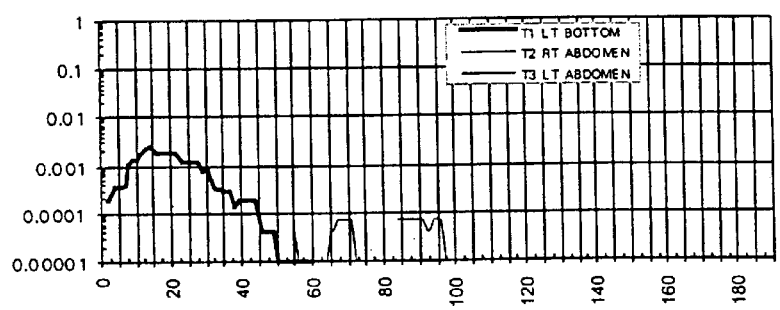
Figure 19C:
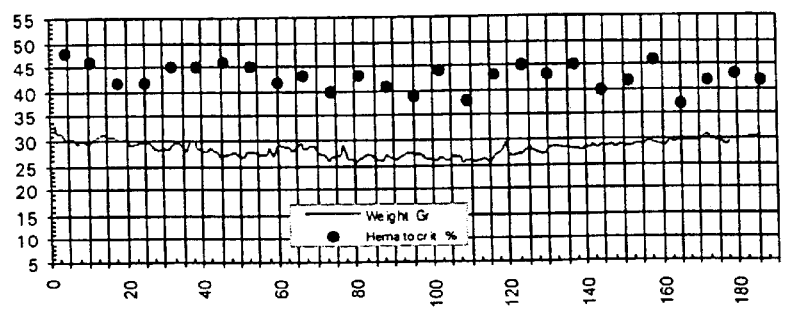

This mouse had three tumors, all of which disappeared and never re-appeared (FIG. 19B). Her hematocrit percent and remained high and her weight stayed constant throughout the measurement period (FIG. 19C).

Control Mice

The controls listed below all had spontaneous occurrences of multiple tumors that arose in various areas of the mammary gland region, and also had a very short survival time once the tumors appeared, usually around a two-month period.

None of the control mice in this study received EMR treatments or any other type of intervention methods. Daily weight and tumor measurements and observations were noted, as well as hematocrits to indicate the mouse's present health status at the time. These non-treated mice appeared to be in excellent health and appearance when the tumor remained small and didn't metastasize, but as the malignancy progressed and spread to other tissues, the effects on the mouse were readily seen.

The tumor measurements showed a rapid increase in tumor size that continuously rose almost every day, accompanied with a steady gain in weight, especially, with the arrival of new neoplasms. The hematocrit steadily lowers with the increase in tumor measurements. Other side-effects were also observed in the controls, such as, the coat began to show a rougher appearance, the back bone protruded out, they appeared to be malnourished, and the normal curiosity and physical activity seen in healthy mice were absent. The neoplasms' appearance also changed once the tumor reached a certain size, usually around 1.5 cm. in diameter and up. They usually would start to appear red and puffy, which would deepen in color showing areas of purple and black sores, which eventually ulcerated with severe bleeding. Some of the mice also appeared to get secondary infections once the tumor ulcerated, accompanied by the draining of clear fluid and WBC present in the wound. When the tumor reached a diameter of 1.8 cm., and the hematocrit value was 25% or lower, the mouse usually died within a couple of days.

As will be illustrated by the experimental data that follows, the characteristics of all control mice observed in the lab included the following: a rapid growth rate of tumors shown in the increasing size measurements and weight gain; metastasis; and continual decrease in hematocrit with the increasing tumor measurements. All the above symptoms affect the mouse's gross appearance, tumor appearance and shortened survival span once the tumors appear. This is reflected in the data that follows in the controls' rate of growth, and their decrease in hematocrit and length of survival period.

EXAMPLE 11

Control Mouse A-486

TABLE 15

| Summary for A-486 | |
| --- | --- |
| Date of Birth: | Apr. 04, 1995 |
| Date died: | Jun. 25, 1996 |
| Lived: | 448 days |
| Treated: | Not treated |
| Tumor measurements started: | Aug. 09, 1995 |
| Tumor measurements taken for: | 97 days |

Figure 20A:
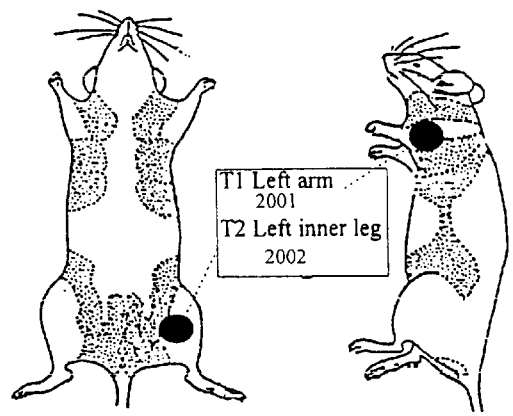
Figure 20B:
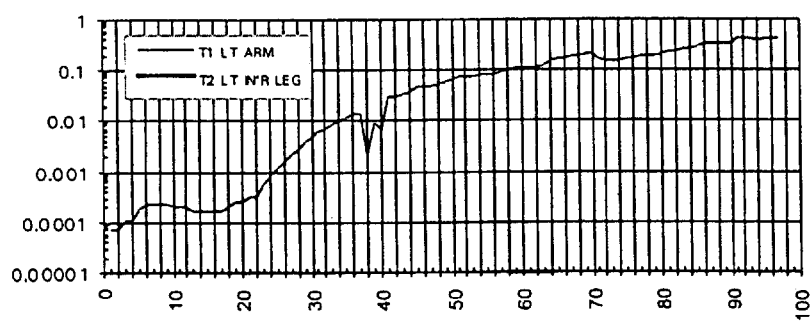
Figure 20C:
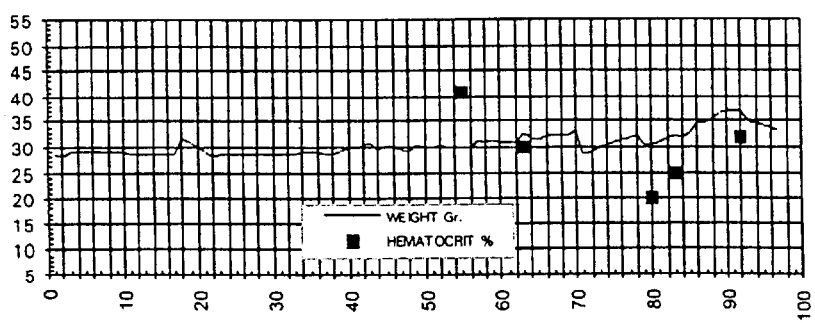

This mouse had one tumor which grew very rapidly to a large size (FIG. 20B). She had another tumor which appeared for 8 days. Her weight started to increase near the end, and the low hematocrit readings indicated a poor general health (FIG. 20C).

EXAMPLE 12

Control Mouse A-488

TABLE 16

| Summary for A-488 | |
| --- | --- |
| Date of Birth: | Nov. 28, 1994 |
| Date died: | Nov. 13, 1995 |
| Lived: | 350 days |
| Treated: | Not treated |
| Tumor measurements started: | Jul. 20, 1995 |
| Tumor measurements taken for: | 116 days |

Figure 21A:
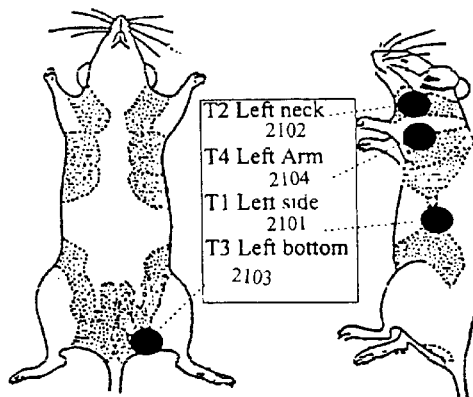
Figure 21B:
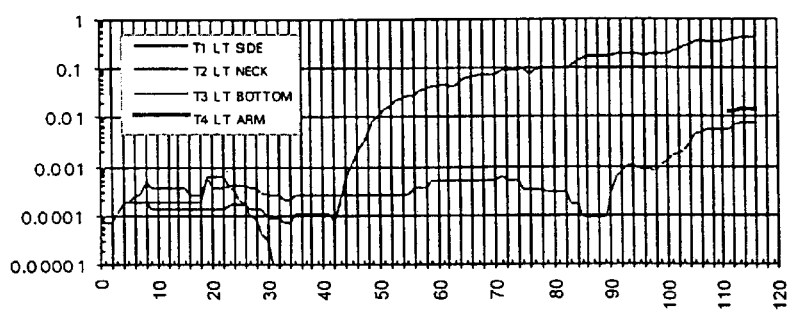
Figure 21C:
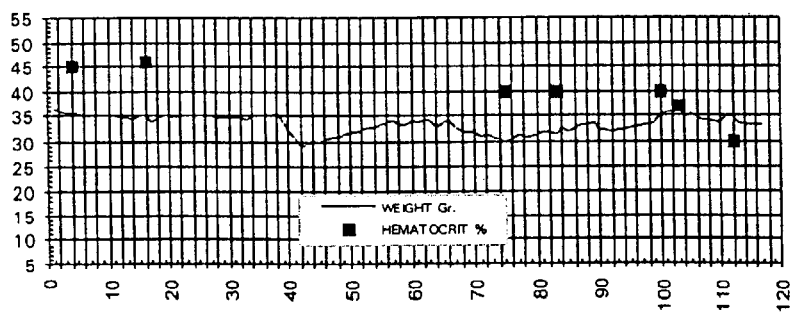

This mouse had one tumor (T1 2101) which didn't change much for forty days then grew rapidly (FIG. 21B). T-2 2102 came in and left after 32 days. T-3 2103 stayed constant in size for about 90 days, then grew rapidly.

EXAMPLE 13

Control Mouse A-490

TABLE 17

| Summary for A-490 | |
| --- | --- |
| Date of Birth: | Dec. 19, 1994 |
| Date died: | Nov. 29, 1995 |

TABLE 17-continued

Summary for A-490

| | |
|---|---|
| Lived: | 345 days |
| Treated: | Not treated |
| Tumor measurements started: | Oct. 11, 1995 |
| Tumor measurements taken for: | 50 days |

Figure 22A:
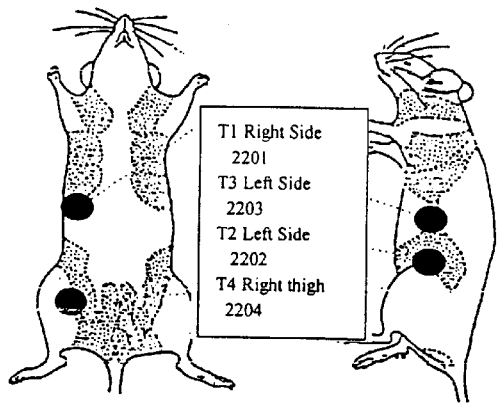
Figure 22B:
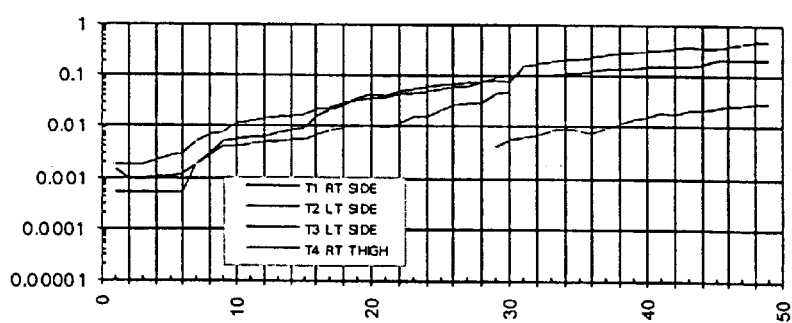
Figure 22C:
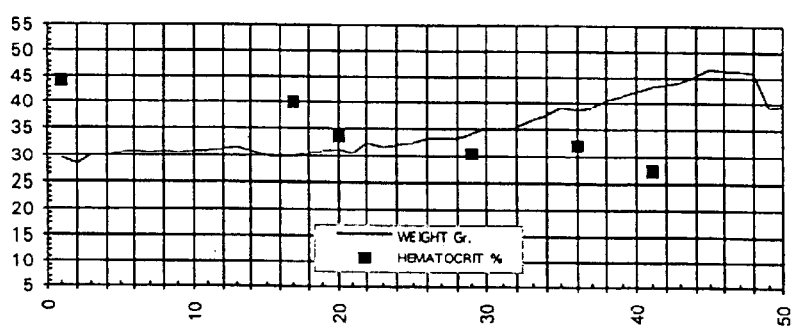

This mouse had four rapidly growing tumors and lived only fifty days after the first tumor appeared (FIG. 22B). After 20 days her weight increased and hematocrit reading steadily dropped (FIG. 22C).

EXAMPLE 14

Control Mouse A-492

TABLE 18

Summary for A-492

| | |
|---|---|
| Date of Birth: | Dec. 19, 1994 |
| Date died: | Dec. 29, 1995 |
| Lived: | 375 days |
| Treated: | Not treated |
| Tumor measurements started: | Sep. 15, 1995 |
| Tumor measurements taken for: | 105 days |

Figure 23A:
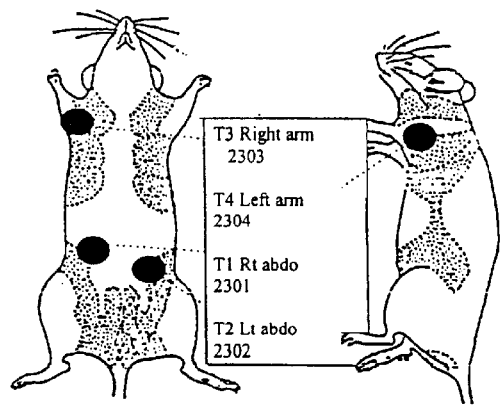
Figure 23B:
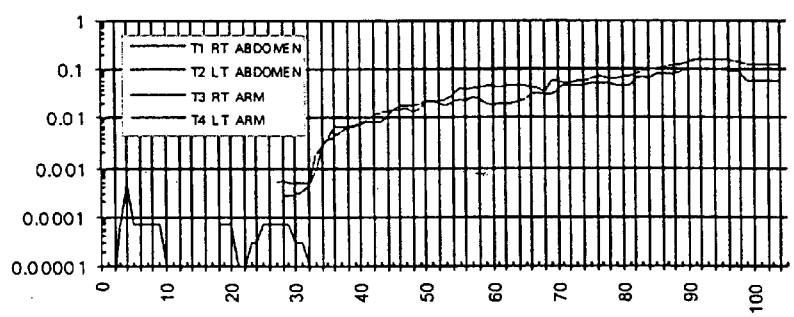
Figure 23C:
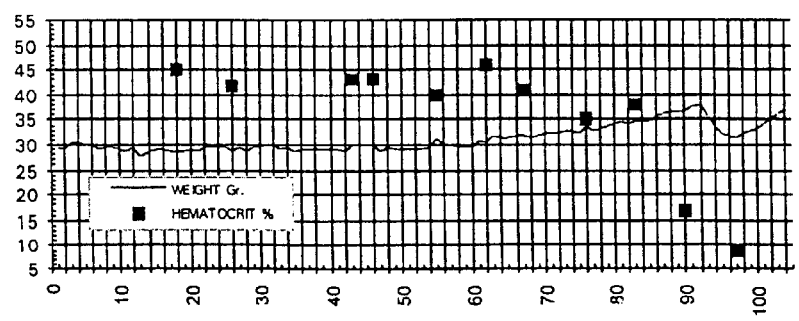

At 375 days, this is the longest lived control mouse. (Nine of our ten treated mice lived longer.) She had two tumors that left (FIG. 23B). But, after thirty days, T3 2303 and T4 2304 appeared and started to grow very rapidly. Her hematocrits dropped rapidly after 70 days of measurements (FIG. 23C).

EXAMPLE 15

Control Mouse A-500

TABLE 19

Summary for A-500

| | |
|---|---|
| Date of Birth: | Jan. 04, 1995 |
| Date died: | Oct. 11, 1995 |
| Lived: | 280 days |
| Treated: | Not treated |
| Tumor measurements started: | Sep. 15, 1995 |
| Tumor measurements taken for: | 26 days |

Figure 24A:
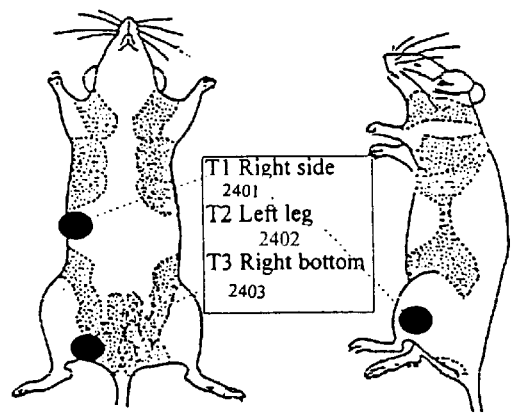
Figure 24B:
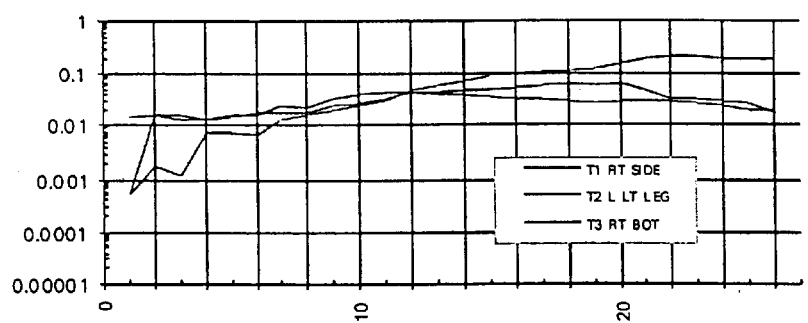
Figure 24C:
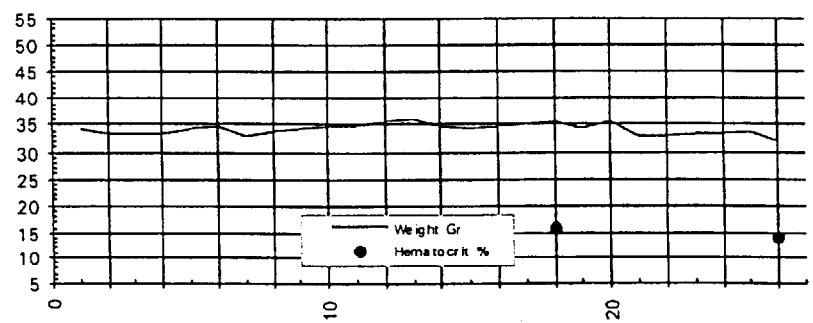

This mouse did not live very long and was observed only twenty-six days then she died. Tumors grew rapidly (FIG. 24B) and hematocrits were quite low (FIG. 24C).

EXAMPLE 16

Control Mouse A-538

TABLE 20

Summary for A-538

| | |
|---|---|
| Date of Birth: | Mar. 24, 1995 |
| Date died: | Jan. 15, 1996 |
| Lived: | 297 days |
| Treated: | Not treated |

TABLE 20-continued

Summary for A-538

| | |
|---|---|
| Tumor measurements started: | Oct. 19, 1995 |
| Tumor measurements taken for: | 88 days |

Figure 25A:
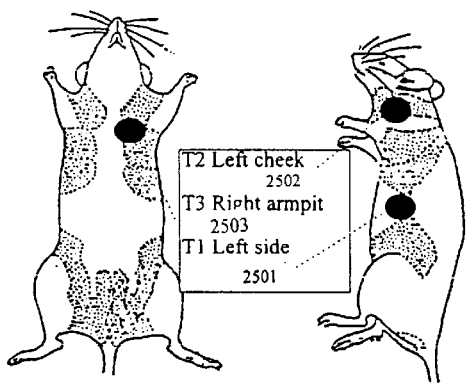
Figure 25B:
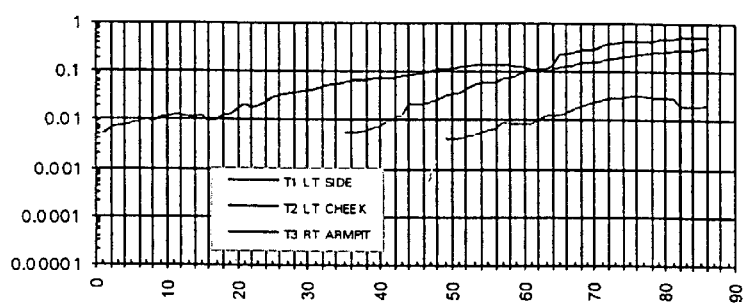
Figure 25C:
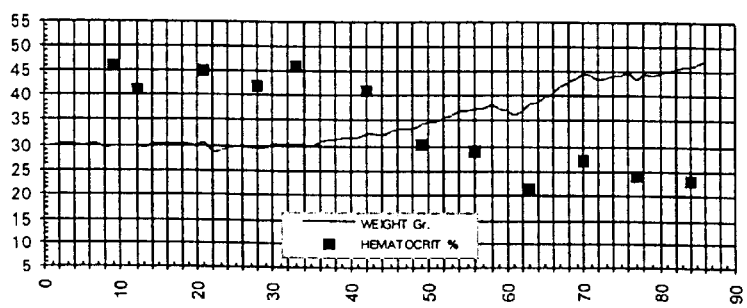

This mouse had three large tumors (FIG. 25B) and rapid weight increase and very low hematocrit percent readings (FIG. 25C). This mouse also did not live very long and was quite unhealthy.

EXAMPLE 17

Control Mouse A-540

TABLE 21

Summary for A-540

| | |
|---|---|
| Date of Birth: | Mar. 25, 1995 |
| Date died: | Jan. 02 1996 |
| Lived: | 283 days |
| Treated: | Not treated |
| Tumor measurements started: | Nov. 15, 1995 |
| Tumor measurements taken for: | 48 days |

Figure 26A:
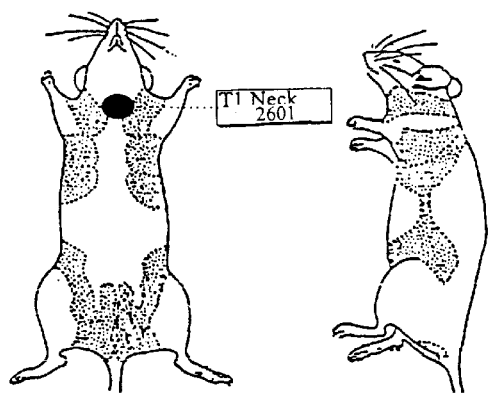
Figure 26B:
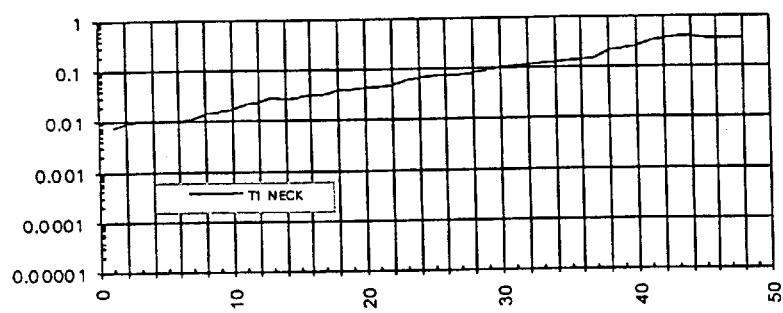
Figure 26C:
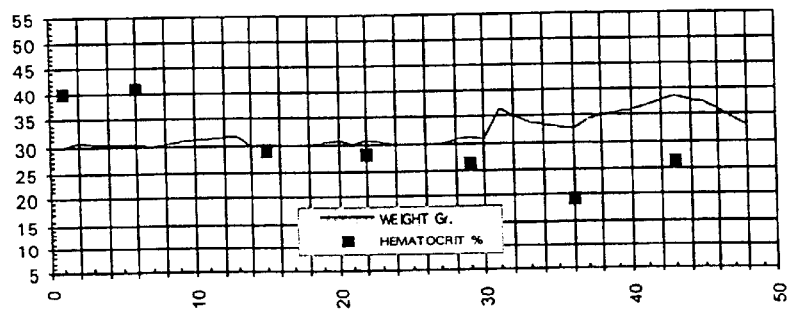

This mouse had one tumor that grew to a large size and grew fast (FIG. 26B). Low hematocrits caused this mouse to die in a short period (FIG. 26C).

EXAMPLE 18

Control Mouse A-542

TABLE 22

Summary for A-542

| | |
|---|---|
| Date of Birth: | Mar. 25, 1995 |
| Date died: | Jan. 18, 1996 |
| Lived: | 299 days |
| Treated: | Not treated |
| Tumor measurements started: | Nov. 27, 1995 |
| Tumor measurements taken for: | 52 days |

Figure 27A:
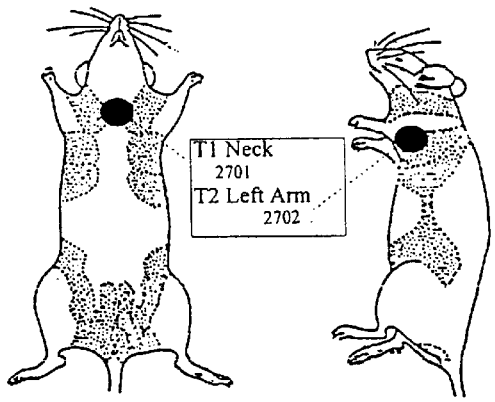
Figure 27B:
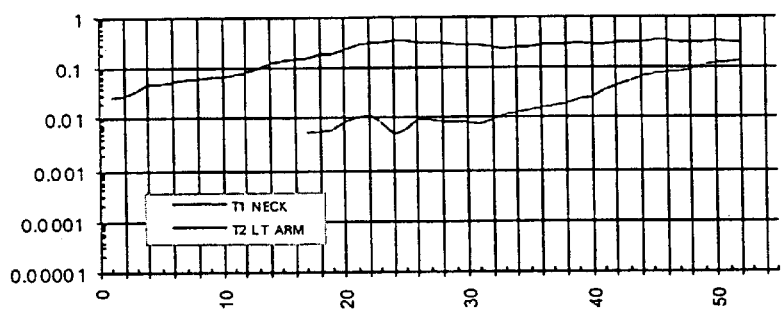
Figure 27C:
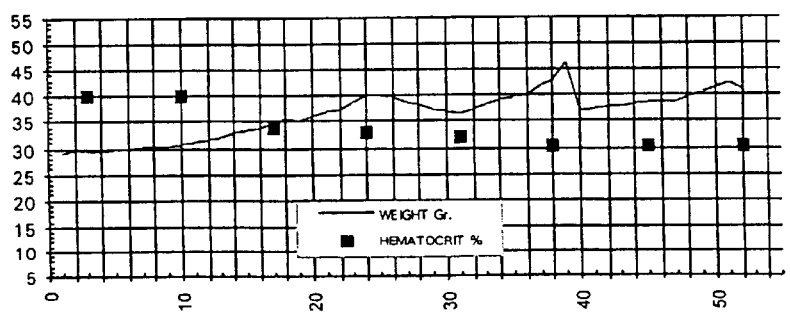

This mouse had two tumors that grew to a large size and grew fast (FIG. 27B). Weight continued to increase as the tumors grew (FIG. 27C). A tumor size of 0.1 to 0.5 cubic inches on a mouse this small is quite a burden for the mouse. They do not survive for long with tumors that size.

EXAMPLE 19

Control Mouse A-592

TABLE 23

Summary for A-592

| | |
|---|---|
| Date of Birth: | Jun. 27, 1995 |
| Date died: | Feb. 14, 1996 |
| Lived: | 232 days |

TABLE 23-continued

Summary for A-592

| Treated: | Not treated |
|---|---|
| Tumor measurements started: | Jan. 19, 1996 |
| Tumor measurements taken for: | 26 days |

Figure 28A:
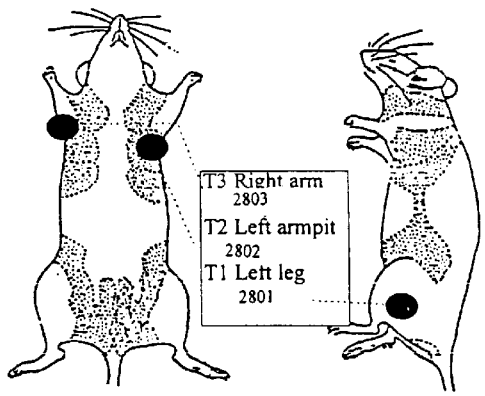
Figure 28B:
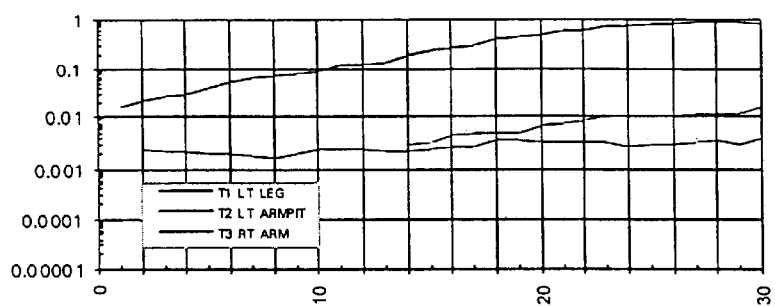
Figure 28C:
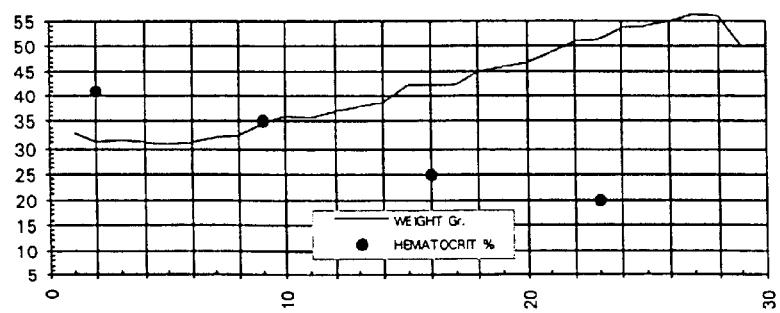

This mouse had one tumor that grew to a one cubic inch in size and grew fast (FIG. 28B). Rapid decline in hematocrits caused this mouse to die in a short period (FIG. 28C). Notice the rapid increase in weight: the mouse nearly doubled in weight in twenty days. This was a very short-lived mouse.

EXAMPLE 20

Control Mouse A-594

TABLE 24

Summary for A-594

| Date of Birth: | Jun. 27, 1995 |
|---|---|
| Date died: | Feb. 15, 1996 |
| Lived: | 233 days |
| Treated: | Not treated |
| Tumor measurements started: | Jan. 12, 1996 |
| Tumor measurements taken for: | 34 days |

Figure 29A:
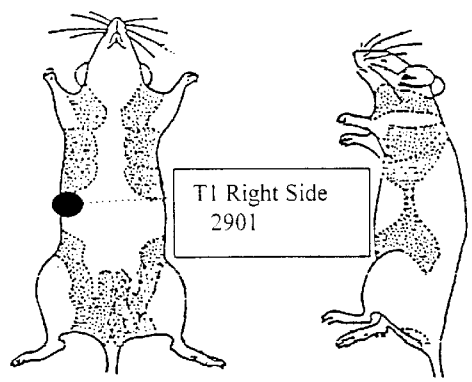
Figure 29B:
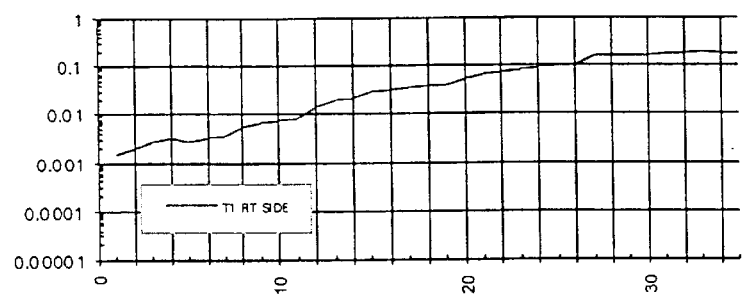
Figure 29C:
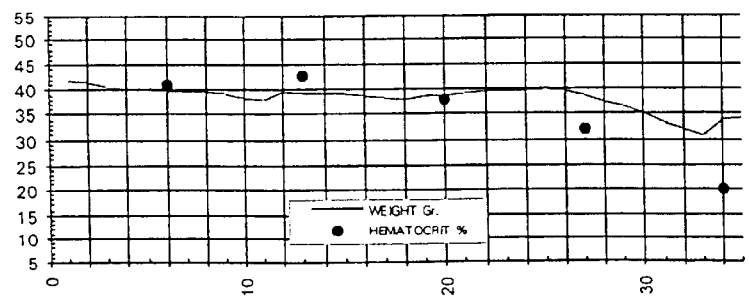

This mouse also had one tumor that grew to a large size and grew fast (FIG. 29B). Rapidly declining hematocrits caused this mouse to die in a short period (FIG. 29C). This is one of the shortest-lived control mice of the group.

Experimental Conclusions

Our principal conclusion, based on the experiments described above, is that the cancer-prone JAX mice benefited considerably from the therapeutic apparatus and method of the present invention. The subsidiary experimental conclusions that support this assertion are as follows:

1. Total Days of Life: Treated Mice Live 50% Longer

Figure 30A:
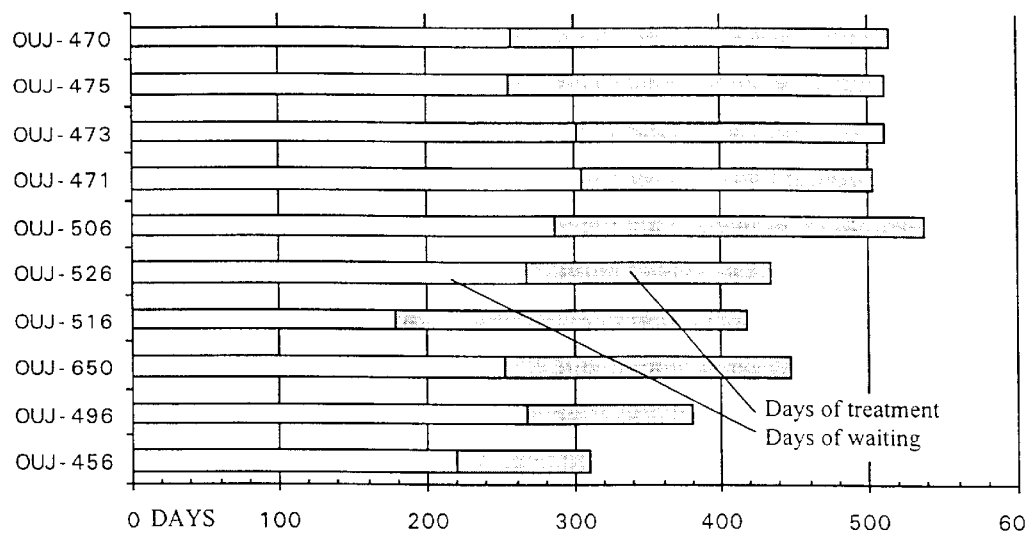
FIG. 30A and B shows bar graphs of the life spans of the treated and control mice, respectively.
Figure 30B:
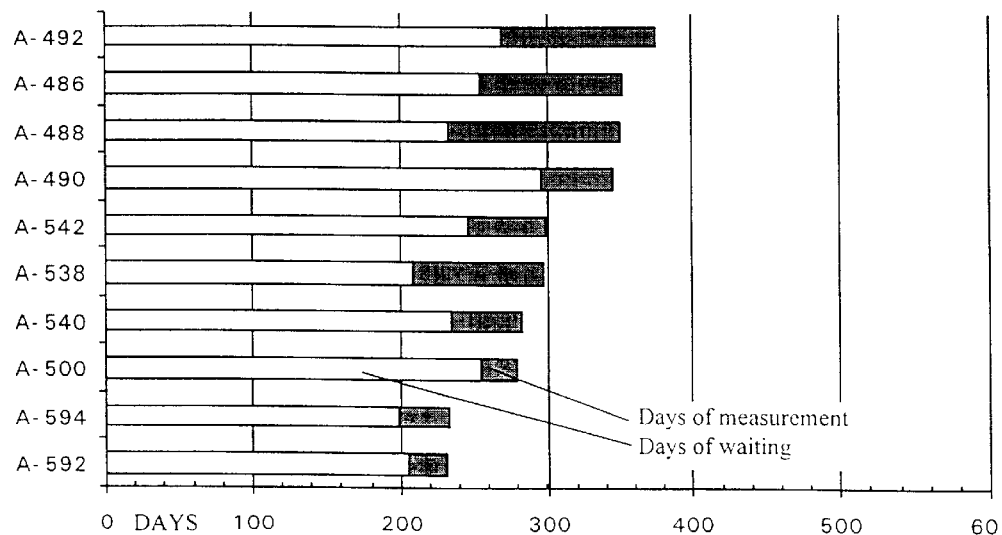

The bar-graphs in FIG. 30 show that the treated mice lived approximately 50% longer on average than the controls. Each bar indicates: Days of Waiting 3001, Days of Treatment (or Measurement) 3002, 3003, and Total Days Of Life 3004.

The data underlying FIG. 30 (as well as FIGS. 31 and 32, discussed below) is presented below in tabular form.

TABLE 25

Days of Life, Measurement, and Number of Tumors

| SUBJECT | NON MEASURED DAYS | MEASURED DAYS | QTY OF TUMORS | TOTAL LIFE |
|---|---|---|---|---|
| OUJ-456 | 219 | 91 | 2 | 310 |
| OUJ-496 | 268 | 112 | 6 | 380 |
| OUJ-650 | 253 | 195 | 3 | 392 |
| OUJ-516 | 179 | 239 | 9 | 418 |
| OUJ-526 | 268 | 167 | 5 | 435 |
| OUJ-506 | 287 | 250 | 5 | 481 |
| OUJ-471 | 305 | 199 | 2 | 504 |
| OUJ-473 | 301 | 211 | 0 | 512 |
| OUJ-475 | 256 | 256 | 2 | 512 |
| OUJ-470 | 258 | 256 | 3 | 514 |
| Totals: | 2594 | 1976 | 37 | 4,458 |
| A-592 | 206 | 26 | 3 | 232 |
| A-594 | 199 | 34 | 1 | 233 |
| A-500 | 254 | 26 | 3 | 280 |
| A-540 | 235 | 48 | 1 | 283 |
| A-538 | 209 | 88 | 3 | 297 |
| A-542 | 247 | 52 | 2 | 299 |
| A-490 | 296 | 49 | 4 | 345 |
| A-488 | 234 | 116 | 4 | 350 |
| A-486 | 255 | 97 | 2 | 352 |
| A-492 | 270 | 105 | 4 | 375 |
| Totals: | 2405 | 641 | 27 | 3,046 |

Figure 31A:
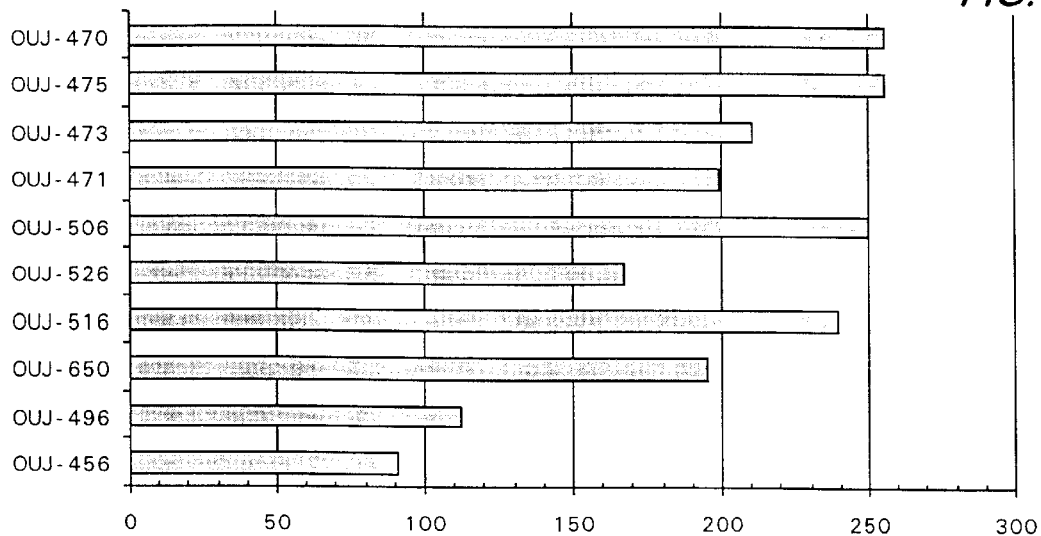
FIG. 31A and B shows bar graphs of the life spans of the treated and control mice, respectively, after tumors were detected.
Figure 31B:
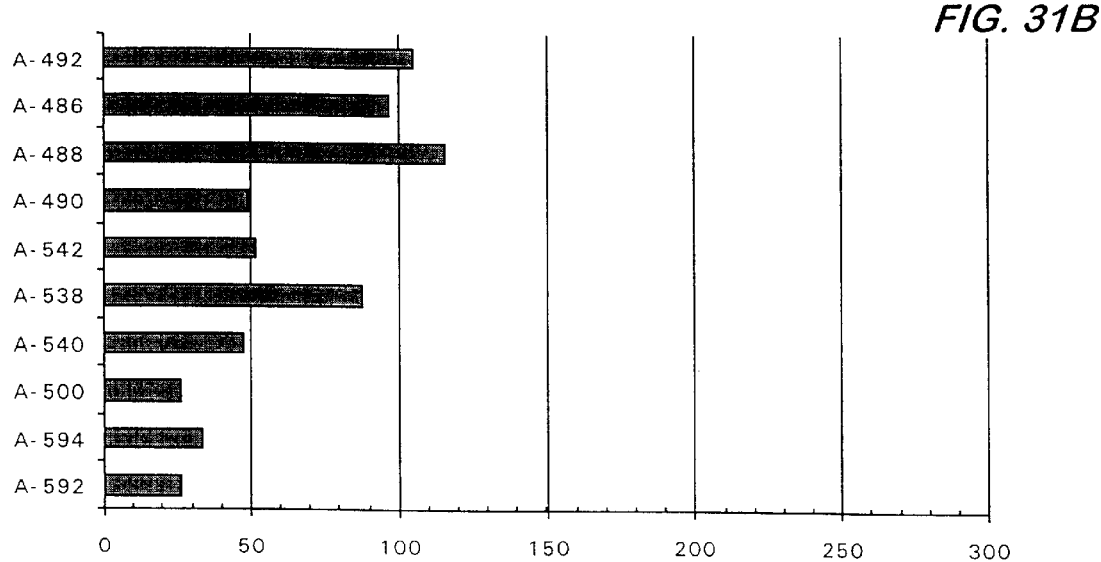

2. Starting Treatment After First Tumor Appears: Treated Mice Live More than 300% Longer FIG. 31 shows that after the first tumor appeared, the treated mice lived longer than the control mice. The bars in these graphs represent Days of Treatment for treated mice or Days of Measurement for control mice. The data underlying FIG. 31 is set forth in Table 25 above.

3. The Treated Mice Had More Tumors (by 37%), but They Lived Longer

Figure 32A:
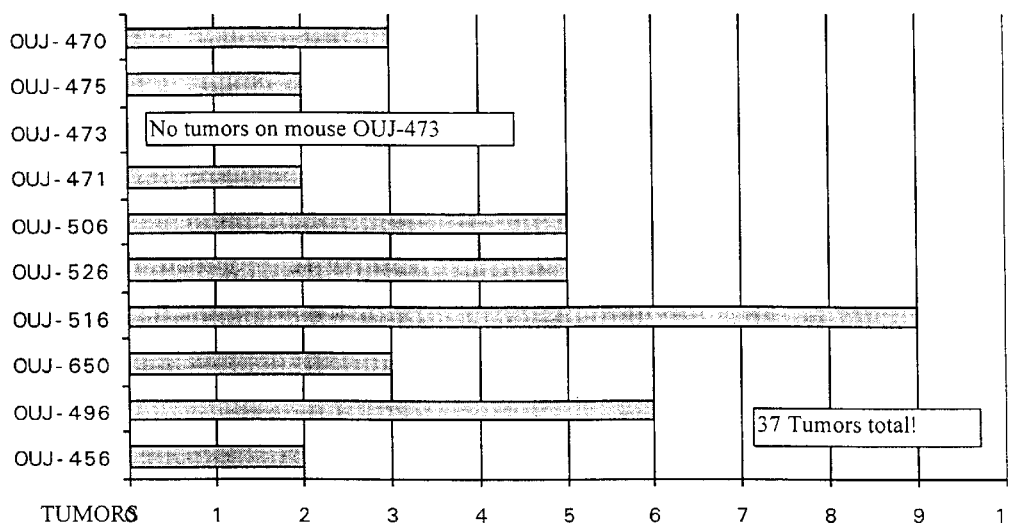
FIG. 32A and B shows bar graphs of the number of tumors in the treated and control mice, respectively.
Figure 32B:
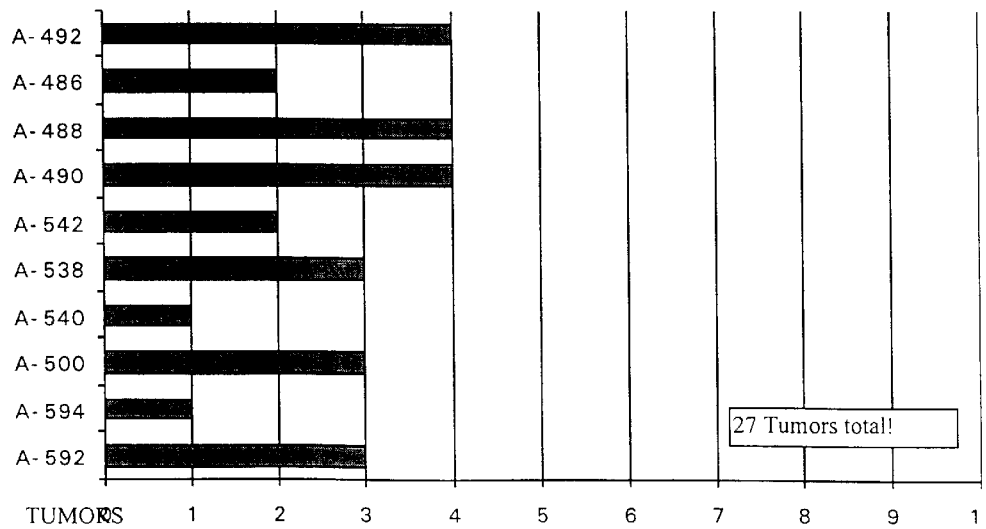

FIG. 32 shows the number of tumors that developed in each mouse. It must be noted that even though there were 37% more tumors in the treated mice, they lived longer than the controls. The data underlying FIG. 32 is set forth in Table 25 above.

4. Tumors that Appeared Were Five Times More Likely to Disappear in the Treated Mice than in the Controls.

Figure 33A:
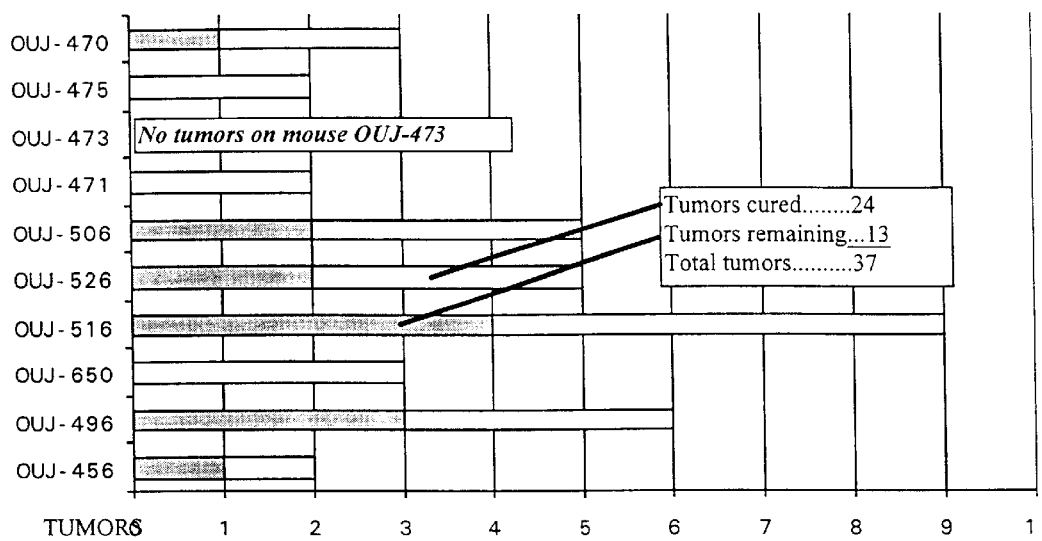
FIG. 33A and B shows bar graphs of the outcome with respect to the tumors found in the treated and control mice, respectively.
Figure 33B:
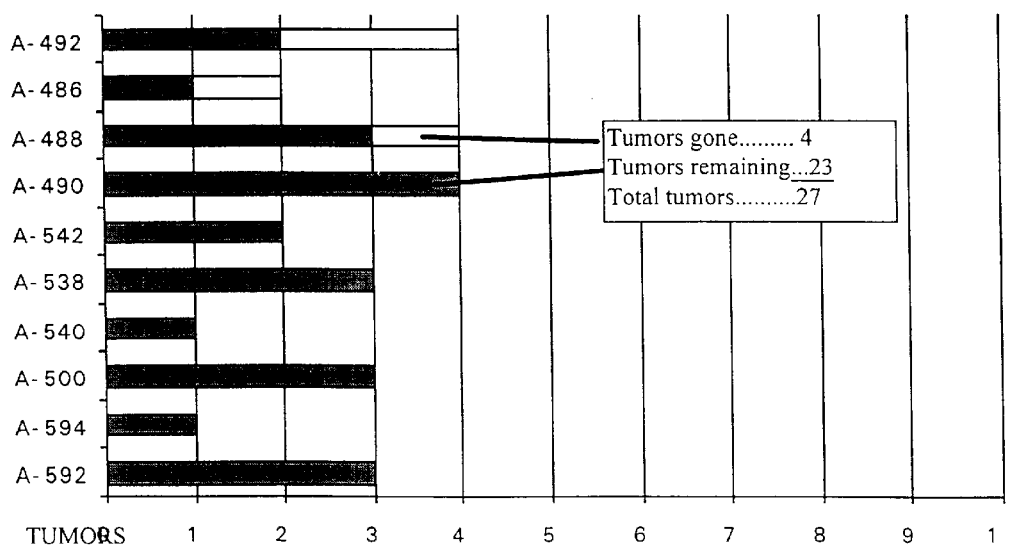

FIG. 33 shows the total number of tumors in each mouse, and those tumors that disappeared or were cured and the remaining tumors at the death of each mouse. (Note: OUJ-506 and OUJ-650 were still living as of Jun. 25, 1996, when this data was compiled.)

The data underlying FIG. 33 is set forth in Table 26 below.

TABLE 26

Tumors That Disappeared

| SUBJECT | MEASURED DAYS | REMAINING TUMORS | CURED/ GONE TUMORS | TOTAL LIFE | NON MEASURED DAYS |
|---|---|---|---|---|---|
| OUJ-456 | 91 | 1 | 1 | 310 | 219 |
| OUJ-496 | 112 | 3 | 3 | 380 | 268 |
| OUJ-650 | 195 | 0 | 3 | 448 | 253 |
| OUJ-516 | 239 | 4 | 5 | 418 | 179 |

TABLE 26-continued

Tumors That Disappeared

| SUBJECT | MEASURED DAYS | REMAINING TUMORS | CURED/GONE TUMORS | TOTAL LIFE | NON MEASURED DAYS |
|---|---|---|---|---|---|
| OUJ-526 | 167 | 2 | 3 | 435 | 268 |
| OUJ-506 | 250 | 2 | 3 | 537 | 287 |
| OUJ-471 | 199 | 0 | 2 | 504 | 305 |
| OUJ-473 | 211 | 0 | 0 | 512 | 301 |
| OUJ-475 | 256 | 0 | 2 | 512 | 256 |
| OUJ-470 | 256 | 1 | 2 | 514 | 258 |
| Totals: | 1976 | 13 | 24 | 4,570 | 2594 |
| A-592 | 26 | 3 | 0 | 232 | 206 |
| A-594 | 34 | 1 | 0 | 233 | 199 |
| A-500 | 26 | 3 | 0 | 280 | 254 |
| A-540 | 48 | 1 | 0 | 283 | 235 |
| A-538 | 88 | 3 | 0 | 297 | 209 |
| A-542 | 52 | 2 | 0 | 299 | 247 |
| A-490 | 49 | 4 | 0 | 345 | 296 |
| A-488 | 116 | 3 | 1 | 350 | 234 |

TABLE 26-continued

Tumors That Disappeared

| SUBJECT | MEASURED DAYS | REMAINING TUMORS | CURED/GONE TUMORS | TOTAL LIFE | NON MEASURED DAYS |
|---|---|---|---|---|---|
| A-486 | 97 | 1 | 1 | 352 | 255 |
| A-492 | 105 | 2 | 2 | 375 | 270 |
| Totals: | 641 | 23 | 4 | 3,046 | 2405 |

Figure 34A:
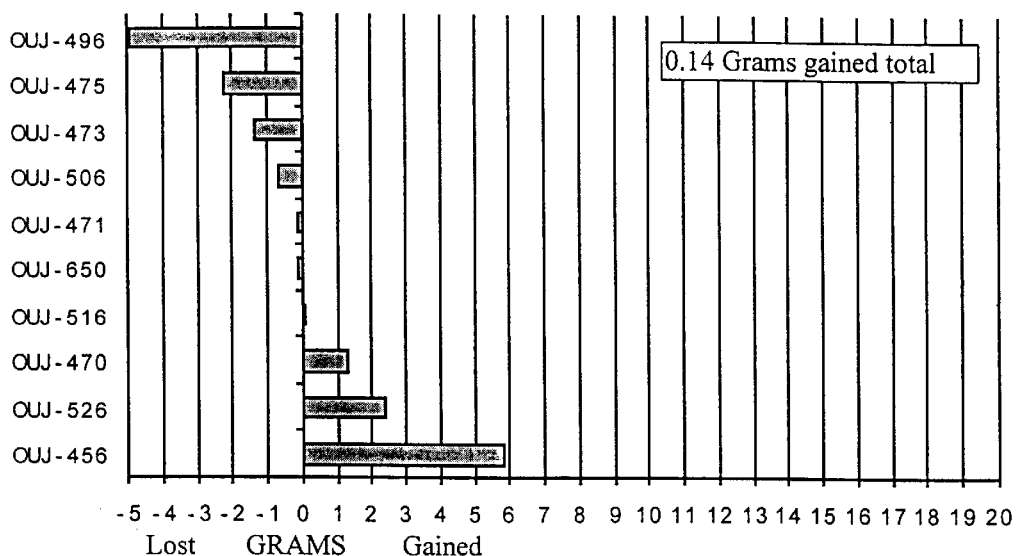
FIG. 34A and B shows bar graphs of the weight changes observed in the treated and control mice, respectively.
Figure 34B:
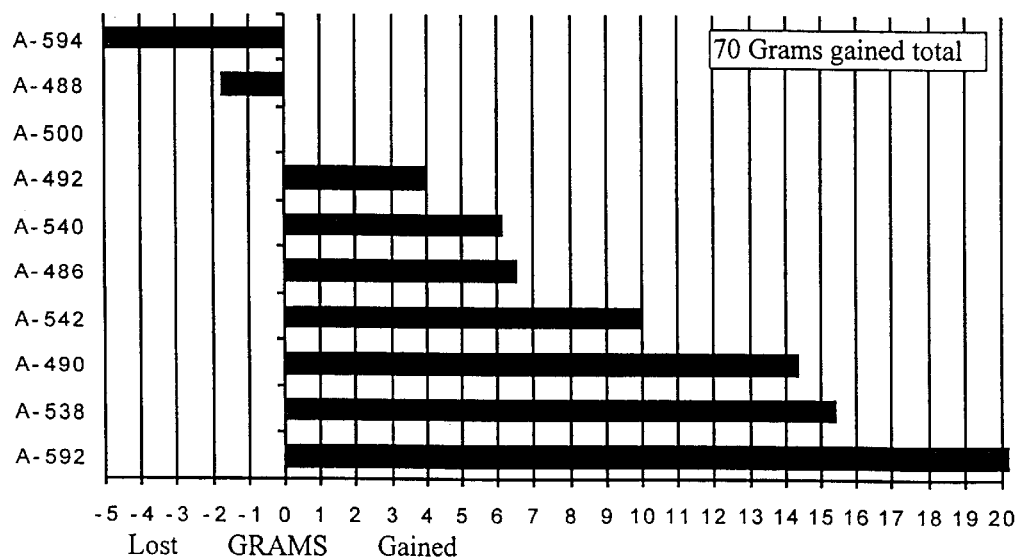

5. The Weight of the Treated Mice Remained Stable, Whereas the Control Mice Markedly Gained Weight FIG. 34 shows that the treated mice maintain their weight on average, while the control mice gain considerable weight due to tumor growth. (Note: The weight change shown is the last 10 day weight average minus the first 10 day weight average of each mouse.) The data underlying FIG. 34 is set forth in Table 27 below.

TABLE 27

Comparative Weight Changes

| Treated Mouse | Weight Change | Control Mouse | Weight Change |
|---|---|---|---|
| OUJ-456 | 5.85 | A-592 | 20.31 |
| OUJ-526 | 2.37 | A-538 | 15.42 |
| OUJ-470 | 1.31 | A-490 | 14.32 |
| OUJ-471 | −0.15 | A-542 | 9.97 |
| OUJ-473 | −1.36 | A-486 | 6.54 |
| OUJ-475 | −2.22 | A-540 | 6.15 |
| OUJ-506 | −0.66 | A-492 | 3.98 |
| OUJ-650 | −0.15 | A-500 | 0.02 |
| OUJ-516 | 0.07 | A-488 | −1.73 |
| OUJ-496 | −4.92 | A-594 | −4.92 |
| Totals: | 0.14 | | 70.06 |

6. The Control Mice Had More Large Tumors

Figure 35A:
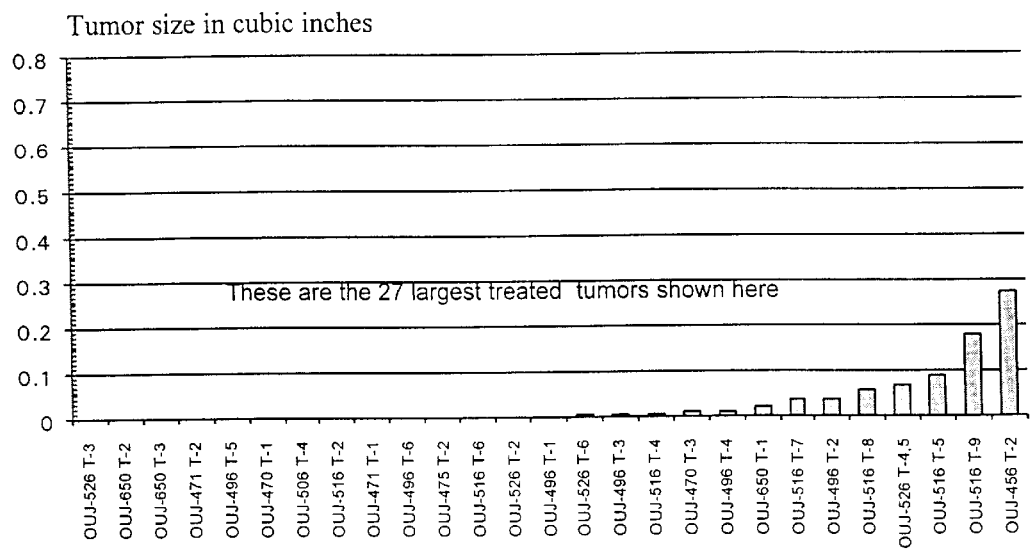
FIG. 35A and B shows bar graphs of the maximum size of tumors observed in the treated and control mice, respectively.
Figure 35B:
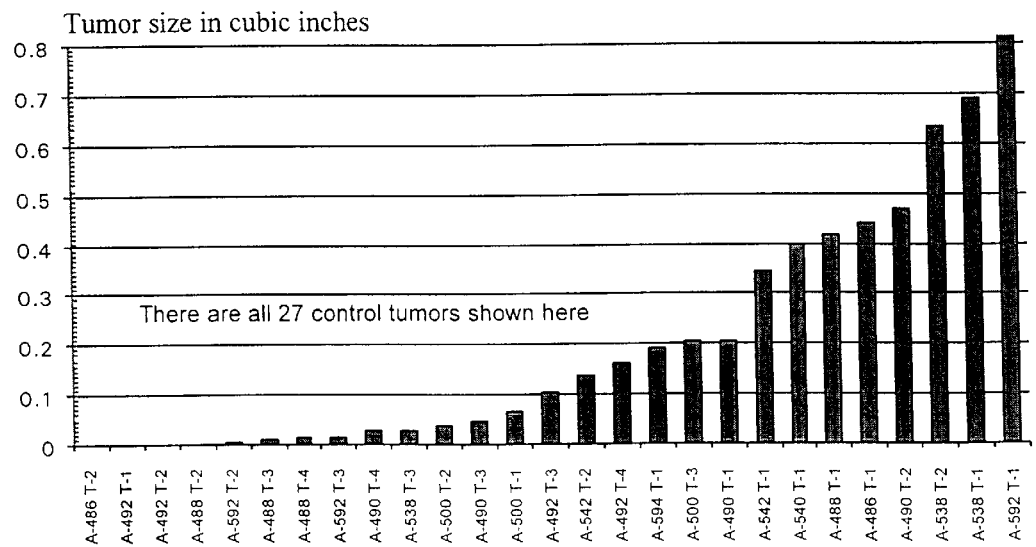

FIG. 35 shows the maximum sizes of each tumor on the twenty different mice. Some of these tumors disappeared. The vertical scale is tumor size in cubic inches. There were 37 treated and 27 control tumors but this graph shows the 27 largest treated tumors and all 27 control tumors.

The data underlying FIG. 35 is set forth in Tables 28A and B below.

TABLE 28A

Comparison of Maximum Tumor size (in cubic inches)

| Treated Subject | Tumor 1 | Tumor 2 | Tumor 3 | Tumor 4 | Tumor 5 | Tumor 6 | Tumor 7 | Tumor 8 | Tumor 9 |
|---|---|---|---|---|---|---|---|---|---|
| OUJ-456 | 0.00001413 | 0.27320000 | | | | | | | |
| OUJ-470 | 0.00017960 | 0.00001413 | 0.00954900 | | | | | | |
| OUJ-471 | 0.00026180 | 0.00009161 | | | | | | | |
| OUJ-473 | | | | | | | | | |
| OUJ-475 | 0.00001413 | 0.00036650 | | | | | | | |
| OUJ-496 | 0.00117800 | 0.03799000 | 0.00633200 | 0.01099000 | 0.00015390 | 0.00029680 | | | |
| OUJ-506 | 0.00001413 | 0.01866000 | 0.00001413 | 0.00017960 | 0.01682000 | | | | |
| OUJ-516 | 0.00001413 | 0.00017960 | 0.00006544 | 0.00653300 | 0.08179000 | 0.00048370 | 0.03624000 | 0.05560000 | 0.17990000 |
| OUJ-526 | 0.00001413 | 0.00082920 | 0.00006544 | 0.06579000 | 0.00533600 | | | | |
| OUJ-650 | 0.00241900 | 0.00006544 | 0.00006544 | | | | | | |
| Total | 0.00410800 | 0.33140000 | 0.01609000 | 0.08349000 | 0.10410000 | 0.00078050 | 0.03624000 | 0.05560000 | 0.17990000 |
| Average | 0.00045650 | 0.03682000 | 0.00268200 | 0.02087000 | 0.02603000 | 0.00039030 | 0.03624000 | 0.05560000 | 0.17990000 |

TABLE 28B

Comparison of Maximum Tumor Size (in cubic inches)

| Control Subject | Tumor 1 | Tumor 2 | Tumor 3 | Tumor 4 |
|---|---|---|---|---|
| A-486 | 0.43920000 | 0.00001413 | | |
| A-488 | 0.41790000 | 0.00619300 | 0.00762200 | 0.01493000 |
| A-490 | 0.20800000 | 0.47080000 | 0.04913000 | 0.02954000 |
| A-492 | 0.00052350 | 0.00006544 | 0.10690000 | 0.16280000 |
| A-500 | 0.06478000 | 0.04252000 | 0.20560000 | |
| A-538 | 0.56350000 | 0.32310000 | 0.03216000 | |
| A-540 | 0.39520000 | | | |
| A-542 | 0.36820000 | 0.13700000 | | |
| A-592 | 0.81920000 | 0.00419200 | 0.01504000 | |
| A-594 | 0.19090000 | | | |
| Total | 3.46700000 | 0.98380000 | 0.41640000 | 0.20730000 |
| Average | 0.34670000 | 0.12300000 | 0.06940000 | 0.06910000 |

Test of Externally Pulsed Generator

Figure 8B:
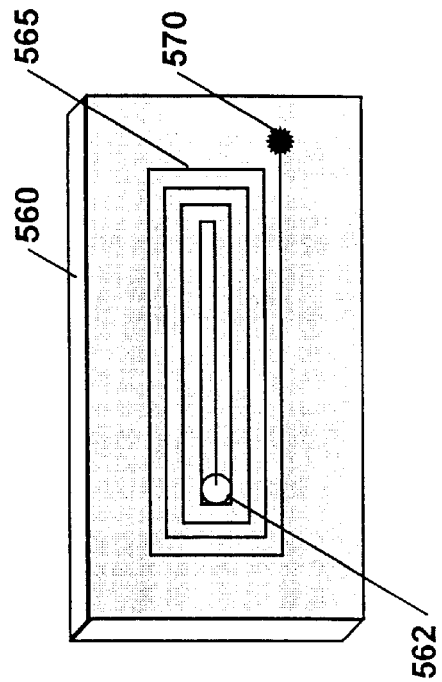
FIGS. 8A and 8B show front and back views of the treatment loop used in connection with the Generator Embodiment.
Figure 8A:
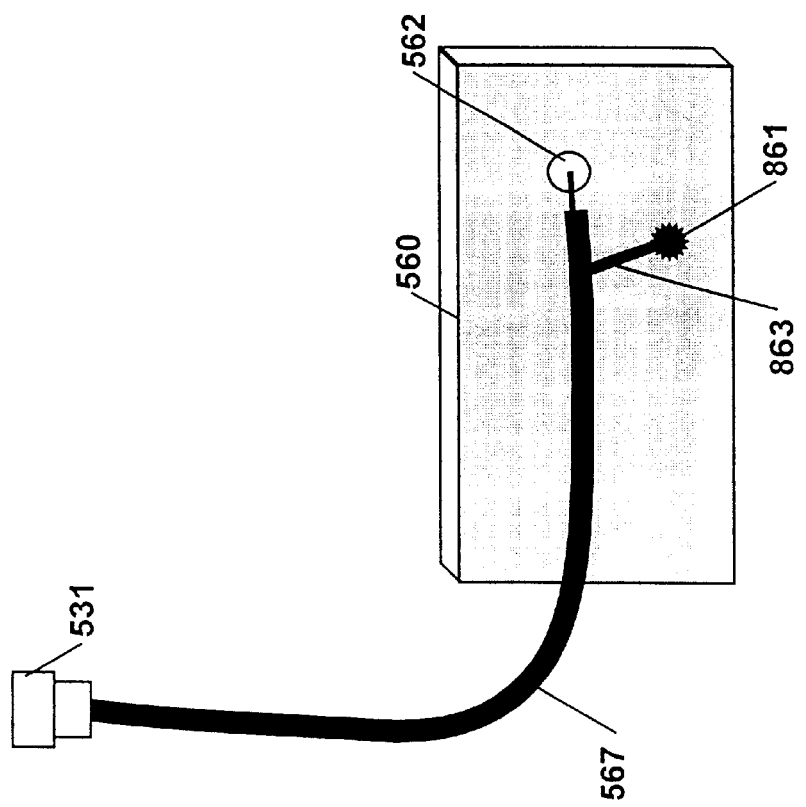
Figure 9A:
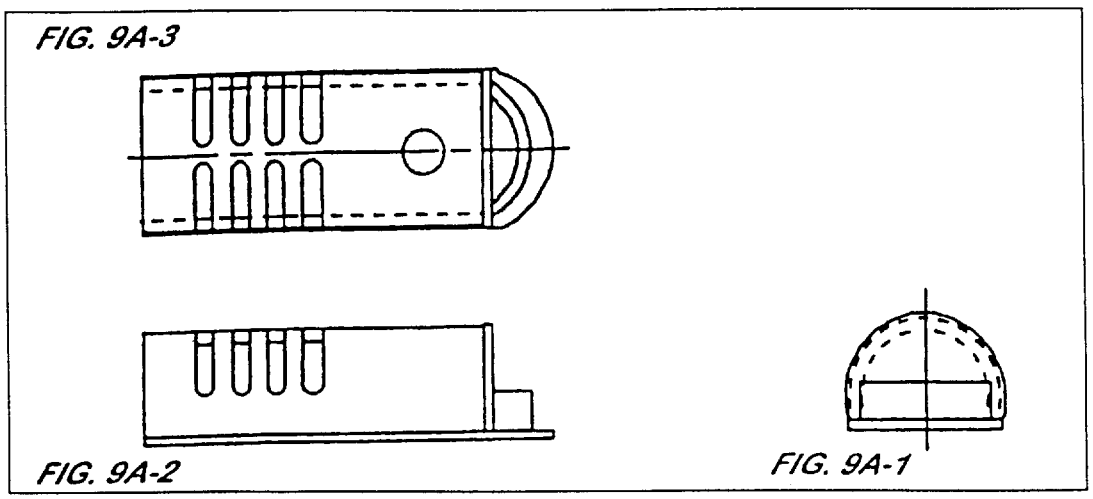
Figure 9B:
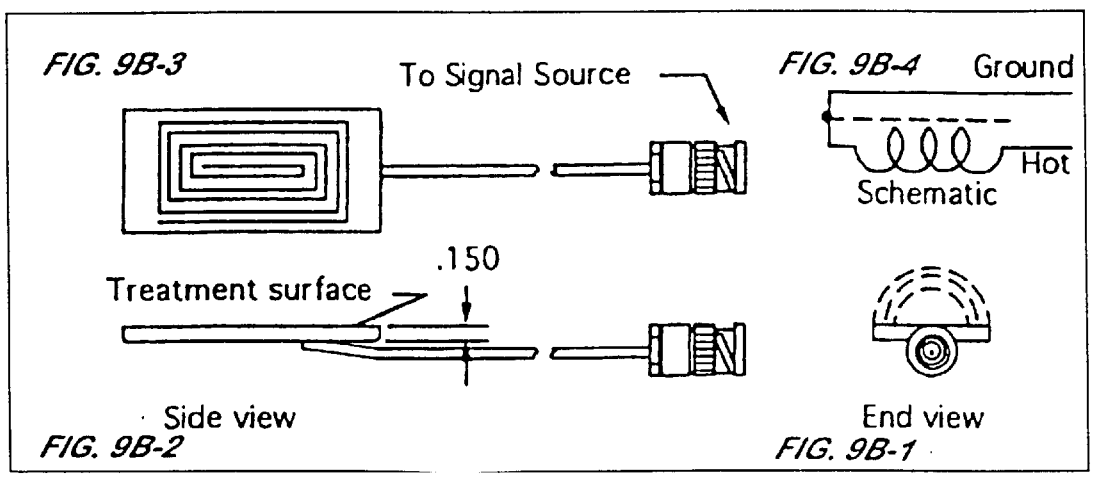
Figure 9C:
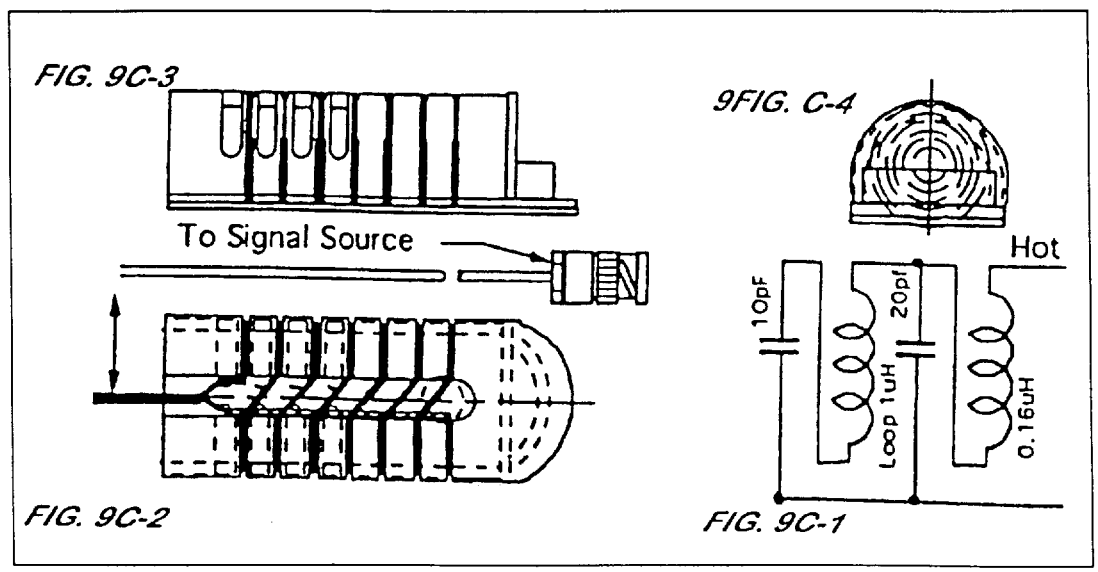
Figure 9D:
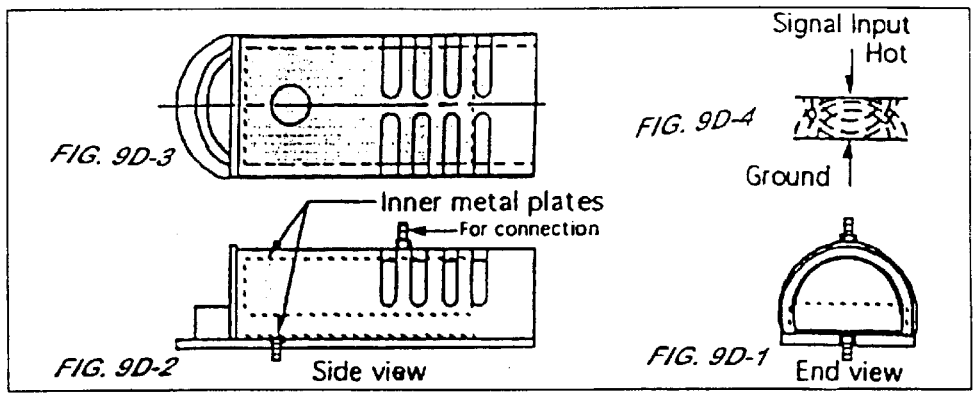
Figure 9E:
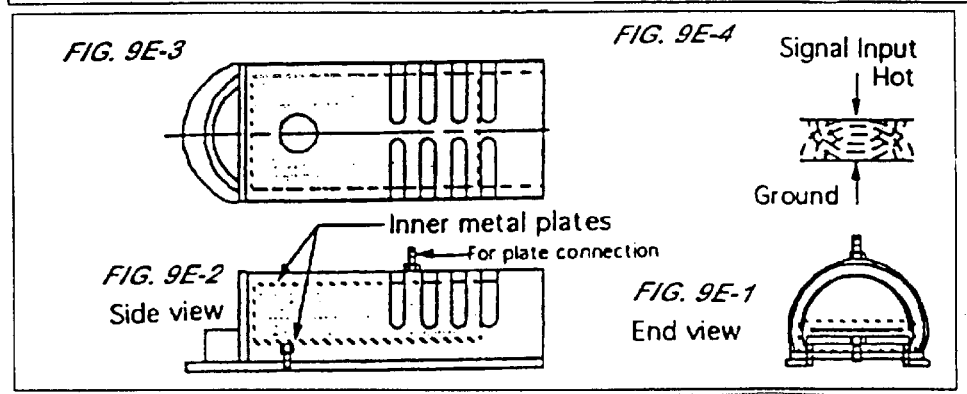
Figure 9F:
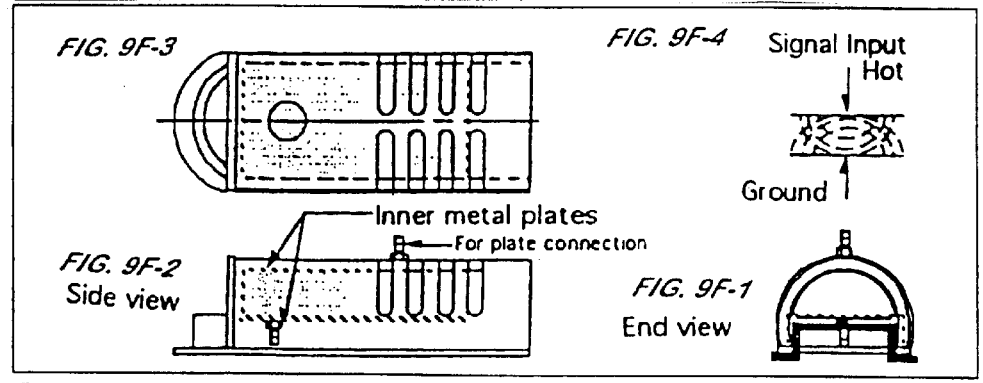
Figure 9G:
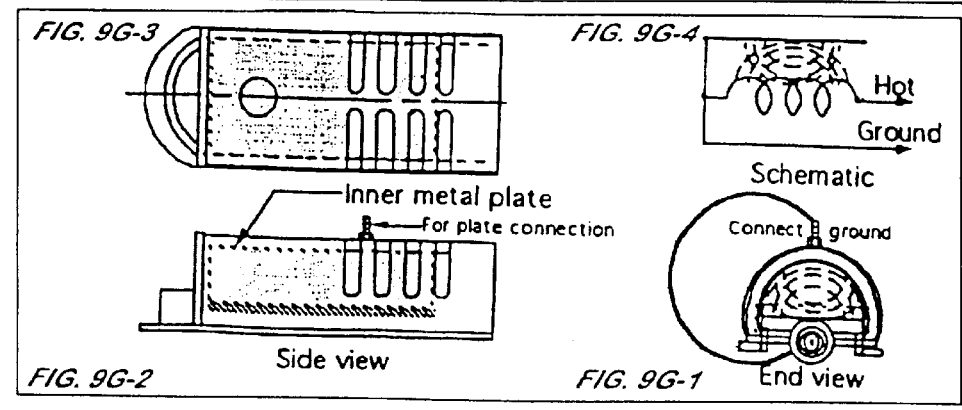
Figure 9H:
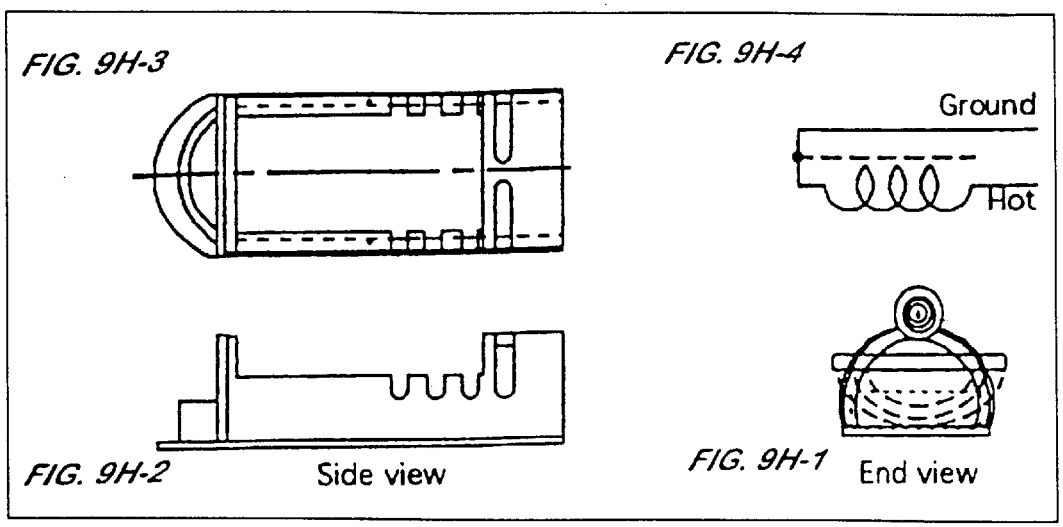
Figure 9I:
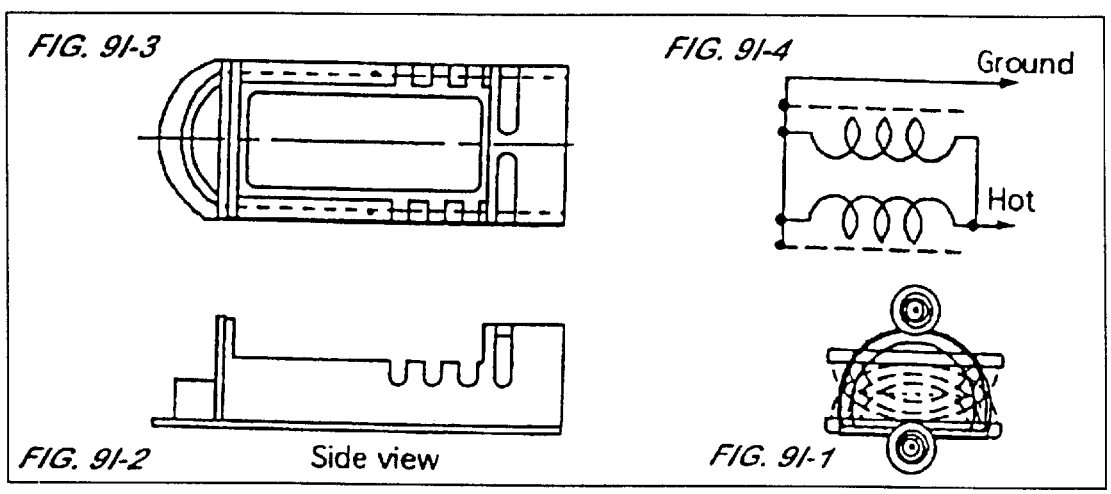
Figure 9J:
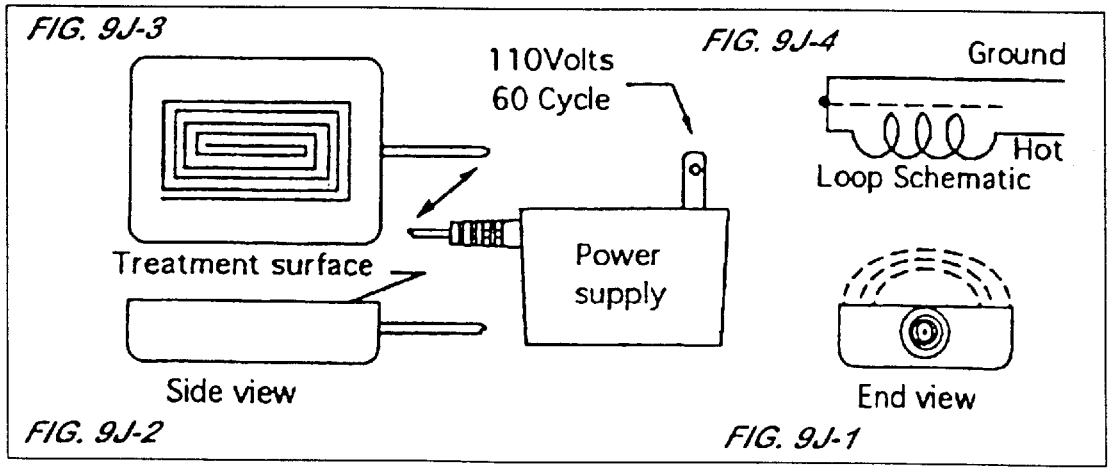

FIG. 37 shows the results of treating mouse OUJ-738 in 1997 with the Externally Pulsed Generator embodiment. Treatment was with the HP 8662A frequency generator externally modulated with the modulator shown in FIG. 36, coupled to a treatment loop as shown in FIGS. 8A and 8B deployed in the "E" housing shown in FIG. 9A. The corresponding experimental data is shown in Appendix C.

Figure 37A:
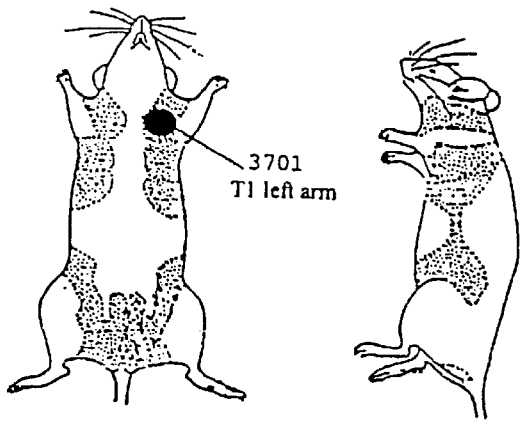
FIG. 37 shows, for a mouse treated with a Generator Embodiment pulsed externally by the modulator shown in FIG. 36, A, the location of the tumor that developed, B, plots (on a logarithmic scale) of tumor volume as a function of time, and C, plots of the mouse's weight and hematocrit measurements as a function of time.
Figure 37B:
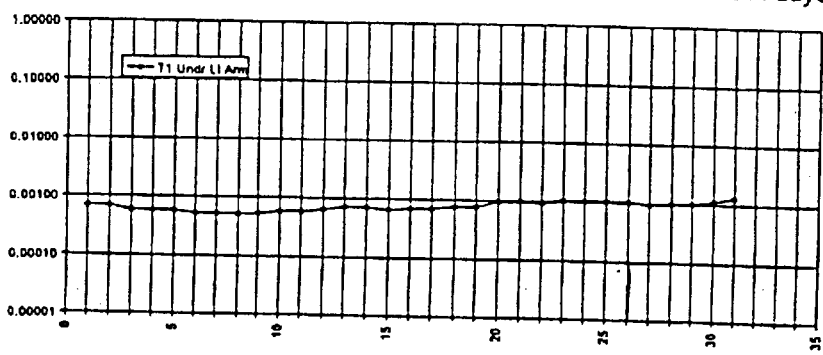
Figure 37C:
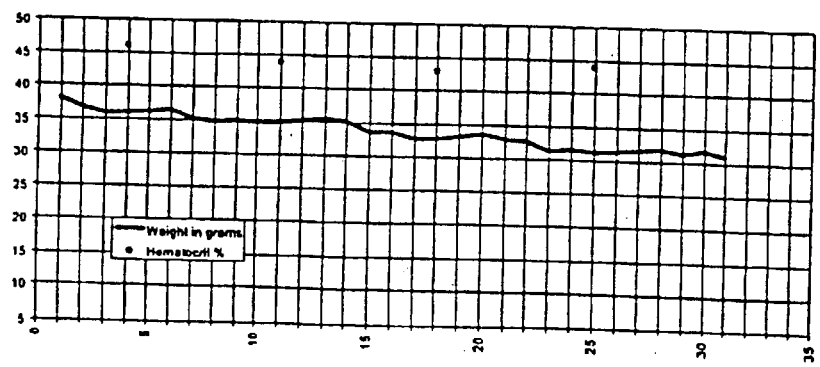

FIG. 37A shows that a single tumor T1 3701 developed on this mouse in the left arm position. This position is difficult to treat because it is out of the way and as a consequence it is difficult to position the treatment electrode close to the tumor. Nevertheless, the results with this mouse were extremely good for the period of testing. As shown in FIG. 37B, the tumor stayed small for the entire period, and as shown in FIG. 37C, the weight was stable and the hematocrits remained high. The data extends up to a few days prior to the filing of this application, and at the end of this period the mouse was alive and healthy.

In addition, data were compiled in 1997 with respect to tumors that disappeared after treatment with the generator embodiment. This data, which otherwise appears in the Figures hereto, is as follows:

TABLE 29

Disappearance of Tumors on Mice Treated with HP 8662A Frequency Generator Embodiment

| Treated Mouse # | Tumor 1 | Tumor 2 | Tumor 3 | Tumor 4 | Tumor 5 | Tumor 6 |
|---|---|---|---|---|---|---|
| OUJ-650 | Yes | Yes | Yes | | | |
| OUJ-526 | Yes | Yes | Yes | | | |
| OUJ-516 | Yes | Yes | Yes | Yes | | Yes |
| OUJ-506 | Yes | Yes | Yes | Yes | | |
| OUJ-496 | Yes | | | | Yes | |
| OUJ-471 | Yes | Yes | | | | |
| OUJ-470 | Yes | Yes | | | | |
| OUJ-456 | Yes | | | | | |

It is apparent from the foregoing that a new treatment has been developed which has shown great effectiveness in treating cancer and other illnesses in laboratory mice and is believed to be a promising treatment for humans. While only presently preferred embodiments have been described in detail, it will be apparent to those skilled in the art that certain changes and modifications can be made without departing from the scope of the invention, as defined in the following claims.

II. Preferred Embodiments for the Diagnostic Elements of the Present Invention:

Radioscope Wiring Diagram.

Following are several pages devoted to the wiring diagram, assembly and part details of the Radioscope.

Figure 39:
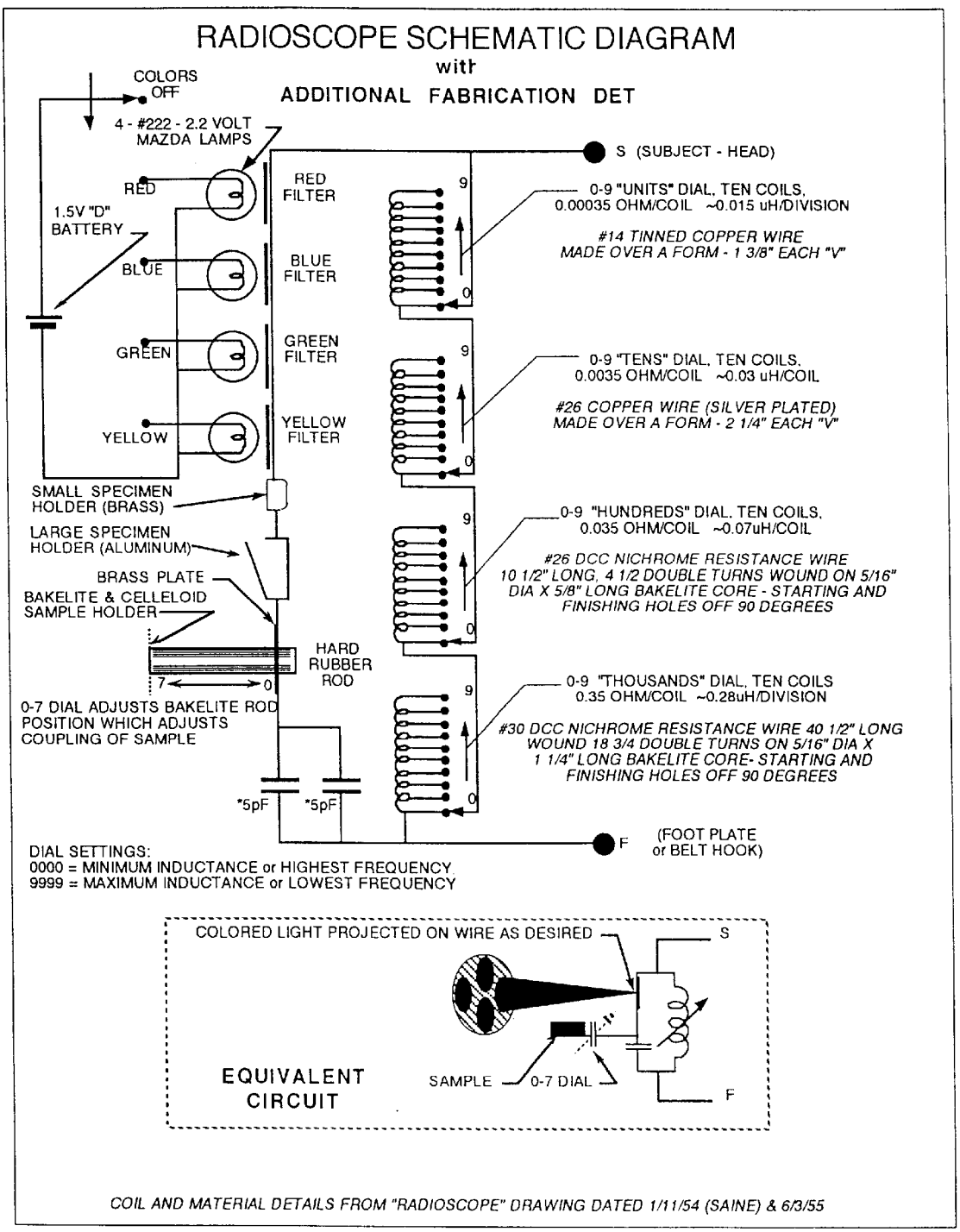
FIG. 39 shows the three basic circuits of the Radioscope schematic diagram.

FIG. 39 shows schematically three basic circuits. The first circuit is the battery and lamp circuit. This circuit allows any one of four colored lights to be switched on to shine on the wire between the small specimen cup and the "S" (subject) terminal. The second circuit shows the parallel (switched) inductor and fixed capacitor that makes up the tuned circuit for disease detection. The third circuit is a simplified equivalent circuit showing a location for the blood sample, the coupling of the sample to the tuned circuit represented by a variable capacitor and then the tuned circuit represented by a fixed capacitor and a variable (switched) inductor. Some additional details are included i.e. component values.

Reagent Connection to Radioscope.

Figure 40:
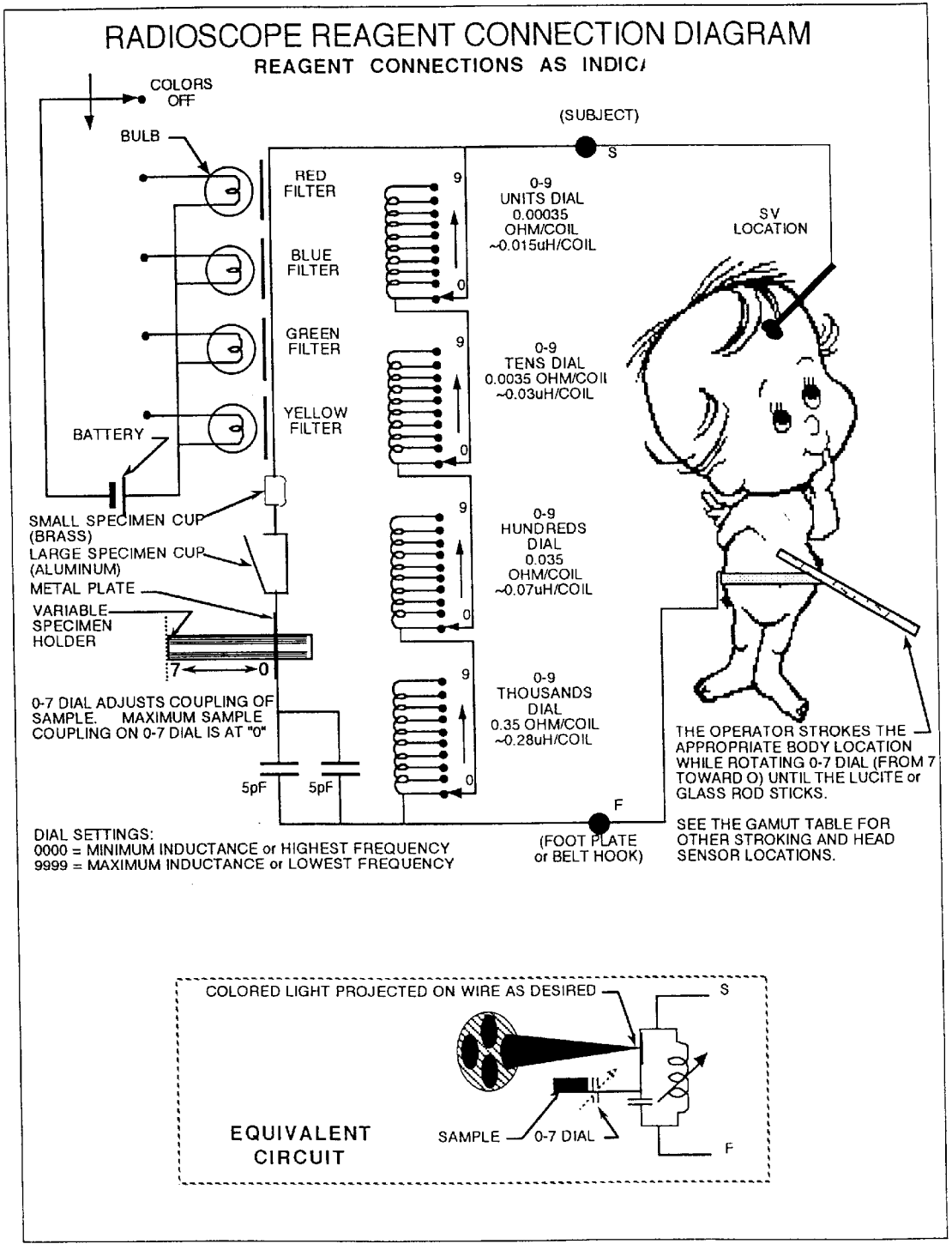
FIG. 40 shows the Radioscope connections to the reagent diagram.

FIG. 40 has many of the same details as FIG. 39 except, we schematically show how the Radioscope connects to the reagent.

Construction of the Radioscope.

Figure 41:
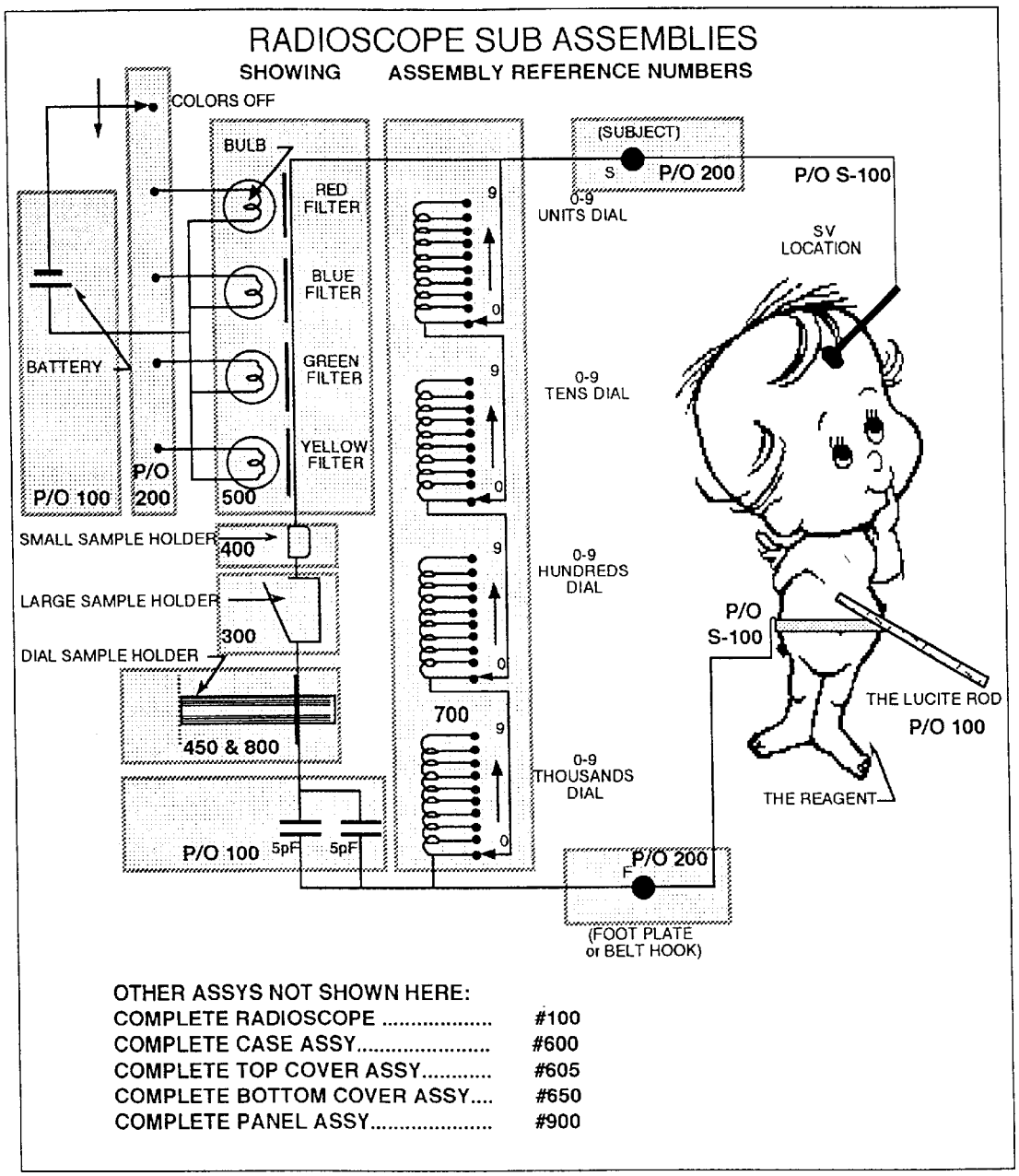
FIG. 41 shows the Radioscope sub-assembly overview and numbering.

FIG. 41 shows an overview of the subassembly numbering system for the Radioscope. TABLE 30 lists all the parts, quantity and assembly numbers used in the Radioscope. Most of the parts for this unit were custom made and fabricated from raw material. They are not "off the shelf" from any electronic or hardware outlet. Each part is described in some detail in the pages of drawings. Most part dimensions are shown so the reader can get a general idea of the part's size and shape. Material is also noted on each drawing.

TABLE 30

Parts List for Radioscope

| # | Part Name & Description | Qty Used | Next Ay # | FIG. | Item |
|---|---|---|---|---|---|
| 100 | Complete Radioscope | 1 | None | 55, 56 | Text Dwg |
| 110 | Battery Clamp | 1 | 100 | 59 | 1 |
| 115 | Battery Clamp Nut | 1 | 100 | 59 | 2 |
| 120 | Battery 1.5 Volts | 1 | 100 | 59 | 3 |
| 125 | #6 Wood Screw | 4 | 100 | 59 | 4 |
| 130 | 5 pF Fixed Capacitor | 2 | 100 | 60 | 1 |
| 135 | Glass or Lucite Stroking Rod | 1 | 100 | 60 | 2 |
| 200 | Binding Post & Lamp Switch Assy | 1 | 900 | 47 | Text Dwg |
| 210 | Binding Post | 2 | 200 | 60 | 3 |
| 215 | Battery Holder | 1 | 200 | 60 | 4 |
| 220 | Lock Washer #6 | 5 | 200 & 700 | 61 | 1 |
| 225 | Shaft Clamp "B" | 1 | 200 | 61 | 2 |
| 300 | Large Sample Assy | 1 | 900 | 48 | Text Dwg |
| 310 | Bolt 8-32 FHMS .50 | 1 | 300 | 61 | 3 |
| 315 | Large Sample Hinge | 1 | 300 | 61 | 4 |
| 320 | Large Sample Knob | 1 | 300 | 62 | 1 |
| 325 | Nut 8-32 | 1 | 300 | 62 | 2 |
| 330 | Large Sample Plate | 1 | 300 | 62 | 3 |
| 335 | Large Sample Cover | 1 | 300 | 62 | 4 |
| 340 | Flat Washer #8 | 1 | 300 | 63 | 1 |
| 345 | Large Sample Insulator | 1 | 300 | 63 | 2 |
| 350 | Large Sample Strap | 1 | 300 | 63 | 3 |

TABLE 30-continued

Parts List for Radioscope

| # Part Name & Description | Qty Used | Next Ay # | FIG. | Item |
|---|---|---|---|---|
| 400 Small Sample Assy | 1 | 900 | 49 | Text Dwg |
| 410 Bolt 6-32 FHMS 1.06 | 2 | 400 | 63 | 4 |
| 415 Small Sample Cap | 1 | 400 | 64 | 1 |
| 420 Small Sample Cylinder | 1 | 400 | 64 | 2 |
| 430 Small Sample Plate | 1 | 400 | 64 | 3 |
| 450 Dial Sample Assy | 1 | 900 | 50 | Text Dwg |
| 455 Dial Sample "L" | 1 | 450 | 64 | 4 |
| 460 Rack Gear | 1 | 450 | 65 | 1 |
| 465 Dial Sample Insulator | 1 | 450 | 65 | 2 |
| 470 Dial Sample Insulator Support | 1 | 450 | 65 | 3 |
| 475 Dial Sample Specimen Clamp | 1 | 450 | 65 | 4 |
| 480 Dial Sample Rack Support | 1 | 450 | 66 | 1 |
| 485 Nut 4-40 | 2 | 450 | 66 | 2 |
| 490 Bolt Round Head 4-40 X .25 | 2 | 450 | 66 | 3 |
| 495 Bold 4-40 FHMS | 4 | 300–400 | 66 | 4 |
| 500 Lamp Housing Assy | 1 | 900 | 51 | Text Dwg |
| 510 Bolt 6-32 FHMS 1.75 | 1 | 500 | 67 | 1 |
| 515 Bolt 6-32 FHMS 2.00 | 1 | 500 | 67 | 2 |
| 520 Lamp 2.2 Volt | 4 | 500 | 67 | 3 |
| 525 Bolt & Nut 2-56 | 4 | 500 | 67 | 4 |
| 540 Lamp Conductor | 1 | 500 | 68 | 1 |
| 545 Lamp Insulator | 1 | 500 | 69 | 2 |
| 550 Lamp Housing | 1 | 500 | 70 | 3 |
| 555 Insulating Washer | 4 | 500 | 68 | 4 |
| 560 Lamp Solder Lug | 4 | 500 | 69 | 1 |
| 565 Lamp Socket | 4 | 500 | 69 | 2 |
| 570 #5 Wood Screw | 2 | 500 | 69 | 3 |
| 575 Colored Filter Blue | 1 | 500 | 69 | 4 |
| 580 Colored Filter Red | 1 | 500 | 70 | 1 |
| 585 Colored Filter Yellow | 1 | 500 | 70 | 2 |
| 590 Colored Filter Green | 1 | 500 | 70 | 3 |
| 600 Complete Case Assy | 1 | 100 | 78 | 1 |
| 605 Top Cover Assy | 1 | 600 | 78 | 2 |
| 610 Top Cover | 1 | 605 | 70 | 4 |
| 615 Box Lid Hinge | 2 | 605 | 71 | 1 |
| 620 Top Latch | 1 | 605 | 71 | 2 |
| 625 Cabinet Foot | 4 | 605 & 650 | 71 | 3 |
| 650 Bottom Cover Assy | 1 | 600 | 78 | 3 |
| 655 Bottom Cover | 1 | 650 | 71 | 4 |
| 660 Bottom Latch | 1 | 650 | 72 | 1 |
| 665 Bottom Handle | 1 | 650 | 72 | 2 |
| 700 Gamut Switch & Coil Assy | 1 | 900 | 52, 53 | Text Dwg |
| 705 Gamut Switch Washer | 4 | 700 | 72 | 3 |
| 710 Clamp Bolt 6-32 Fill HMS.40 | 5 | 700 & 800 | 72 | 4 |
| 715 Shaft Clamp | 4 | 700 | 73 | 1 |
| 720 Thousands Coil | 9 | 700 | 73 | 2 |
| 725 Hundreds Coil | 9 | 700 | 73 | 3 |
| 730 Tens Coil | 1 | 700 | 73 | 4 |
| 735 Units Coil | 1 | 700 | 74 | 1 |
| 740 Control Knob | 6 | 200 & 700 & 800 | 74 | 2 |
| 745 Nut 6-32 | 62 | Various | 74 | 3 |
| 750 Nut ½-13 | 5 | 200 & 700 & 800 | 74 | 4 |
| 755 Washer Flat #6 | 8 | 200 & 700 & 800 | 75 | 1 |
| 760 Switch Contact Pad | 45 | 200 & 700 | 75 | 2 |
| 765 Gamut Switch Solder Lug | 4 | 700 | 75 | 3 |
| 770 Solder Lug #6 | 30 | Various | 75 | 4 |
| 775 Switch Spring Bolt 6-32 | 5 | 200 & 700 | 76 | 1 |
| 780 Gamut Switch Leaf Spring | 10 | 200 & 700 | 76 | 2 |
| 785 Switch Stop Post | 10 | 200 & 700 | 76 | 3 |
| 790 Switch Bushing | 5 | 200 & 700 & 800 | 76 | 4 |
| 800 Dial Knob Assy | 1 | 900 | 54 | Text Dwg |
| 805 Machine Screw #6 FH X .25 | 1 | 800 | 77 | 1 |
| 810 Knob Pointer | 1 | 800 | 77 | 2 |
| 815 Dial Knob Washer | 1 | 800 | 77 | 3 |
| 820 Pinion Gear 14 Tooth | 1 | 800 | 77 | 4 |
| 900 Front Panel Assy | 1 | 100 | 78 | 4 |
| 900 Front Panel Assy | 1 | 100 | X | Text Dwg |
| 910 Front Panel Holes & Marking | 1 | 900 | 79 | 1 |
| S-100 Sensor, Head Probe and Ca Assy | 1 | 100 | 79 | 2 |
| S-105 Sensor, Head Probe Assy | 1 | S-105 | 79 | 3 |
| S-115 Sensor, Head Probe Body | 1 | S-100 | 79 | 4 |
| S-120 Sensor, Head Probe Disc | 1 | S-105 | 80 | 1 |
| S-125 Sensor, Head Probe 4-40 X .25 | 1 | S-105 | 80 | 2 |
| S-130 Sensor, Head Probe Handle | 1 | S-105 | 80 | 3 |
| S-135 Sensor Cable Pin Plug | 1 | S-100 | 80 | 4 |

TABLE 30-continued

Parts List for Radioscope

| # Part Name & Description | Qty Used | Next Ay # | FIG. | Item |
|---|---|---|---|---|
| S-140 Sensor Cable Alligator Clip | 1 | S-100 | 81 | 1 |
| S-145 Sensor Cable Coax Belt Loop | 1 | S-100 | 81 | 2 |
| S-150 Sensor Cable Coax Head Probe | 1 | S-100 | 81 | 3 |
| S-155 Sensor Cable Wire Interconnect | 1 | S-100 | 81 | 4 |
| S-160 Sensor Cable Belt Clip | 1 | S-100 | 82 | 1 |

The Complete Case Assembly.

The case assembly (# 600) is made up a top cover (# 605) and a bottom cover (# 650). This is made of vinyl covered wood and is necessary to protect and cover the sensitive elements within. See FIG. 42.

The Top Cover Assembly.

The top cover assembly (# 605) is made up a vinyl covered wood top cover (# 610), two hinges (# 615), two rubber feet (#625) and a top latch (#620). See FIG. 43.

The Bottom Cover Assembly.

The bottom cover assembly (# 650) is made up a vinyl covered wood bottom cover 655), two rubber feet (# 625), a handle (# 665) and a bottom latch (# 625). See FIG. 44.

The Front Panel Assembly (# 900).

The front panel assembly (# 900) shown above is made of several smaller assemblies shown in the following illustrations. One binding post and lamp switch assembly (# 200). One Large Sample Assembly (# 300). One Small Sample Assembly (# 400). One Dial Sample Assembly (# 450) which is below the panel surface. One Lamp Housing Assembly (# 500) which is below the panel surface). Four Gamut Switches and Coil Assemblies (# 700). One Variable Specimen Assembly (# 800). See FIG. 45.

Each of these assemblies attach to the Front Panel Holes and Marking (# 910). This front panel serves as the chassis or mounting surface for all these components. In the next few pages we'll look at these individual assemblies from a side view and see how they attach to (# 910)

Front Panel Holes and Marking (# 910).

This panel and mounting surface is made of black bakelite and is 1/8" thick. See FIG. 46.

Binding Post and Lamp Switch Assembly (# 200).

The binding post assembly consists of the Front Panel (# 910) into which we insert the binding post (# 210) then on the threaded end of the binding post we insert two #6 solder lugs (# 770) then thread on a 6-32 nut (# 745). There are two such assemblies mounted. One by the hole marked "F" and the other by the hole marked "S" on the panel (# 910). See FIG. 47.

The lamp switch assembly consists of the front panel (# 910) into which we mount five switch contact pads (# 760) into the five holes marked "OFF", "B", "Y", "R" and "G" and two switch stop posts (# 785) into the two holes directly below "OFF" and "G". We then thread on 6-32 nuts (# 745) on these seven items and tighten.

We then mount a switch bushing (# 790) in the hole below "OFF" and "G" mentioned above. Insert the battery holder (# 215) on the threaded end of the bushing and thread on the ½-13 nut on the bushing. Position the battery holder and tighten the nut.

We then locate control knob (# 740), place the #6 flat washer (# 755) on the threaded hole on the underside of the control knob. Then place two gamut switch leaf springs (# 780) together with the slotted part on the shaft and the hole over the flat washer with the bent part of the spring facing the end of the shaft. Then we place a #6 lock washer (# 220) on the hole. Lastly, we insert a 6-32 screw (# 755) through the above items and screw it into the threaded part of # 740. Tighten the screw.

Now we insert the control knob shaft (# 740) into the bushing (# 790) and press gently down on the knob while inserting on the shaft the shaft clamp "B" (# 225). With the leaf springs compressed slightly, tighten the set screw on (# 225). This assembly is now complete.

Large Sample Assembly (# 300).

The large sample assembly consists of the large sample cover (# 335) onto which we mount several parts. First insert the 8-32 FHMS (# 310) into the counter sunk hole in the large sample disc (# 330). Insert this same screw through the hole on the stepped side of the large sample cover (# 335), position the "U" notch of the hinge (# 315) over the bolt (# 310), place a #8 flat washer on the bolt, place an 8-32 nut (# 325) on the bolt and tighten. Insert a knob (# 320) on the threaded end of the bolt and tighten. See FIG. 48.

Next, insert switch stop post (# 785) through the hole on the small end of the hinge (# 315), then through the small hole right below the "F" binding post hole on (# 910). Insert the double chamfered end of the large sample strap (# 350) over the threaded end of the stop post. Install two #6 solder lugs (# 770) over the same threaded end and thread on the 6-32 nut (# 745) and tighten. Position the large sample insulator (# 345) over the two holes on the large sample strap (# 350). Insert two 4-40 screws (# 490) into these holes and thread into tapped 4-40 holes in # 910. Lastly, insert four 4-40×0.5" FHMS (# 495) into the four counter-sunk holes on the lower left of front panel (# 910). The two left screws will part of support dial sample insulator support (# 470) and the two right screws will support dial sample rack support (# 480).

Small Sample Assembly (# 400).

The small sample assembly consists of the front panel (# 910) onto which we mount several parts. First insert the 6-3×1.06 FHMS (# 410) into the two counter-sunk holes to the lower right of the large sample assembly (# 300). Over the screws install solder lugs (# 770), two on the left bolt and one on the right bolt. Thread on 6-32 nuts (# 745) on each screw. Position small sample cylinder (# 420) between bolts and center over large hole. Place small sample plate (# 430) over bolts and thread on 6-32 nuts (# 745) onto each bolt and tighten. Lastly, insert small sample cap (#415) into the hole on the front. See FIG. 49.

Dial Sample Assembly (# 450).

Note: The dial sample assembly is first assembled then attached to the underside of the front panel (# 910) using the 4-40 FHMS (# 495) indicated in FIG. 48. See FIG. 50.

To assemble the # 440, first insert the rack gear (# 460) into the dial sample "L" (# 455) and insert the locking pin to lock the "L" to the rack gear. Slip onto the toothed end of the rack gear (# 460) the dial sample rack support (# 480). Slip onto the other end of the rack gear (# 460) the dial sample insulator (# 465) and the dial sample insulator support (# 470). Note: the dial sample insulator (# 465) and the dial sample insulator support (# 470) have been previously riveted together. Place the dial sample specimen clamp (# 475) over the tapped holes in the dial sample "L" (# 455), insert the two round head 4-40 screws (# 490) into the holes and tighten. While supporting this complete assembly, position it on the underside of the front panel (# 910) and using the 4-40 FHMS (# 495) indicated in FIG. 48, secure the dial sample rack support (# 480) by threading the screws into the tapped holes. Secure the dial sample insulator support (# 470) by threading on two 4-40 nuts onto the two remaining screws indicated in FIG. 48.

Lamp Housing Assembly (# 500).

The lamp housing is first assembled then attached to the underside of the front panel (# 910) using the 4-40 FHMS (# 510 & 515) indicated in FIG. 51. See FIG. 51.

Place on lamp insulator (# 545) lamp conductor (# 540) and align holes. Assemble four of the following: insert 2-56 bolt (# 525) into insulating washer (# 555) and into lamp socket (# 565) and through lamp solder lug (# 560) then insert each bolt through the holes #2, #3, #4, #5 on lamp insulator (# 545) then through the holes #2, #3, #4, #5 on lamp conductor (# 540). Place 2-56 nut (# 525) onto the four bolts and tighten.

Next install the four lamps 2.2 Volt (# 520) into lamp socket (# 565). Position the solder lugs (# 560) so they rest in the notches of the lamp housing (# 550). Attach this assembly to the lamp housing (# 550) using two #5 wood screws (# 570).

Attach the four colored plastic rectangles (# 590, 585, 580, 575) directly over the four large holes on the front of the lamp housing (# 550) and tape edges in place. Lay a piece of 0.066" dia. wire 10" long over the four light holes on the back of the front panel (# 910). Insert 6-32×2" FHMS (# 515) through the front panel hole closest to the "S" binding post. Insert 6-32×1.75" FHMS (# 510) through the front panel hole between the two left light hole patterns. On these two bolts, insert the lamp housing (# 550) with the colored papers against the 0.066 dia. wire. On the 6-32×2" FHMS (# 515) insert two #6 flat washers (# 755) and on the 6-32×1.75" FHMS (# 510) insert one #6 flat washers (# 755). On these to bolts thread on a 6-32 nut and tighten. It may be necessary to adjust position of the 0.066 diameter wire when all connections are made and soldered.

Gamut Switch and Coil Assembly (# 700).

The gamut switch contacts and coil assembly consists of the front panel (# 910) into which we mount forty switch contact pads (# 760) into the forty holes marked 0-9 and two switch stop posts (# 785) into each pair of holes near 0 and 9. Only on the twenty switch contact holes in the thousands and hundreds dials we include a solder lug (# 770) at each hole. We then thread on 6-32 nuts (# 745) on these 48 items and tighten. On the 10 switch contacts in the thousands switch posts we thread onto the post a thousands coil (# 720) onto each post. On the 10 switch contacts in the hundreds switch posts we thread onto the post a hundreds coil (# 725) onto each post. On the 10 switch contacts in the tens switch posts we solder onto the post a tens coil (# 730) onto each post at the bend in the coil. On the 10 switch contacts in the units switch posts we solder onto the post a tens coil (# 735) onto each post at the bend in the coil. All the coils are connected in series in the "hundreds" and "thousands" switches. See FIG. 52.

Gamut Switch and Coil Assembly (# 700).

The gamut switch assembly consists of the front panel (# 910) into which we insert four sets of the following items in the four holes across the top of the panel. A switch bushing (# 790), then a gamut switch solder lug (# 765) on the threaded end of the bushing and then thread on the ½-13 nut on the bushing then tighten the nut. See FIG. 53.

We then locate control knob (# 740), place the #6 flat washer (# 755) on the threaded hole on the underside of the control knob. Then place two gamut switch leaf springs (# 780) place together with the slotted part on the shaft and the hole over the flat washer with the bent part of the spring facing the end of the shaft. Then we place a #6 lock washer (# 220) on the hole. Lastly, we insert a 6-32 screw (# 755) through the above items and screw it into the threaded part of # 740. Tighten the screw.

Now we insert the control knob shaft (# 740) into the bushing (# 790) and press gently down on the knob while inserting on the shaft the gamut switch washer (# 705) and shaft clamp (# 715). With the leaf springs compressed slightly, tighten the set screw (# 710). This assembly is now complete.

Dial Knob Assembly (# 800).

The dial knob assembly consists of the front panel (# 910) into which we a switch bushing (# 790), then a dial knob washer (# 815) on the threaded end of the bushing and then thread on the ½-13 nut (# 815) on the bushing then tighten the nut. See FIG. 54.

We then locate control knob (# 740), place the knob pointer # 810) over the threaded hole on the underside of the knob and insert the #6 FHMS (# 805) through the hole and tighten the screw.

Now we insert the control knob shaft (# 740) into the bushing (# 790) and press gently down on the knob while inserting on the shaft the 14-tooth pinion gear (# 820). At this point is necessary to rotate the dial sample rack gear (# 460) on it's long axis so the rack gear teeth mesh with the 14 tooth pinion gear. When the teeth are meshed, position the rack gear all the way in toward the Radioscope and rotate the 0-7 knob to "0" and tighten the set screw (# 710) in the gear (# 820). Check for smooth operation of this rack and pinion assembly. This assembly is now complete.

Installing the Battery (# 100).

From the back side of the front panel (# 910) insert the battery (# 120) into the battery holder (# 215) with the negative terminal into the battery holder. Insert the battery clamp (# 110) over the threaded end of the 6-32 FHMS (# 515) with the sharp pointed contacts bearing against the lamp conductor (# 540) then position the other end of the clamp over the positive pole of the battery. Thread onto the 6-32 FHMS (# 515) the battery clamp nut (# 115) and tighten. The battery should be secure in its holder. See FIG. 55.

Wiring the Coils (# 100).

From the back side of the front panel (# 910) all the coils are wired in series. A 0.066" dia. wire is attached from the gamut switch solder lug (# 765) to the "0" switch contact pad (# 760) of the previous switch. Between switch contact pads "0" and "1" a coil will be attached to the solder lugs then between switch contact pads "1" and "2" a coil will be attached, etc. To check coil wiring, when all switches are set to "0" all the coils are in the circuit and connected in series. When all switches are set to "9" all the coils are out of the circuit and the switches are at minimum resistance. See FIG. 56.

Complete Blood Analysis Procedure

Procedure for Getting a Blood Sample

Items Required:

1. A tissue paper on which a blood sample is to be placed by contact of the paper with a drop of blood as it oozes from the wound. (Note: Any touching of sample paper at any time with fingers or with any steel object will contaminate it.)

2. Folded aluminum foils, each containing the above mentioned paper.

3. Two aluminum tweezers for handling sample and foil.

Note: Generally only one dime-sized sample is needed from a particular donor.

Procedure:

1. Using aluminum tweezers, unwrap foil so as to make sample paper easily accessible.
2. Draw window shades until there is just enough light to enable one to see well enough to readily take sample.
3. Rub ear lobe briskly with dry absorbent cotton so as to improve blood circulation in ear lobe. (Do not apply any alcohol on ear lobe before taking sample as it will contaminate sample.)
4. Prick lobe of (either) ear very gently with a sharp sterile blade, and only enough to cause a drop of blood to ooze out with gentle pinching of ear with fingers.
5. Using aluminum tweezers (so as not to touch sample paper with hand) press sample paper against wound to absorb enough blood to make a spot at least the size of a dime on one side of the sample paper. (If more blood is needed for sample, repeat pinching procedure.)

Notes:

1. Any exposure of sample to bright light or even to weak magnetic field—such as touching sample paper with scissors or steel tweezers—adversely affects sample.
2. If instrument used for pricking is not already sterile, boil it, but do not treat with alcohol to avoid any contamination.
3. To avoid contamination of next sample, either discard instrument used in pricking earlobes or boil the sharp instrument before reuse.
4. Using aluminum tweezers, replace sample paper (with blood spot up) on aluminum wrapper and re-fold aluminum wrapper until sample is completely covered by aluminum wrapper so as to prevent exposure to light or contamination by contact with anything but the foil in which sample is wrapped.
5. Place each foil containing sample in a separate envelope on which is written date and time of day and identification of donor of sample.
6. Raise window shades.
7. The sample should be analyzed when it is as "fresh" as possible Preparing for Radioscope Blood Analysis Some Things to Consider Our experience has proven that some details that seem unimportant have a profound effecton the success of a blood analysis session.

1. Both the reagent and the operator should wear white cotton clothes during analysis. Other colors will work as long as they are not bright or vibrant colors.
2. The operator should wear leather-soled shoes.
3. The reagent should be in stocking feet.
4. The reagent should be in good general health, can be male or female and the age of the reagent is not a critical factor. Male reagents respond differently than female reagents and one reagent is different than another. The operator must adjust to the slight variations between reagents.
5. The reagent should take no vitamins or medicine 24 hours before the session.
6. The setup and complete approach should be methodical and consistent between measurements and between blood analysis sessions.
7. During analysis, the operator should be able to periodically touch (with her foot) a ground plate which is tied to "Earth" ground when she makes any Radioscope adjustments or settings.
8. A wooden floor is much better than a carpeted floor which can develop high electrostatic charges.
9. It's best to keep the number of people in the room to a minimum and lights dimmed.
10. A cool dry day is better than a hot humid day since the rod has a tendency to stick if the reagent is perspiring. Sometimes an ice pack has been used to cool the abdomen of the reagent.

Setting up the Radioscope

Before the blood testing starts, it is necessary to set up the Radioscope using the following procedure.

1. Position the Radioscope so that the movable sample axis is on a North-West/South-East line, that is, be sure the axis of the large sample strap (# 350) is on a North-South line.
2. Turn all the knobs counter clock-wise and demagnetize the Radioscope by using a strong horse shoe magnet. Approach areas to be demagnetized perpendicular to the panel surface and from about a foot away, bring the magnet slowly toward and away from each of the front panel components in the following order:
   A. The variable sample holder (from the left size)
   B. The large sample holder
   C. The small sample holder
   D. The four sets of switch contacts
   E. The four switch knobs
   F. The dial area and knob assembly Note: It is not necessary to demagnetize the colored lights nor the light switch.

3. Lower the room lights but keep it bright enough to see what you are doing.
4. While standing on a grounding plate, carefully unwrap the blood sample foil folder and insert the blood sample using the two aluminum tweezers. Insert the sample between "Dial Sample Specimen Clamp" and "Rack Gear" end (# 475 and # 460). Be sure the blood side of the tissue is toward the brass plate, Dial Sample Insulator Support (# 470). Position the blood sample so that part of the dried blood is against the center of the hard rubber Rack Gear (# 460) and part off to one side.
5. Set a timer and wait ten minutes for stabilization.
6. Position the reagent. The reagent faces West (but East would work) and remains standing during the tests.
7. Connect the reagent to the Radioscope using the Sensor Head Probe and Cable Assembly, (# SI00).
8. The Sensor Cable Pin Plug (# S135) on the end of cable Sensor Cable Coax Head Probe, (# S150) will connect to the "S" binding post on the Radioscope.
9. The Sensor Cable Pin Plug (# S135) on the end of cable Sensor Cable Coax Belt Loop, (# S145) will connect to the "F" binding post on the Radioscope.
10. The Sensor Cable Alligator Clip (# S140) on the end of cable Sensor Cable Coax Belt Loop, (# S145) will connect to the Sensor Cable Belt Clip (# S160).
11. Position the belt clip at the waist of the reagent so that the large metal surface of the clip rests against the reagent's skin. It is generally positioned at the side of the reagent so the wires don't interfere with the stroking of the operator.
12. The operator generally remains seated. The Radioscope is about 30" off the ground. The operator, reagent and Radioscope would form an equilateral triangle with each being at arm's length from each other.

Ready to Run a Blood Analysis

Running a Blood Test Using the Radioscope

Initially, it is important to find the exact location of the SV location on the forehead. This first test is to enable the operator to pin-point that location and get an idea of the general health of the patient.
1. The operator will now rotate the 0-7 variable Dial Knob Assembly (# 800) to 7 and set the four knobs, (# 700) to 5700 to check the blood for general toxins.
2. The operator will place the Sensor, Head Probe Assy (# S105) electrode on the SV (Splanchno-Vascular) location on the forehead just above and between the eyebrows. The reagent will hold it on that location by the handle of (# 105).
3. The operator will pick up the end of the Lucite rod (# 135), wipe it 2-3 times with a white cotton towel, touch the ground plate with her foot to remove any charge on her body, and start gently stroking the abdomen of the reagent with the rod.
4. While stroking, the operator will slowly rotate the 0-7 variable Dial Knob Assembly (# 800) counter clockwise toward "0". As she approaches "0" she is bringing the blood sample closer and closer to the Radioscope circuit. Actually increasing the coupling between the blood sample and the circuit. If the patient is in poor health, she could "get a stick" at about 2-3 on the dial. If the patient is in good health, the reading could be 0.25-0.50 on the dial.
5. The operator may choose to repeat the above test to confirm her reading. She would rotate the dial back up to 7. She would wipe the rod again with the white cotton cloth. She would touch ground, lift her foot, then start stroking the abdomen of the reagent while rotating the dial counter clock-wise toward zero. The reading most often repeats exactly. We have found it's best to start with the dial at 7. It is the most sensitive and repeatable approach and minimizes any "carry-over" of the reading from one setting to another.
6. If the above procedure wasn't successful, it may be necessary to adjust the position of the Sensor, Head Probe Assy (# S105) electrode. It might take two or three tries to get the most sensitive location for the Head electrode. When the best position is determined, the operator may mark the forehead of the reagent with a felt pen to record that location.

Continuing the Blood Tests

There are over 180 documented ailments in our toxin list called "The Gamut". The list is presented below. It is helpful if the operator has some idea where the patient is hurting. With that knowledge, it's easier to zero in on the particular toxin and its strength size and location. So the tests would continue as follows:
1. The reagent would break connection. That is, remove the head electrode and remove the clip from the waist then re-connect.
2. The operator would insure the head electrode is on the marked location.
3. The operator would rotate the dial back up to 7.
4. She would touch ground, turn all switches on the Radioscope to zero, then, for example, set the switches to 5000 (Carcinosis).
5. She would wipe the rod again with the white cotton cloth and touch her foot to ground to leak off any stored charge.
6. She would start stroking the abdomen of the reagent while rotating the dial counter clock-wise toward zero.
7. She would stop when the Lucite rod started to stick and note the dial setting. She may choose to repeat test to confirm her readings.
8. She may then choose another Radioscope setting and go through this same procedure over and over. After several tests, the operator gets a pretty good idea of the health of the patient and where the patient's problems are located.
9. The operator generally takes notes of dial settings, readings, date, patient, operator, reagent, and any unusual circumstances.

Strain Rates

Exact Location of the Problem

There are several ways to localize internal lesions. These are of great advantage for double checking the dial settings found. One way is to have a dial setting for each disease causing factor and then a different dial setting for each tissue, called strain rates, when attacked by one of these causes, each tissue is different from all others; hence the frequencies of chemical actions going on in them are different. For example: tuberculosis in a lung requires a dial setting of 4292 and tuberculosis in a kidney, a setting of 4276. See TABLE 31.

Localization

Another way to localize a lesion in the body is for the subject to fold his free hand with the fingers and thumb as nearly parallel as he can conveniently, then move the finger and thumb tips over his body, head and limbs while the operator is stroking the abdomen. The reaction will not manifest itself except where the hand is over a lesion of the kind tuned into. The exact size and shape of a lung lesion can thus be indicated. This affords a means of checking a reaction as well as indicating its size and shape. The position of the fingers is illustrated FIG. 57. The intensity of the energy is the same when specific settings are used as when the hand is used in localization.

The Gamut

To use the Radioscope properly this table, sensor and stroking locations are required. The shaded areas indicated on the abdomen of the reagent (near the navel) are general locations for gently stroking using the glass or Lucite rod. If a given disease is present, the operator will sense a sticking of the rod. The table below has several columns.

The four digit number preceding the description (example: 0800) indicates dial settings. This setting is the disease that is in the patients blood if a "Stick" is detected when stroking the abdomen. The one digit following the name (example: 4) indicates the electronic disease classification. The capital letters (example: SV) indicates the placing of the "S" electrode sensor on the head of the reagent. The single letter (example: H or C) indicates the location on the abdomen of the reagent where the operator will stroke the abdomen of the reagent with the rod in this area looking for a reaction to stroking. Some colors will negate or dissipate the reading and are listed here.

Dial Settings and Indicated Toxins

TABLE 31

GAMUT TABLE
Sorted by Dial Setting

| # | Description | Class | El | S | Diss |
|---|---|---|---|---|---|
| 0800 | Uric Acid | 4 | SV | H | |
| 1200 | Pyorrhea | 8 | ED | C | |
| 1200 | x-ray Burn | 0 | SV | E | |
| 1800 | Menopause | 2 | SP | D | |
| 2000 | Pain | 3 | SP | B | |
| 2300 | Amebiasis | 1 | SV | B | |
| 2355 | Typhus | 2 | SV | B | |
| 3700 | Radium Burn | 0 | ED | B | |
| 3800 | Actinomycosis | 5 | ED | D | |
| 3800 | Influenza | 5 | SV | C | |
| 3827 | Fallopian Tube w/CC | 5 | SV | H | |
| 3830 | Common Cold (CC) | 5 | SV | H | |
| 3831 | Bone w/CC | 5 | SV | H | |
| 3832 | Pancreas w/CC | 5 | SV | H | |
| 3833 | Brain w/CC | 5 | SV | H | |
| 3834 | Nerve Ending w/CC | 5 | SV | H | |
| 3835 | Skin w/CC | 5 | SV | H | |
| 3836 | Eye w/CC | 5 | SV | H | |
| 3842 | Colon w/CC | 5 | SV | H | |
| 3852 | Uterus w/CC | 5 | SV | H | |
| 3853 | Breast w/CC | 5 | SV | H | |
| 3872 | Liver w/CC | 5 | SV | H | |
| 3886 | Ovary w/CC | 5 | SV | H | |
| 3900 | Exotosis | 4 | SV | F | |
| 3900 | Measles | | SV | L | |
| 4000 | Inflammation | 3 | SP | B | |
| 4001 | Nicotine | 3 | ED | D | |
| 4100 | Hay Fever | 2 | SV | B | |
| 4200 | Human TB (HTB) | 5 | SV | C | Yellow |
| 4201 | Bovine TB | 5 | SV | C | Yellow |
| 4202 | Heart w/HTB | 5 | SV | C | |
| 4210 | Liver Function | | SV | B | |
| 4211 | Thyroid w/HTB | 5 | SV | C | |
| 4219 | Cervix w/HTB | 5 | SV | C | |
| 4221 | Stomach w/HTB | 5 | SV | C | |
| 4230 | Appendix w/HTB | 5 | SV | C | |
| 4236 | Ethmoid w/HTB | 5 | SV | C | |
| 4242 | Bladder w/HTB | 5 | SV | C | |
| 4243 | Tooth w/HTB | 5 | SV | C | |
| 4244 | Anthrum w/HTB | 5 | SV | C | |
| 4250 | Eye w/HTB | 5 | SV | C | |
| 4251 | Tonsil w/HTB | 5 | SV | C | |
| 4252 | Breast w/HTB | 5 | SV | C | |
| 4253 | Ear w/HTB | 5 | SV | C | |
| 4254 | Uterus | 5 | SV | C | |
| 4256 | Esophagus w/HTB | 5 | SV | C | |
| 4263 | Salivary Gland w/HTB | 5 | SV | C | |
| 4268 | Intestine w/HTB | 5 | SV | C | |
| 4270 | Bone w/HTB | 5 | SV | C | |
| 4271 | Liver w/HTB | 5 | SV | C | |
| 4272 | Pancreas w/HTB | 5 | SV | C | |
| 4273 | Gall Bladder w/HTB | 5 | SV | C | |
| 4274 | Skin w/HTB | 5 | SV | C | |
| 4276 | Kidney w/HTB | 5 | SV | C | |
| 4277 | Rectum w/HTB | 5 | SV | C | |
| 4278 | Ovary w/HTB | 5 | SV | C | |
| 4279 | Testicle w/HTB | 5 | SV | C | |
| 4282 | Prostate w/HTB | 5 | SV | C | |
| 4284 | Nerve Ending w/HTB | 5 | SV | C | |
| 4285 | Brain | 5 | SV | C | |
| 4288 | Sinus, Frontal w/HTB | 5 | SV | C | |
| 4292 | Lung w/HTB | 5 | SV | C | |
| 4297 | Lymph tissue w/HTB | 5 | SV | C | |
| 4298 | Blood Vessel w/HTB | 5 | SV | C | |
| 4300 | Pituitary, Post Fctn w/HTB | | SV | B | |
| 4302 | Pituitary, Anti Func. | | SV | B | |
| 4310 | Liver Function (Alternate) | | SV | B | |
| 4340 | Heart Function | | SV | B | |
| 4370 | Thyroid Function | | ED | B | |
| 4400 | Colisepsis | 4 | SV | B | |
| 4500 | Arthritis | 5 | SP | C | |
| 4530 | Kidney Function | | SV | B | |
| 4600 | Adrenal Function | | SV | B | |
| 4681 | Pin Worm | 1 | SV | E | |
| 4700 | Diphtheria | 2 | SV | C | |
| 4800 | Fatty Tumor | 3 and 6 | SV | C | |
| 4804 | Pancreas Function | | SV | D | |
| 4838 | Dental Caries | | SV | C | |
| 4900 | Parathyroidal Function | | SV | A | |
| 4937 | General Resistance | | SP | B | Red |
| 4939 | General Resistance | | SP | B | Blue |
| 5000 | Carcinosis | 6 | SV | C | Red |
| 5006 | Spleen w/Carcinosis | 6 | SV | C | |
| 5010 | Pancreas w/Carcinosis | 6 | SV | C | |
| 5021 | Gall Bladder w/Carcinosis | 6 | SV | C | |
| 5022 | Liver w/Carcinosis | 6 | SV | C | |
| 5023 | Nerve w/Carcinosis | 6 | SV | C | |
| 5024 | Esophagus w/Carcinosis | 6 | SV | C | |
| 5025 | Skin w/Carcinosis | 6 | SV | C | |
| 5027 | Uterus w/Carcinosis | 6 | SV | C | |
| 5030 | Thyroid w/Carcinosis | 6 | SV | C | |
| 5031 | Stomach w/Carcinosis | 6 | SV | C | |
| 5035 | Gum w/Carcinosis | 6 | SV | C | |
| 5050 | Blood Vessel w/Carcinosis | 6 | SV | C | |
| 5052 | Intestine w/Carcinosis | 6 | SV | C | |
| 5062 | Prostate w/Carcinosis | 6 | SV | C | |
| 5063 | Breast w/Carcinosis | 6 | SV | C | |
| 5064 | Kidney w/Carcinosis | 6 | SV | C | |
| 5072 | Ovary w/Carcinosis | 6 | SV | C | |
| 5073 | Lung w/Carcinosis | 6 | SV | C | |
| 5079 | Garuncle, Urethral | 6 | SV | C | |
| 5096 | Bone w/Carcinosis | 6 | SV | C | |
| 5100 | Gonad Function | | ED | D | |
| 5100 | Whooping Cough | | ED | B | |
| 5100 | Mumps | | SP | C | |
| 5200 | Variola | 2 | SV | B | |
| 5200 | Neisserian | 4 | ED | C | |
| 5209 | Kidney w/Neisserian | 4 | ED | C | |
| 5224 | Catarrh | 4 | ED | C | Green |
| 5272 | Catarrh | 4 | ED | C | Green |
| 5300 | Eczema | 6 | SV | A | |
| 5400 | Necrosis Spleen | | | C | |
| 5500 | Lues | 3 | SV | C | Blue |
| 5502 | Leg Sore w/Lues | 3 | SV | C | |
| 5508 | Stomach w/Lues | 3 | SV | C | |
| 5563 | Prostate w/Lues | 3 | SV | C | |
| 5578 | Gastric Inflammation | 3 | SV | C | |
| 5600 | Lung Congestion | 7 | ED | D | Green |
| 5700 | General Toxins | 5 | SV | A | Green |
| 5740 | Chondroma | 2 | SV | C | |
| 5800 | Connect Tissue Scar (CTS) | 0 | SV | C | |
| 5800 | Sarcosis | 3 | SV | C | Red |
| 5801 | Bone w/CTS | 0 | SV | C | |
| 5802 | CT in Soft Tissue (CTST) | 3 | SV | C | |

TABLE 31-continued

GAMUT TABLE
Sorted by Dial Setting

| # | Description | Class | El | S | Diss |
|---|---|---|---|---|---|
| 5803 | Lung w/CTS | 0 | SV | C | |
| 5811 | Gall Bladder w/Sarcosis | 3 | SV | C | |
| 5813 | Liver w/Sarcosis | 3 | SV | C | |
| 5820 | Prostate w/Sarcosis | 3 | SV | C | |
| 5821 | Uterus w/(CTST) | 3 | SV | C | |
| 5822 | Ovary w/(CTST) | 3 | SV | C | |
| 5826 | Skin w/(CTST) | 3 | SV | C | |
| 5831 | Bone w/(CTST) | 3 | SV | C | |
| 5832 | Adhesion w/CTS | 0 | SV | C | |
| 5835 | Heart w/(CTST) | 3 | SV | C | |
| 5840 | Lymph w/(CTST) | 3 | SV | C | |
| 5846 | Breast w/(CTST) | 3 | SV | C | |
| 5850 | Intestine w/(CTST) | 3 | SV | C | |
| 5852 | Bone Marrow w/(CTST) | 3 | SV | C | |
| 5853 | Stomach w/(CTST) | 3 | SV | C | |
| 5854 | Spleen w/(CTST) | 3 | SV | C | |
| 5883 | Brain w/(CTST) | 3 | SV | C | |
| 5891 | Pancreas w/(CTST) | 3 | SV | C | |
| 5900 | Ovarian Cyst w/(CTST) | 3 | SV | C | |
| 5930 | Cholelithiasis | 4 | SV | P | |
| 5957 | Bang's Disease | 5 | SV | C | |
| 5967 | Undulant Fever | 5 | SV | C | |
| 5971 | Malta Fever | 6 | SV | E | |
| 6000 | Streptoxoxemia | 2 | SV | B | Red |
| 6004 | Colon w/Streptoxoxemia | 2 | SV | B | |
| 6026 | Pancreas w/Streptoxoxemia | 2 | SV | B | |
| 6030 | Malaria | 1 | SV | B | |
| 6073 | Tooth w/Streptoxoxemia | 2 | SV | B | |
| 6442 | Pus, free | | SV | B | |
| 6463 | Pus, encapsulated | 1 or 2 | SV | B | |
| 6600 | Staphylotoxemia | 1 | ED | C | |
| 6604 | Eye w/Staphylotoxemia | 1 | ED | C | |
| 6619 | Tooth w/Staphylotoxemia | 1 | ED | C | |
| 6641 | Uterus w/Staphylotoxemia | 1 | ED | C | |
| 6643 | Tonsil w/Staphylotoxemia | 1 | ED | C | |
| 6651 | Ovary w/Staphylotoxemia | 1 | ED | C | |
| 7020 | Sex Function - Female | | SV | B | |
| 7020 | Sex Function - Male | | SV | B | |
| 7240 | Human TB (HTB) | 5 | SV | C | Yellow |
| 7350 | Rhus Toxicodenden | 3 | SV | B | |
| 8000 | Psora | 4 or 5 | SV | B | |
| 8020 | Fibroma (L = Liver) | 2 | L | C | |
| 8040 | Infantile Paralysis | 8 | SV | C | |
| 8220 | Carcinosis | 6 | SV | C | Red |
| 8330 | Scarlitna | 6 | SV | B | |
| 8978 | Renal Stones | 8 | SV | D | |
| 9153 | Chilblains | 0 | SV | D | |
| 9221 | Rocky Mountain Fever | 5 | SV | E | |
| 9230 | Lues | 3 | SV | C | Blue |
| 9410 | Lung Congestion | 7 | ED | D | Green |
| 9491 | Malignancy | 6 | SV | E | |
| 9512 | Typhoid | 10 | SV | E | |
| 9650 | General Toxins | 5 | SV | A | Green |
| 9680 | Impetigo | | SV | C | |
| 9740 | Fermentation | 4 | SV | C | |
| 9820 | Putrefaction | 4 | SV | C | |
| 9860 | Sarcosis | 3 | SV | C | Red |
| 9980 | Streptoxoxemia | 2 | SV | B | Red |

We claim:

1. A method for diagnosing and treating an illness in a subject comprising:

testing a biological sample from said subject in a radioscope;

diagnosing said subject's illness by comparing the results of said testing with a tabulation of prior test results;

treating said illness with a therapeutic apparatus comprising means for generating a radio frequency signal superimposed on an approximately 60 Hz, 50% duty cycle square wave signal pulsed at a second 50% duty cycle at approximately 1.167 Hz, and a wire loop, one end of which is connected to the output of said generation means, and the other end of which is grounded with respect to said generation means;

monitoring the results of said treatment by a second use of a radioscope;

redetermining said diagnosis by comparing the results of said second radioscope use with said tabulation of prior test results;

adjusting said treatment if necessary in accordance with said redetermined diagnosis.

* * * * *